United States Patent
Goodman et al.

(10) Patent No.: US 10,493,113 B2
(45) Date of Patent: Dec. 3, 2019

(54) **COMPOSITIONS AND METHODS FOR TREATING DISEASE USING A *BLAUTIA* STRAIN**

(71) Applicant: Evelo Biosciences, Inc., Cambridge, MA (US)

(72) Inventors: Brian Goodman, Jamaica Plain, MA (US); Holly Ponichtera, Cambridge, MA (US); Andrea Itano, Arlington, MA (US); Taylor A. Cormack, Dedham, MA (US); Maria Sizova, Roslindale, MA (US); Valeria Kravitz, Norwood, MA (US); Ekaterina Gavrish, Natick, MA (US); Carolina Baez-Giangreco, Boston, MA (US)

(73) Assignee: Evelo Biosciences, Inc., Cambridge, MA (US)

( * ) Notice: Subject to any disclaimer, the term of this patent is extended or adjusted under 35 U.S.C. 154(b) by 0 days.

(21) Appl. No.: 16/190,735

(22) Filed: Nov. 14, 2018

(65) Prior Publication Data

US 2019/0216862 A1    Jul. 18, 2019

Related U.S. Application Data

(60) Provisional application No. 62/585,782, filed on Nov. 14, 2017.

(51) Int. Cl.
| | | |
|---|---|---|
| *A01N 63/00* | (2006.01) |
| *A61K 35/742* | (2015.01) |
| *C12R 1/01* | (2006.01) |
| *A61P 35/00* | (2006.01) |
| *A61P 37/00* | (2006.01) |

(52) U.S. Cl.
CPC ............ *A61K 35/742* (2013.01); *A61P 35/00* (2018.01); *A61P 37/00* (2018.01); *C12R 1/01* (2013.01)

(58) Field of Classification Search
CPC .................................................... A61K 35/742
See application file for complete search history.

(56) References Cited

U.S. PATENT DOCUMENTS

| | | |
|---|---|---|
| 2016/0213702 A1 | 7/2016 | von Maltzahn et al. |
| 2016/0271188 A1 | 9/2016 | Berry et al. |

FOREIGN PATENT DOCUMENTS

| | | |
|---|---|---|
| WO | WO-2014/201037 A2 | 12/2014 |
| WO | WO-2016/086161 A1 | 6/2016 |
| WO | WO-2016/172657 A2 | 10/2016 |

OTHER PUBLICATIONS

Clavel et al., "Isolation of bacteria from mouse caecal samples and description of *Bacteroides sartorii* sp. nov.," Archives of Microbiology, 192(6):427-435 (2010).

International Search Report and Written Opinion for International Application No. PCT/US2018/060998 dated Feb. 25, 2019, 15 pages.

*Primary Examiner* — Albert M Navarro
(74) *Attorney, Agent, or Firm* — Foley Hoag LLP

(57) ABSTRACT

Provided herein are methods and compositions related to *Blautia* Strain A useful as therapeutic agents.

21 Claims, 6 Drawing Sheets

US 10,493,113 B2

COMPOSITIONS AND METHODS FOR TREATING DISEASE USING A *BLAUTIA* STRAIN

RELATED APPLICATION

This application claims the benefit of priority to U.S. Provisional Patent Application Ser. No. 62/585,782, filed Nov. 14, 2017, which is hereby incorporated herein by reference in its entirety.

SUMMARY

In certain aspects, provided herein are methods and compositions (e.g., bacterial compositions, pharmaceutical compositions) related to the treatment and/or prevention of disease (e.g., cancer, autoimmune disease, inflammatory disease, metabolic disease), in a subject (e.g., a human subject) comprising administering a bacterial composition comprising *Blautia* Strain A and/or a product of such bacteria (e.g., extracellular vesicles (EVs) and/or pharmaceutically active biomasses (PhABs)). Also provided herein are methods of making and/or identifying such a bacterium and/or bacterial product. In some embodiments, provided here are bioreactors comprising such bacteria. In some embodiments, the *Blautia* Strain A is *Blautia* Strain A (ATCC Deposit Number PTA-125346). In some embodiments, the *Blautia* Strain A is a strain comprising at least 90%, at least 91%, at least 92%, at least 93%, at least 94%, at least 95%, at least 96%, at least 97%, at least 98%, or at least 99% sequence identity (e.g., at least 99.5% sequence identity, at least 99.6% sequence identity, at least 99.7% sequence identity, at least 99.8% sequence identity, at least 99.9% sequence identity) to the nucleotide sequence (e.g., genomic sequence, 16S sequence, CRISPR sequence) of the *Blautia* Strain A. In some embodiments, the administration of the bacterial composition treats the immune disorder in the subject. In some embodiments, the immune disorder is an autoimmune disease. In some embodiments, the immune disorder is an inflammatory disease. In some embodiments, the immune disorder is an allergy.

In some embodiments, provided herein are extracellular vesicles (EVs) produced by and/or generated by and/or isolated from *Blautia* Strain A provided herein. In some embodiments, the bacterial compositions comprise both *Blautia* Strain A EVs and whole *Blautia* Strain A bacteria (e.g., live bacteria, killed bacteria, attenuated bacteria). In certain embodiments, provided herein are bacterial compositions comprising *Blautia* Strain A bacteria in the absence of *Blautia* Strain A EVs. In some embodiments, the pharmaceutical compositions comprise *Blautia* Strain A EVs in the absence of *Blautia* Strain A bacteria.

In certain embodiments, provided herein are methods of treating a subject who has an immune disorder (e.g., an autoimmune disease, an inflammatory disease, an allergy), comprising administering to the subject a bacterial composition comprising *Blautia* Strain A (e.g., a killed bacterium, a live bacterium and/or an attenuated bacterium). In some embodiments, the *Blautia* Strain A is *Blautia* Strain A (ATCC Deposit Number PTA-125346). In some embodiments, the *Blautia* Strain A is a strain comprising at least 90%, at least 91%, at least 92%, at least 93%, at least 94%, at least 95%, at least 96%, at least 97%, at least 98%, or at least 99% sequence identity (e.g., genomic sequence identity, 16S sequence identity, CRISPR sequence identity) (e.g., at least 99.5% sequence identity, at least 99.6% sequence identity, at least 99.7% sequence identity, at least 99.8% sequence identity, at least 99.9% sequence identity) to the corresponding nucleotide sequence of the *Blautia* Strain A (ATCC Deposit Number PTA-125346). In some embodiments, at least 50%, 60%, 70%, 80%, 85%, 90%, 90%, 91%, 92%, 93%, 94%, 95%, 96%, 97%, 98% or 99% of the bacteria in the bacterial composition are *Blautia* Strain A. In some embodiments, all or substantially all of the bacteria in the bacterial formulation are *Blautia* Strain A. In some embodiments, the bacterial formulation comprises at least $1\times10^5$, $5\times10^5$, $1\times10^6$, $2\times10^6$, $3\times10^6$, $4\times10^6$, $5\times10^6\times10^6 7\times10^6$, $8\times10^6$, $9\times10^6$, $1\times10^7$, $2\times10^7$, $3\times10^7$, $4\times10$, $5\times10^7$, $6\times10^7$, $7\times10$, $8\times10^7$, $9\times10$, $1\times10^8$, $2\times10^8$, $3\times3\times10^8$, $4\times10$, $5\times10^8$, $6\times10^8$, $7\times10^8$, $8\times10^8$, $9\times10^8$ or $1\times10^9$ colony forming units of *Blautia* Strain A.

In certain embodiments, provided herein are methods of treating a subject who has a metabolic disease comprising administering to the subject a bacterial composition described herein. In certain embodiments, provided herein are methods of treating a subject who has cancer comprising administering to the subject a bacterial composition described herein.

In certain embodiments, provided herein are bacterial compositions comprising *Blautia* Strain A (e.g., a killed bacterium, a live bacterium and/or an attenuated bacterium) and/or a product of such bacteria (e.g., extracellular vesicles (EVs) and/or pharmaceutically active biomasses (PhABs)). In some embodiments, at least 50%, 60%, 70%, 80%, 85%, 90%, 90%, 91%, 92%, 93%, 94%, 95%, 96%, 97%, 98% or 99% of the bacteria in the bacterial composition are *Blautia* Strain A. In some embodiments, the *Blautia* Strain A is *Blautia* Strain A (ATCC Deposit Number PTA-125346). In some embodiments, the *Blautia* Strain A is a strain comprising at least 99% sequence identity (e.g., genomic sequence identity, 16S sequence identity, CRISPR sequence identity) (e.g., at least 99.5% sequence identity, at least 99.6% sequence identity, at least 99.7% sequence identity, at least 99.8% sequence identity, at least 99.9% sequence identity) to the nucleotide sequence of the *Blautia* Strain A (ATCC Deposit Number PTA-125346). In some embodiments, all or substantially all of the bacteria in the bacterial formulation are *Blautia* Strain A. In some embodiments, the bacterial formulation comprises at least $1\times10^5$, $5\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10$, $3\times10^7$, $4\times10^7$, $5\times10^7$, $6\times10^7$, $7\times10^7$, $8\times10^7$, $9\times10$, $1\times10^8$, $2\times10^8$, $3\times10^8$, $4\times10^8$, $5\times10^8$, $6\times10^8$, $7\times10^8$, $8\times10^8$, $9\times10^8$ or $1\times10^9$ colony forming units of *Blautia* Strain A. In some embodiments, the bacterial composition comprises EVs and/or PhABs (e.g., whole cells, fractions of cells, supernatant from fermentation, fractions of supernatant and/or extracellular vesicles) made from *Blautia* Strain A.

In some embodiments, the bacterial composition is administered orally, intravenously, intratumorally, or subcutaneously. In some embodiments, the bacterial composition is administered in 2 or more (e.g., 3 or more, 4 or more or 5 or more doses). In some embodiments, the administration to the subject of the two or more doses are separated by at least 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days or 21 days. In some embodiments, a second bacterium is administered as part of an ecological consortium.

In certain embodiments, the composition comprises a specific ratio of *Blautia* Strain A bacteria to *Blautia* Strain A EV particles. For example, in some embodiments, the pharmaceutical composition comprises at least 1 *Blautia* Strain A bacterium for every 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ *Blautia* Strain A EV particles. In some embodiments, the pharmaceutical composition comprises about 1 *Blautia* Strain A bacterium for every 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$ $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ *Blautia* Strain A EV particles. In some embodiments, the pharmaceutical composition comprises no more than 1 *Blautia* Strain A bacterium for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$ $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ *Blautia* Strain A EV particles. In some embodiments, the pharmaceutical composition comprises at least 1 *Blautia* Strain A EV particle for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$ $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ *Blautia* Strain A bacterium. In some embodiments, the pharmaceutical composition comprises about 1 *Blautia* Strain A EV particle for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$ $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ *Blautia* Strain A bacterium. In some embodiments, the pharmaceutical composition comprises no more than 1 *Blautia* Strain A EV particle for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ *Blautia* Strain A bacterium.

In certain embodiments, the bacterial composition suppresses the immune response in delayed-type hypersensitivity (DTH). In certain embodiments, the bacterial composition induces a regulatory T cell or an anti-inflammatory response. In certain embodiments, the bacterial composition inhibits antigen-specific responses. In certain embodiments, the bacterial composition treats allergic contact dermatitis. In certain embodiments, the bacterial composition treats autoimmune myocarditis. In certain embodiments, the bacterial composition treats diabetes mellitus type 1. In certain embodiments, the bacterial composition treats granulomas. In certain embodiments, the bacterial composition treats peripheral neuropathies. In certain embodiments, the bacterial composition treats Hashimoto's thyroiditis. In certain embodiments, the bacterial composition treats multiple sclerosis. In certain embodiments, the bacterial composition treats rheumatoid arthritis.

In certain embodiments, the bacterial composition treats inflammation of the colon. In certain embodiments, the bacterial composition treats colitis. Colitis may be acute and self-limited or long-term. In certain embodiments, the bacterial composition treats ulcerative colitis. In certain embodiments, the bacterial composition treats digestive diseases. In certain embodiments, the bacterial composition treats Crohn's disease. In certain embodiments, the bacterial composition treats inflammatory bowel disease (IBD). In certain embodiments, the bacterial composition treats microscopic colitis. In certain embodiments, the bacterial composition treats collagenous colitis. In certain embodiments, the bacterial composition treats diversion colitis. In certain embodiments, the bacterial composition treats chemical colitis. In certain embodiments, the bacterial composition treats ischemic colitis. In certain embodiments, the bacterial composition treats indeterminate colitis. In certain embodiments, the bacterial composition treats atypical colitis. In some embodiments, the method further comprises administering to the subject an additional therapeutic (e.g., an antibiotic, an immune suppressant, an anti-inflammatory agent). In some embodiments, the method further comprises administering to the subject is a second therapeutic bacterium.

In some embodiments, the subject is a mammal. In some embodiments, the subject is a human. In some embodiments, the subject is a non-human mammal (e.g., a dog, a cat, a cow, a horse, a pig, a donkey, a goat, a camel, a mouse, a rat, a guinea pig, a sheep, a llama, a monkey, a gorilla or a chimpanzee).

DETAILED DESCRIPTION

General

Figure 1:
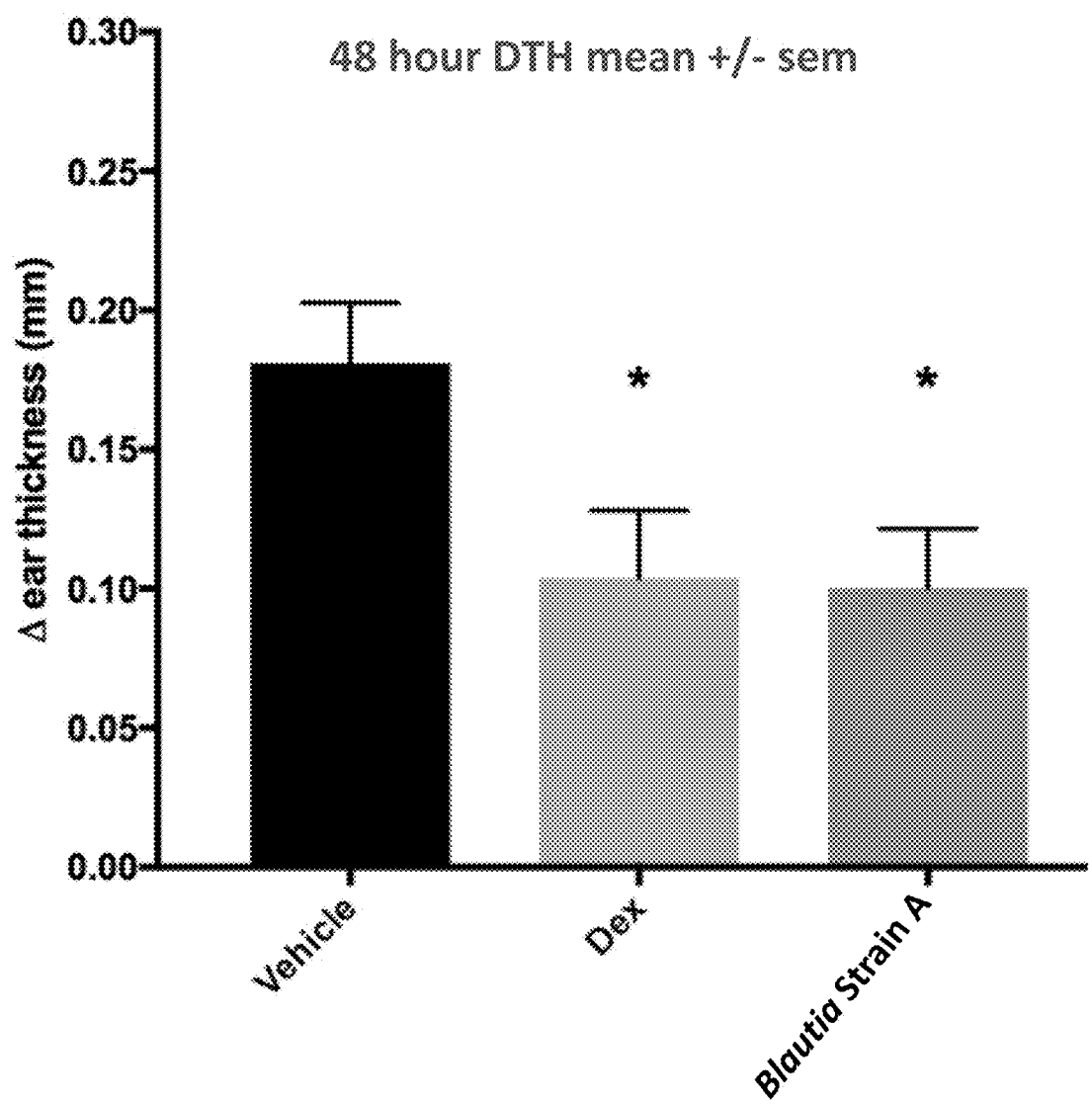
FIG. 1 shows the efficacy of orally administered *Blautia* Strain A in reducing antigen-specific ear swelling (ear thickness) compared to vehicle (negative control) and anti-inflammatory Dexamethasone (positive control) in a KLH-based delayed type hypersensitivity mouse model.

In certain aspects, provided herein are methods and compositions related to the treatment and/or prevention of disease (e.g., cancer, autoimmune disease, inflammatory disease, metabolic disease), in a subject (e.g., a human subject) comprising administering a bacterial composition comprising *Blautia* Strain A as well as methods of making and/or identifying such a bacterium.

In certain aspects, provided herein are methods of treating an immune disorder (e.g., an autoimmune disease, an inflammatory disease, an allergy) in a subject comprising administering to the subject a bacterial composition comprising *Blautia* Strain A.

Definitions

"Administration" broadly refers to a route of administration of a composition to a subject. Examples of routes of administration include oral administration, rectal administration, topical administration, inhalation (nasal) or injection. Administration by injection includes intravenous (IV), intramuscular (IM), intratumoral (IT) and subcutaneous (SC) administration. The pharmaceutical compositions described herein can be administered in any form by any effective route, including but not limited to intratumoral, oral, parenteral, enteral, intravenous, intraperitoneal, topical, transdermal (e.g., using any standard patch), intradermal, ophthalmic, (intra)nasally, local, non-oral, such as aerosol, inhalation, subcutaneous, intramuscular, buccal, sublingual, (trans)rectal, vaginal, intra-arterial, and intrathecal, transmucosal (e.g., sublingual, lingual, (trans)buccal, (trans)urethral, vaginal (e.g., trans- and perivaginally), intravesical, intrapulmonary, intraduodenal, intragastrical, and intrabronchial. In preferred embodiments, the pharmaceutical compositions described herein are administered orally, rectally, intratumorally, topically, intravesically, by injection into or adjacent to a draining lymph node, intravenously, by inhalation or aerosol, or subcutaneously.

As used herein, the term "antibody" may refer to both an intact antibody and an antigen binding fragment thereof. Intact antibodies are glycoproteins that include at least two heavy (H) chains and two light (L) chains inter-connected by disulfide bonds. Each heavy chain includes a heavy chain variable region (abbreviated herein as $V_H$) and a heavy chain constant region. Each light chain includes a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The term "antibody" includes, for example, monoclonal antibodies, polyclonal antibodies, chimeric antibodies, humanized antibodies, human antibodies, multispecific antibodies (e.g., bispecific antibodies), single-chain antibodies and antigen-binding antibody fragments.

The terms "antigen binding fragment" and "antigen-binding portion" of an antibody, as used herein, refers to one or more fragments of an antibody that retain the ability to bind to an antigen. Examples of binding fragments encompassed within the term "antigen-binding fragment" of an antibody include Fab, Fab', F(ab')$_2$, Fv, scFv, disulfide linked Fv, Fd, diabodies, single-chain antibodies, NANOBODIES®, isolated CDRH3, and other antibody fragments that retain at least a portion of the variable region of an intact antibody. These antibody fragments can be obtained using conventional recombinant and/or enzymatic techniques and can be screened for antigen binding in the same manner as intact antibodies.

"Cellular augmentation" broadly refers to the influx of cells or expansion of cells in an environment that are not substantially present in the environment prior to administration of a composition and not present in the composition itself. Cells that augment the environment include immune cells, stromal cells, bacterial and fungal cells. Environments of particular interest are the microenvironments where cancer cells reside or locate. In some instances, the microenvironment is a tumor microenvironment or a tumor draining lymph node. In other instances, the microenvironment is a pre-cancerous tissue site or the site of local administration of a composition or a site where the composition will accumulate after remote administration.

"Clade" refers to the OTUs or members of a phylogenetic tree that are downstream of a statistically valid node in a phylogenetic tree. The clade comprises a set of terminal leaves in the phylogenetic tree that is a distinct monophyletic evolutionary unit and that share some extent of sequence similarity. "Operational taxonomic units," "OTU" (or plural "OTUs") refer to a terminal leaf in a phylogenetic tree and is defined by a nucleic acid sequence, e.g., the entire genome, or a specific genetic sequence, and all sequences that share sequence identity to this nucleic acid sequence at the level of species. In some embodiments the specific genetic sequence may be the 16S sequence or a portion of the 16S sequence. In other embodiments, the entire genomes of two entities are sequenced and compared. In another embodiment, select regions such as multilocus sequence tags (MLST), specific genes, or sets of genes may be genetically compared, In 16S embodiments, OTUs that share ≥97% average nucleotide identity across the entire 6S or some variable region of the 16S are considered the same OTU (see e.g. Claesson M J, Wang Q. O'Sullivan O, Greene-Diniz R, Cole J R, Ros R P, and O'Toole P W. 2010. Comparison of two next-generation sequencing technoioigies for resolving highly complex microbiota composition using tandem variable 16S rRNA gene regions. *Nucleic Acids Res* 38: e200. Konstantinidis K T, Ramette A, and Tiedje J M. 2006. The bacterial species definition in the genomic era. *Philos Trans R Soc Lond B Biol Sci* 361: 1929-1940). In embodiments involving the complete genome, MLSTs, specific genes, or sets of genes OTUs that share ≥95% average nucleotide identity are considered the same OTU (see e.g. Achtman M, and Wagner M. 2008. Microbial diversity and the genetic nature of microbial species. *Nat Rev. Microbiol.* 6: 431-440. Konstantinidis K T, Ramnette A, and Tiedje J M. 2006. The bacterial species definition in the genomic era. *Philos Trans R Soc Lond B Biol Sci* 361: 1929-1940.). OTUs are frequency defined by comparing sequences between organisms. Generally, sequences with less than 95% sequence identity are not considered to form part of the same OTU. OTUs may also be characterized by any combination of nucleotide markers or genes, in particular highly conserved genes (e.g., "housekeeping" genes), or a combination thereof. Such characterization employs, e.g., WGS data or a whole genome sequence.

A "combination" of two or more monoclonal microbial strains includes the physical co-existence of the two monoclonal microbial strains, either in the same material or product or in physically connected products, as well as the temporal co-administration or co-localization of the monoclonal microbial strains.

The term "decrease" or "deplete" means a change, such that the difference is, depending on circumstances, at least 10%, 20%, 30%, 40%, 50%, 60%, 70%, 80%, 90%, 1/100, 1/1000, 1/10,000, 1/100,000, 1/1,000,000 or undetectable after treatment when compared to a pre-treatment state.

The term "ecological consortium" is a group of bacteria which trades metabolites and positively co-regulates one another, in contrast to two bacteria which induce host synergy through activating complementary host pathways for improved efficacy.

The term "epitope" means a protein determinant capable of specific binding to an antibody. Epitopes usually consist of chemically active surface groupings of molecules such as amino acids or sugar side chains. Certain epitopes can be defined by a particular sequence of amino acids to which an antibody is capable of binding.

As used herein, "engineered bacteria" are any bacteria that have been genetically altered from their natural state by human intervention and the progeny of any such bacteria. Engineered bacteria include, for example, the products of targeted genetic modification, the products of random mutagenesis screens and the products of directed evolution.

The term "gene" is used broadly to refer to any nucleic acid associated with a biological function. The term "gene" applies to a specific genomic sequence, as well as to a cDNA or an mRNA encoded by that genomic sequence.

"Identity" as between nucleic acid sequences of two nucleic acid molecules can be determined as a percentage of identity using known computer algorithms such as the "FASTA" program, using, for example, the default parameters as in Pearson et al. (1988) Proc. Natl. Acad. Sci. USA 85:2444 (other programs include the GCG program package (Devereux, J., et al., Nucleic Acids Research 12(I):387 (1984)), BLASTP, BLASTN, FASTA Atschul, S. F., et al., J Molec Biol 215:403 (1990); Guide to Huge Computers, Mrtin J. Bishop, ed., Academic Press, San Diego, 1994, and Carillo et al. (1988) SIAM J Applied Math 48:1073). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.)).

As used herein, the term "immune disorder" refers to any disease, disorder or disease symptom caused by an activity of the immune system, including autoimmune diseases, inflammatory diseases and allergies. Immune disorders include, but are not limited to, autoimmune diseases (e.g., Lupus, Scleroderma, hemolytic anemia, vasculitis, type one diabetes, Grave's disease, rheumatoid arthritis, multiple sclerosis, Goodpasture's syndrome, pernicious anemia and/or myopathy), inflammatory diseases (e.g., acne vulgaris, asthma, celiac disease, chronic prostatitis, glomerulonephritis, inflammatory bowel disease, pelvic inflammatory disease, reperfusion injury, rheumatoid arthritis, sarcoidosis, transplant rejection, vasculitis and/or interstitial cystitis), and/or an allergies (e.g., food allergies, drug allergies and/or environmental allergies).

The term "increase" means a change, such that the difference is, depending on circumstances, at least 10%, 20%, 30%, 40%, 50%, 60%, 70%, 80%, 90%, 2-fold, 4-fold, 10-fold, 100-fold, $10^3$ fold, $10^4$ fold, $10^5$ fold, $10^6$ fold, and/or $10^7$ fold greater after treatment when compared to a pre-treatment state. Properties that may be increased include immune cells, bacterial cells, stromal cells, myeloid derived suppressor cells, fibroblasts, metabolites, and cytokines.

The "internal transcribed spacer" or "ITS" is a piece of non-functional RNA located between structural ribosomal RNAs (rRNA) on a common precursor transcript often used for identification of eukaryotic species in particular fungi. The rRNA of fungi that forms the core of the ribosome is transcribed as a signal gene and consists of the 8S, 5.8S and 28S regions with ITS4 and 5 between the 8S and 5.8S and 5.8S and 28S regions, respectively. These two intercistronic segments between the 18S and 5.8S and 5.8S and 28S regions are removed by splicing and contain significant variation between species for barcoding purposes as previously described (Schoch et al Nuclear ribosomal internal transcribed spacer (ITS) region as a universal DNA barcode marker for Fungi. PNAS 109:6241-6246. 2012). 18S rDNA is traditionally used for phylogenetic reconstruction however the ITS can serve this function as it is generally highly conserved but contains hypervariable regions that harbor sufficient nucleotide diversity to differentiate genera and species of most fungus.

The term "isolated" or "enriched" encompasses a microbe, bacteria or other entity or substance that has been (1) separated from at least some of the components with which it was associated when initially produced (whether in nature or in an experimental setting), and/or (2) produced, prepared, purified, and/or manufactured by the hand of man. Isolated microbes may be separated from at least about 10%, about 20%, about 30%, about 40%, about 50%, about 60%, about 70%, about 80%, about 90%, or more of the other components with which they were initially associated. In some embodiments, isolated microbes are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. The terms "purify," "purifying" and "purified" refer to a microbe or other material that has been separated from at least some of the components with which it was associated either when initially produced or generated (e.g., whether in nature or in an experimental setting), or during any time after its initial production. A microbe or a microbial population may be considered purified if it is isolated at or after production, such as from a material or environment containing the microbe or microbial population, and a purified microbe or microbial population may contain other materials up to about 10%, about 20%, about 30%, about 40%, about 50%, about 60%, about 70%, about 80%, about 90%, or above about 90% and still be considered "isolated." In some embodiments, purified microbes or microbial population are more than about 80%, about 85%, about 90%, about 91%, about 92%, about 93%, about 94%, about 95%, about 96%, about 97%, about 98%, about 99%, or more than about 99% pure. In the instance of microbial compositions provided herein, the one or more microbial types present in the composition can be independently purified from one or more other microbes produced and/or present in the material or environment containing the microbial type. Microbial compositions and the microbial components thereof are generally purified from residual habitat products.

"Metabolite" as used herein refers to any and all molecular compounds, compositions, molecules, ions, co-factors, catalysts or nutrients used as substrates in any cellular or microbial metabolic reaction or resulting as product compounds, compositions, molecules, ions, co-factors, catalysts or nutrients from any cellular or microbial metabolic reaction.

"Microbe" refers to any natural or engineered organism characterized as a bacterium, fungus, microscopic alga, protozoan, and the stages of development or life cycle stages (e.g., vegetative, spore (including sporulation, dormancy, and germination), latent, biofilm) associated with the organism. Examples of gut microbes include: *Actinomyces graevenitzii, Actinomyces odontolyticus, Akkermansia muciniphila, Bacteroides caccae, Bacteroides fagilis, Bacteroides putredinis, Bacteroides thetaiotaomicron, Bacteroides vultagus, Bifidobacterium adolescentis, Bifidobacterium bifidum, Bilophila wadsworthia, Blautia, Butyrivibrio, Campylobacter gracilis,* Clostridia cluster III, Clostridia cluster IV, Clostridia cluster IX (Acidaminococcaceae group), Clostridia cluster XI, Clostridia cluster XIII (*Peptostreptococcus* group), Clostridia cluster XIV, Clostridia cluster XV, *Collinsella aerofaciens, Coprococcus, Corynebacterium sunsvallense, Desulfomonas pigra, Dorea formicigenerans, Dorea longicatena, Escherichia coli, Eubacterium hadrum, Eubacterium rectale, Faecalibacteria prausnitzii,* Gemella, *Lactococcus, Lanchnospira,* Mollicutes cluster XVI, *Mollicutes* cluster XVIII, *Prevotella, Rothia mucilaginosa,* Ruminococcus *callidus,* Ruminococcus *gnavus,* Ruminococcus *torques,* and *Streptococcus.*

"Microbiome" broadly refers to the microbes residing on or in body site of a subject or patient. Microbes in a microbiome may include bacteria, viruses, eukaryotic microorganisms, and/or viruses. Individual microbes in a microbiome may be metabolically active, dormant, latent, or exist as spores, may exist planktonically or in biofilms, or may be present in the microbiome in sustainable or transient manner. The microbiome may be a commensal or healthy-state microbiome or a disease-state microbiome. The microbiome may be native to the subject or patient, or components of the microbiome may be modulated, introduced, or depleted due to changes in health state (e.g., precancerous or cancerous state) or treatment conditions (e.g., antibiotic treatment, exposure to different microbes). In some aspects, the microbiome occurs at a mucosal surface. In some aspects, the microbiome is a gut microbiome. In some aspects, the microbiome is a tumor microbiome.

A "microbiome profile" or a "microbiome signature" of a tissue or sample refers to an at least partial characterization of the bacterial makeup of a microbiome. In some embodiments, a microbiome profile indicates whether at least 2, 3, 4, 5, 6, 7, 8, 9, 10, 15, 20, 25, 30, 35, 40, 45, 50, 55, 60, 65, 70, 75, 80, 85, 90, 95, 100 or more bacterial strains are present or absent in a microbiome.

"Modified" in reference to a bacteria broadly refers to a bacteria that has undergone a change from its wild-type form. Examples of bacterial modifications include genetic modification, gene expression, phenotype modification, formulation, chemical modification, and dose or concentration. Examples of improved properties are described throughout this specification and include, e.g., attenuation, auxotrophy, homing, or antigenicity. Phenotype modification might include, by way of example, bacteria growth in media that modify the phenotype of a bacterium that increase or decrease virulence.

As used herein, a gene is "overexpressed" in a bacteria if it is expressed at a higher level in an engineered bacteria under at least some conditions than it is expressed by a wild-type bacteria of the same species under the same conditions. Similarly, a gene is "underexpressed" in a bacteria if it is expressed at a lower level in an engineered bacteria under at least some conditions than it is expressed by a wild-type bacteria of the same species under the same conditions.

The terms "polynucleotide" and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

"Operational taxonomic units" and "OTU(s)" refer to a terminal leaf in a phylogenetic tree and is defined by a nucleic acid sequence, e.g., the entire genome, or a specific genetic sequence, and all sequences that share sequence identity to this nucleic acid sequence at the level of species. In some embodiments the specific genetic sequence may be the 16S sequence or a portion of the 16S sequence. In other embodiments, the entire genomes of two entities are sequenced and compared. In another embodiment, select regions such as multilocus sequence tags (MLST), specific genes, or sets of genes may be genetically compared. For 16S, OTUs that share ≥97% average nucleotide identity across the entire 16S or some variable region of the 16S are considered the same OTU. See e.g. Claesson M J, Wang Q, O'Sullivan O, Greene-Diniz R, Cole J R, Ross R P, and O'Toole P W. 2010. Comparison of two next-generation sequencing technologies for resolving highly complex microbiota composition using tandem variable 16S rRNA gene regions. Nucleic Acids Res 38: e200. Konstantinidis K T, Ramette A, and Tiedje J M. 2006. The bacterial species definition in the genomic era. Philos Trans R Soc Lond B Biol Sci 361: 1929-1940. For complete genomes, MLSTs, specific genes, other than 16S, or sets of genes OTUs that share ≥95% average nucleotide identity are considered the same OTU. See e.g., Achtman M, and Wagner M. 2008. Microbial diversity and the genetic nature of microbial species. Nat. Rev. Microbiol. 6: 431-440. Konstantinidis K T, Ramette A, and Tiedje J M. 2006. The bacterial species definition in the genomic era. Philos Trans R Soc Lond B Biol Sci 361: 1929-1940. OTUs are frequently defined by comparing sequences between organisms. Generally, sequences with less than 95% sequence identity are not considered to form part of the same OTU. OTUs may also be characterized by any combination of nucleotide markers or genes, in particular highly conserved genes (e.g., "housekeeping" genes), or a combination thereof. Operational Taxonomic Units (OTUs) with taxonomic assignments made to, e.g., genus, species, and phylogenetic clade are provided herein.

As used herein, "specific binding" refers to the ability of an antibody to bind to a predetermined antigen or the ability of a polypeptide to bind to its predetermined binding partner. Typically, an antibody or polypeptide specifically binds to its predetermined antigen or binding partner with an affinity corresponding to a $K_D$ of about $10^{-7}$ M or less, and binds to the predetermined antigen/binding partner with an affinity (as expressed by $K_D$) that is at least 10 fold less, at least 100 fold less or at least 1000 fold less than its affinity for binding to a non-specific and unrelated antigen/binding partner (e.g., BSA, casein). Alternatively, specific binding applies more broadly to a two component system where one component is a protein, lipid, or carbohydrate or combination thereof and engages with the second component which is a protein, lipid, carbohydrate or combination thereof in a specific way.

The terms "subject" or "patient" refers to any animal. A subject or a patient described as "in need thereof" refers to one in need of a treatment for a disease. Mammals (i.e., mammalian animals) include humans, laboratory animals (e.g., primates, rats, mice), livestock (e.g., cows, sheep, goats, pigs), and household pets (e.g., dogs, cats, rodents). For example, the subject may be a non-human mammal including but not limited to of a dog, a cat, a cow, a horse, a pig, a donkey, a goat, a camel, a mouse, a rat, a guinea pig, a sheep, a llama, a monkey, a gorilla or a chimpanzee. The subject or patient may be healthy, or may be suffering from an immune disorder at any developmental stage.

"Strain" refers to a member of a bacterial species with a genetic signature such that it may be differentiated from closely-related members of the same bacterial species. The genetic signature may be the absence of all or part of at least one gene, the absence of all or part of at least on regulatory region (e.g., a promoter, a terminator, a riboswitch, a ribosome binding site), the absence ("curing") of at least one native plasmid, the presence of at least one recombinant gene, the presence of at least one mutated gene, the presence of at least one foreign gene (a gene derived from another species), the presence at least one mutated regulatory region (e.g., a promoter, a terminator, a riboswitch, a ribosome binding site), the presence of at least one non-native plasmid, the presence of at least one antibiotic resistance cassette, or a combination thereof. Genetic signatures between different strains may be identified by PCR amplification optionally followed by DNA sequencing of the genomic region(s) of interest or of the whole genome. In the case in which one strain (compared with another of the same species) has gained or lost antibiotic resistance or gained or lost a biosynthetic capability (such as an auxotrophic strain), strains may be differentiated by selection or counter-selection using an antibiotic or nutrient/metabolite, respectively.

As used herein, the term "treating" a disease in a subject or "treating" a subject having or suspected of having a disease refers to subjecting the subject to a pharmaceutical treatment, e.g., the administration of one or more agents, such that at least one symptom of the disease is decreased or prevented from worsening. Thus, in one embodiment, "treating" refers inter alia to delaying progression, expediting remission, inducing remission, augmenting remission, speeding recovery, increasing efficacy of or decreasing resistance to alternative therapeutics, or a combination thereof.

Bacteria

In certain aspects, provided herein are methods of using a bacterial composition comprising *Blautia* Strain A and/or a product of such bacteria (e.g., extracellular vesicles (EVs) and/or pharmaceutically active biomasses (PhABs)). In some embodiments, the *Blautia* Strain A is *Blautia* Strain A (ATCC Deposit Number PTA-125346). In some embodiments, the *Blautia* Strain A is a strain comprising at least 90%, at least 91%, at least 92%, at least 93%, at least 94%, at least 95%, at least 96%, at least 97%, at least 98%, or at least 99% sequence identity (e.g., at least 99.5% sequence identity, at least 99.6% sequence identity, at least 99.7% sequence identity, at least 99.8% sequence identity, at least 99.9% sequence identity) to the nucleotide sequence (e.g., genomic, 16S or CRISPR nucleotide sequence) of the *Blautia* Strain A (ATCC Deposit Number PTA-125346).

Under the terms of the Budapest Treaty on the International Recognition of the Deposit of Microorganisms for the Purpose of Patent Procedure, the *Blautia* Strain A was deposited on Oct. 4, 2018, with the American Type Culture Collection (ATCC) of 10801 University Boulevard, Manassas, Va. 20110-2209 USA and was assigned ATCC Accession Number PTA-125346.

Applicant represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. 122. The deposited material will be maintained with all the care necessary to keep it viable and uncontaminated for a period of at least five years after the most recent request for the furnishing of a sample of the deposited plasmid, and in any case, for a period of at least thirty (30) years after the date of deposit or for the enforceable life of the patent, whichever period is longer. Applicant acknowledges its duty to replace the deposit should the depository be unable to furnish a sample when requested due to the condition of the deposit.

In some embodiments, the bacteria described herein are modified to improve colonization and/or engraftment in the mammalian gastrointestinal tract (e.g., modified metabolism, such as improved mucin degradation, enhanced competition profile, increased motility, increased adhesion to gut epithelial cells, modified chemotaxis). In some embodiments, the bacteria described herein are modified to enhance their immunomodulatory and/or therapeutic effect (e.g., either alone or in combination with another therapeutic agent). In some embodiments, the bacteria described herein are modified to enhance immune activation (e.g., through modified production of polysaccharides, pili, fimbriae, adhesins). In some embodiments, the bacteria described herein are modified to improve bacterial manufacturing (e.g., higher oxygen tolerance, improved freeze-thaw tolerance, shorter generation times).

*Blautia* Strain A can be cultured according to methods known in the art. For example, *Blautia* can be grown in ATCC Medium 2722, ATCC Medium 1490, or other medium using methods disclosed, for example in Caballero et al., 2017. "Cooperating Commensals Restore Colonization Resistance to Vancomycin-Resistant *Enterococcus faecium*" Cell Host & Microbe 21:592-602, which is hereby incorporated by reference in its entirety.

Production of EVs

In certain aspects, the *Blautia* Strain A bacteria EVs described herein can be prepared using any method known in the art.

In some embodiments, the *Blautia* Strain A bacteria EVs are prepared without an EV purification step. For example, in some embodiments, *Blautia* Strain A comprising the EVs described herein are killed using a method that leaves the *Blautia* Strain A EVs intact and the resulting bacterial components, including the EVs, are used in the methods and compositions described herein. In some embodiments, the *Blautia* Strain A bacteria are killed using an antibiotic (e.g., using an antibiotic described herein). In some embodiments, the *Blautia* Strain A bacteria are killed using UV irradiation.

In some embodiments, the EVs described herein are purified from one or more other bacterial components. Methods for purifying EVs from bacteria are known in the art. In some embodiments EVs are prepared from bacterial cultures using methods described in S. Bin Park, et al. PLoS ONE. 6(3):e17629 (2011) or G. Norheim, et al. PLoS ONE. 10(9): e0134353 (2015), each of which is hereby incorporated by reference in its entirety. In some embodiments, the bacteria are cultured to high optical density and then centrifuged to pellet bacteria (e.g., at 10,000×g for 30 min at 4° C., at 15,500×g for 15 min at 4° C.). In some embodiments, the culture supernatants are then passed through filters to exclude intact bacterial cells (e.g., a 0.22 µm filter). In some embodiments, the supernatants are then subjected to tangential flow filtration, during which the supernatant is concentrated, species smaller than 100 kDa are removed, and the media is partially exchanged with PBS. In some embodiments, filtered supernatants are centrifuged to pellet bacterial EVs (e.g., at 100,000-150,000×g for 1-3 hours at 4° C., at 200,000×g for 1-3 hours at 4° C.). In some embodiments, the EVs are further purified by resuspending the resulting EV pellets (e.g., in PBS), and applying the resuspended EVs to an Optiprep (iodixanol) gradient or gradient (e.g., a 30-60% discontinuous gradient, a 0-45% discontinuous gradient), followed by centrifugation (e.g., at 200,000×g for 4-20 hours at 4° C.). EV bands can be collected, diluted with PBS, and centrifuged to pellet the EVs (e.g., at 150,000×g for 3 hours at 4° C., at 200,000×g for 1 hour at 4° C.). The purified EVs can be stored, for example, at −80° C. or −20° C. until use. In some embodiments, the EVs are further purified by treatment with DNase and/or proteinase K.

For example, in some embodiments, cultures of *Blautia* Strain A bacteria disclosed herein can be centrifuged at 11,000×g for 20-40 min at 4° C. to pellet bacteria. Culture supernatants may be passed through a 0.22 µm filter to exclude intact bacterial cells. Filtered supernatants may then be concentrated using methods that may include, but are not limited to, ammonium sulfate precipitation, ultracentrifugation, or filtration. For example, for ammonium sulfate precipitation, 1.5-3 M ammonium sulfate can be added to filtered supernatant slowly, while stirring at 4° C. Precipitations can be incubated at 4° C. for 8-48 hours and then centrifuged at 11,000×g for 20-40 min at 4° C. The resulting pellets contain *Blautia* Strain A bacteria EVs and other debris. Using ultracentrifugation, filtered supernatants can be centrifuged at 100,000-200,000×g for 1-16 hours at 4° C. The pellet of this centrifugation contains *Blautia* Strain A bacteria EVs and other debris such as large protein complexes. In some embodiments, using a filtration technique, such as through the use of an Amicon Ultra spin filter or by tangential flow filtration, supernatants can be filtered so as to retain species of molecular weight >50 or 100 kDa.

Alternatively, EVs can be obtained from *Blautia* Strain A bacteria cultures continuously during growth, or at selected time points during growth, for example, by connecting a bioreactor to an alternating tangential flow (ATF) system (e.g., XCell ATF from Repligen). The ATF system retains intact cells (>0.22 um) in the bioreactor, and allows smaller components (e.g., EVs, free proteins) to pass through a filter for collection. For example, the system may be configured so that the <0.22 um filtrate is then passed through a second filter of 100 kDa, allowing species such as EVs between 0.22 um and 100 kDa to be collected, and species smaller than 100 kDa to be pumped back into the bioreactor. Alternatively, the system may be configured to allow for medium in the bioreactor to be replenished and/or modified during growth of the culture. EVs collected by this method may be further purified and/or concentrated by ultracentrifugation or filtration as described above for filtered supernatants.

EVs obtained by methods provided herein may be further purified by size-based column chromatography, by affinity chromatography, by ion-exchange chromatography, and by gradient ultracentrifugation, using methods that may include, but are not limited to, use of a sucrose gradient or Optiprep gradient. Briefly, using a sucrose gradient method, if ammonium sulfate precipitation or ultracentrifugation were used to concentrate the filtered supernatants, pellets are resuspended in 60% sucrose, 30 mM Tris, pH 8.0. If filtration was used to concentrate the filtered supernatant, the concentrate is buffer exchanged into 60% sucrose, 30 mM Tris, pH 8.0, using an Amicon Ultra column. Samples are applied to a 35-60% discontinuous sucrose gradient and centrifuged at 200,000×g for 3-24 hours at 4° C. Briefly, using an Optiprep gradient method, if ammonium sulfate precipitation or ultracentrifugation were used to concentrate the filtered supernatants, pellets are resuspended in PBS and 3 volumes of 60% Optiprep are added to the sample. In some embodiments, if filtration was used to concentrate the filtered supernatant, the concentrate is diluted using 60% Optiprep to a final concentration of 35% Optiprep. Samples are applied to a 0-45% discontinuous Optiprep gradient and centrifuged at 200,000×g for 3-24 hours at 4° C., e.g. 4-24 hours at 4° C.

In some embodiments, to confirm sterility and isolation of the EV preparations, EVs are serially diluted onto agar medium used for routine culture of the bacteria being tested, and incubated using routine conditions. Non-sterile preparations are passed through a 0.22 um filter to exclude intact cells. To further increase purity, isolated EVs may be DNase or proteinase K treated.

In some embodiments, for preparation of EVs used for in vivo injections, purified EVs are processed as described previously (G. Norheim, et al. PLoS ONE. 10(9): e0134353 (2015)). Briefly, after sucrose gradient centrifugation, bands containing EVs are resuspended to a final concentration of 50 μg/mL in a solution containing 3% sucrose or other solution suitable for in vivo injection known to one skilled in the art. This solution may also contain adjuvant, for example aluminum hydroxide at a concentration of 0-0.5% (w/v). In some embodiments, for preparation of EVs used for in vivo injections, EVs in PBS are sterile-filtered to <0.22 um.

In certain embodiments, to make samples compatible with further testing (e.g. to remove sucrose prior to TEM imaging or in vitro assays), samples are buffer exchanged into PBS or 30 mM Tris, pH 8.0 using filtration (e.g. Amicon Ultra columns), dialysis, or ultracentrifugation (200,000×g, ≥3 hours, 4° C.) and resuspension.

In some embodiments, the sterility of the EV preparations can be confirmed by plating a portion of the EVs onto agar medium used for standard culture of the bacteria used in the generation of the EVs and incubating using standard conditions.

In some embodiments select EVs are isolated and enriched by chromatography and binding surface moieties on EVs. In other embodiments, select EVs are isolated and/or enriched by fluorescent cell sorting by methods using affinity reagents, chemical dyes, recombinant proteins or other methods known to one skilled in the art.

Bacterial Compositions/Pharmaceutical Compositions

In certain aspects, provided herein are bacterial compositions comprising *Blautia* Strain A and/or a product of such bacteria (e.g., extracellular vesicles (EVs) and/or pharmaceutically active biomasses (PhABs)). In some embodiments, the *Blautia* Strain A is *Blautia* Strain A (ATCC Deposit Number PTA-125346). In some embodiments, the *Blautia* Strain A is a strain comprising at least 90%, at least 91%, at least 92%, at least 93%, at least 94%, at least 95%, at least 96%, at least 97%, at least 98%, or at least 99% sequence identity (e.g., at least 99.5% sequence identity, at least 99.6% sequence identity, at least 99.7% sequence identity, at least 99.8% sequence identity, at least 99.9% sequence identity) to the nucleotide sequence of the *Blautia* Strain A. In some embodiments, the bacterial formulation comprises a bacterium and/or a combination of bacteria described herein and a pharmaceutically acceptable carrier (e.g., a pharmaceutical composition).

In certain embodiments, at least 50%, 55%, 60%, 65%, 70%, 75%, 80%, 85%, 90%, 91%, 92%, 93%, 94%, 95%, 96%, 97%, 98% or 99% of the bacteria in the bacterial composition are *Blautia* Strain A. In certain embodiments, substantially all of the bacteria in the bacterial composition are *Blautia* Strain A. In certain embodiments, the bacterial composition comprises at least $1 \times 10^3$ colony forming units (CFUs), $1 \times 10^4$ colony forming units (CFUs), $1 \times 10^5$ colony forming units (CFUs), $5 \times 10^5$ colony forming units (CFUs), $1 \times 10^6$ colony forming units (CFUs), $2 \times 10^6$ colony forming units (CFUs), $3 \times 10^6$ colony forming units (CFUs), $4 \times 10^6$ colony forming units (CFUs), $5 \times 10^6$ colony forming units (CFUs), $6 \times 10^6$ colony forming units (CFUs), $7 \times 10^6$ colony forming units (CFUs), $8 \times 10^6$ colony forming units (CFUs), $9 \times 10^6$ colony forming units (CFUs), $1 \times 10^7$ colony forming units (CFUs), $2 \times 10^7$ colony forming units (CFUs), $3 \times 10^7$ colony forming units (CFUs), $4 \times 10^7$ colony forming units (CFUs), $5 \times 10^7$ colony forming units (CFUs), $6 \times 10^7$ colony forming units (CFUs), $7 \times 10^7$ colony forming units (CFUs), $8 \times 10^7$ colony forming units (CFUs), $9 \times 10^7$ colony forming units (CFUs), $1 \times 10^8$ colony forming units (CFUs), $2 \times 10^8$ colony forming units (CFUs), $3 \times 10^8$ colony forming units (CFUs), $4 \times 10^8$ colony forming units (CFUs), $5 \times 10^8$ colony forming units (CFUs), $6 \times 10^8$ colony forming units (CFUs), $7 \times 10^8$ colony forming units (CFUs), $8 \times 10^8$ colony forming units (CFUs), 9×10$^8$ colony forming units (CFUs), 1×10$^9$ colony forming units (CFUs), 5×10$^9$ colony forming units (CFUs), 1×10$^{10}$ colony forming units (CFUs) 5×10$^{10}$ colony forming units (CFUs), 1×10$^{11}$ colony forming units (CFUs) 5×10$^{11}$ colony forming units (CFUs), 1×10$^{12}$ colony forming units (CFUs) 5×10$^{12}$ colony forming units (CFUs), 1×10$^{13}$ colony forming units (CFUs) of *Blautia* Strain A.

In some embodiments, at least 10%, 15%, 20%, 25%, 30%, 35%, 40%, 45%, 50%, 55%, 60%, 65%, 70%, 75%, 80%, 85%, 90%, 95%, 96%, 97%, 98% or 99% of the bacteria in the composition are selected from among the bacterial species described herein. 10%, 15%, 20%, 25%, 30%, 35%, 40%, 45%, 50%, 55%, 60%, 65%, 70%, 75%, 80%, 85%, 90%, 95%, 96%, 97%, 98% or 99% of the bacteria in the composition are selected from among the bacterial strains described herein.

In some embodiments, the compositions described herein may include only one species of bacteria described herein or may include two or more species of the bacteria described herein. For example, 1, 2, 3, 4, 5, 6, 7, 8, 9, 10, 11, 12, 13, 14, 15, 16, 17, 18, 19 or 20 of the species described herein, in any combination, can be included in the compositions provided herein.

In some embodiments, the bacterial composition comprises a killed bacterium, a live bacterium and/or an attenuated bacterium. Bacteria may be heat-killed by pasteurization, sterilization, high temperature treatment, spray cooking and/or spray drying (heat treatments can be performed at 50° C., 65° C., 85° C. or a variety of other temperatures and/or a varied amount of time). Bacteria may also be killed or inactivated using γ-irradiation (gamma irradiation), exposure to UV light, formalin-inactivation, and/or freezing methods, or a combination thereof. For example, the bacteria may be exposed to 1, 2, 3, 4, 5, 10, 15, 20, 25, 30, 35, 40, or 50 kGy of radiation prior to administration. In some embodiments, bacteria (e.g., *Blautia* Strain A) are killed using gamma irradiation. In some embodiments, the bacteria are killed or inactivated using electron irradiation (e.g., beta radiation) or x-ray irradiation.

Bacteria may be grown to various growth phases and tested for efficacy at different dilutions and at different points during the growth phase. For example, bacteria may be tested for efficacy following administration at stationary phase (including early or late stationary phase), or at various timepoints during exponential phase. In addition to inactivation by various methods, bacteria may be tested for efficacy using different ratios of live versus inactivated cells, or different ratios of cells at various growth phases.

In certain embodiments, provided herein are pharmaceutical compositions comprising *Blautia* Strain A EVs and/or *Blautia* Strain A bacteria provided herein (e.g., an EV composition). In some embodiments, the EV composition comprises an EV and/or a combination of EVs described herein and a pharmaceutically acceptable carrier.

In some embodiments, the pharmaceutical compositions comprise *Blautia* Strain A EVs substantially or entirely free of bacteria. In some embodiments, the pharmaceutical compositions comprise both *Blautia* Strain A EVs and whole *Blautia* Strain A bacteria (e.g., live bacteria, killed bacteria, attenuated bacteria). In certain embodiments, the pharmaceutical compositions comprise *Blautia* Strain A bacteria that is substantially or entirely free of EVs.

In some embodiments, the pharmaceutical composition comprises at least 1 *Blautia* Strain A bacterium for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, 1×10$^3$, 2×10$^3$, 3×10$^3$, 4×10$^3$, 5×10$^3$, 6×10$^3$, 7×10$^3$, 8×10$^3$, 9×10$^3$, 1×10$^4$, 2×10$^4$, 3×10$^4$, 4×10$^4$, 5×10$^4$, 6×10$^4$, 7×10$^4$, 8×10$^4$, 9×10$^4$, 1×10$^5$, 2×10$^5$, 3×10$^5$, 4×10$^5$, 5×10$^5$, 6×10$^5$, 7×10$^5$, 8×10$^5$, 9×10$^5$, 1×10$^6$, 2×10$^6$, 3×10$^6$, 4×10$^6$, 5×10$^6$, 6×10$^6$, 7×10$^6$, 8×10$^6$, 9×10$^6$, 1×10$^7$, 2×10$^7$, 3×10$^7$, 4×10$^7$, 5×10$^7$, 6×10$^7$, 7×10$^7$, 8×10$^7$, 9×10$^7$, 1×10$^8$, 2×10$^8$, 3×10$^8$, 4×10$^8$, 5×10$^8$, 6×10$^8$, 7×10$^8$, 8×10, 9×10$^8$, 1×10$^9$, 2×10$^9$, 3×10$^9$, 4×10$^9$, 5×10$^9$, 6×10$^9$, 7×10$^9$, 8×10$^9$, 9×10$^9$, 1×10$^{10}$, 2×10$^{10}$, 3×10$^{10}$, 4×10$^{10}$, 5×10$^{10}$ 6×10$^{10}$, 7×10$^{10}$, 8×10$^{10}$, 9×10$^{10}$, 1×10$^{11}$, 2×10$^{11}$, 3×10$^{11}$, 4×10$^{11}$, 5×10$^{11}$, 6×10$^{11}$, 7×10$^{11}$, 8×10$^{11}$, 9×10$^{11}$, and/or 1×10$^{12}$ *Blautia* Strain A EV particles.

In some embodiments, the pharmaceutical composition comprises about 1 *Blautia* Strain A bacterium for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, 1×10$^3$, 2×10$^3$, 3×10$^3$, 4×10$^3$, 5×10$^3$, 6×10$^3$, 7×10$^3$, 8×10$^3$, 9×10$^3$, 1×10$^4$, 2×10$^4$, 3×10$^4$, 4×10$^4$, 5×10$^4$, 6×10$^4$, 7×10$^4$, 8×10$^4$, 9×10$^4$, 1×10$^5$, 2×10$^5$, 3×10$^5$, 4×10$^5$, 5×10$^5$, 6×10$^5$, 7×10$^5$, 8×10$^5$, 9×10$^5$, 1×10$^6$, 2×10$^6$, 3×10$^6$, 4×10$^6$, 5×10$^6$, 6×10$^6$, 7×10$^6$, 8×10$^6$, 9×10$^6$, 1×10$^7$, 2×10$^7$, 3×10$^7$, 4×10$^7$, 5×10$^7$, 6×10$^7$, 7×10$^7$, 8×10$^7$, 9×10$^7$, 1×10$^8$, 2×10$^8$, 3×10$^8$, 4×10$^8$, 5×10$^8$, 6×10$^8$, 7×10$^8$, 8×10$^8$, 9×10, 1×10$^9$, 2×10$^9$, 3×10$^9$, 4×10$^9$, 5×10$^9$, 6×10$^9$, 7×10$^9$, 8×10$^9$, 9×10$^9$, 1×10$^{10}$, 2×10$^{10}$, 3×10$^{10}$, 4×10$^{10}$, 5×10$^{10}$, 6×10$^{10}$, 7×10$^{10}$ 8×10$^{10}$, 9×10$^{10}$, 1×10$^{11}$, 2×10$^{11}$, 3×10$^{11}$, 4×10$^{11}$, 5×10$^{11}$, 6×10$^{11}$, 7×10$^{11}$, 8×10$^{11}$, 9×10$^{11}$, and/or 1×10$^{12}$ *Blautia* Strain A EV particles.

In certain embodiments, the pharmaceutical composition comprises a certain ratio of *Blautia* Strain A bacteria particles to *Blautia* Strain A EV particles. The number of *Blautia* Strain A bacteria particles can be based on actual particle number or (if the bacteria is live) the number of CFUs. The particle number can be established by combining a set number of purified *Blautia* Strain A EVs with a set number of purified *Blautia* Strain A bacterium, by modifying the growth conditions under which the *Blautia* Strain A bacteria are cultured, or by modifying the *Blautia* Strain A bacteria itself to produce more or fewer *Blautia* Strain A EVs.

In some embodiments, to quantify the numbers of *Blautia* Strain A EVs and/or *Blautia* Strain A bacteria present in a bacterial sample, electron microscopy (e.g., EM of ultrathin frozen sections) can be used to visualize the vesicles and bacteria and count their relative numbers. Alternatively, combinations of nanoparticle tracking analysis (NTA), Coulter counting, and dynamic light scattering (DLS) or a combination of these techniques can be used. NTA and the Coulter counter count particles and show their sizes. DLS gives the size distribution of particles, but not the concentration. Bacteria frequently have diameters of 1-2 um. The full range is 0.2-20 um. Combined results from Coulter counting and NTA can reveal the numbers of bacteria in a given sample. Coulter counting reveals the numbers of particles with diameters of 0.7-10 um. NTA reveals the numbers of particles with diameters of 50-1400 nm. For most bacterial samples, the Coulter counter alone can reveal the number of bacteria in a sample. EVs are 20-250 nm in diameter. NTA will allow us to count the numbers of particles that are 50-250 nm in diameter. DLS reveals the distribution of particles of different diameters within an approximate range of 1 nm-3 um.

In some embodiments, the pharmaceutical composition comprises no more than 1 Blautia Strain A bacterium for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$ $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ Blautia Strain A EV particles.

In some embodiments, the pharmaceutical composition comprises at least 1 Blautia Strain A EV particle for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$ $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ Blautia Strain A bacterium.

In some embodiments, the pharmaceutical composition comprises about 1 Blautia Strain A EV particle for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$ $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ Blautia Strain A bacterium. In some embodiments, the pharmaceutical composition comprises no more than 1 Blautia Strain A EV particle for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$ $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ Blautia Strain A bacterium.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are *Blautia* Strain A EVs.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are *Blautia* Strain A bacteria.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are *Blautia* Strain A EVs.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are *Blautia* Strain A bacteria.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22, 23%, 24%, 25%, 26, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are *Blautia* Strain A EVs.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are *Blautia* Strain A bacteria.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is *Blautia* Strain A EV protein.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is *Blautia* Strain A bacteria protein.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is *Blautia* Strain A EV protein.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is *Blautia* Strain A bacteria protein.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is *Blautia* Strain A EV protein.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is *Blautia* Strain A bacteria protein.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are *Blautia* Strain A EV lipids.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are *Blautia* Strain A bacteria lipids.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are *Blautia* Strain A EV lipids.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are *Blautia* Strain A bacteria lipids.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are *Blautia* Strain A EV lipids.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are *Blautia* Strain A bacteria lipids.

In some embodiments, the *Blautia* Strain A EVs in the pharmaceutical composition are purified from one or more other bacterial components. In some embodiments, the pharmaceutical composition further comprises other bacterial components. In some embodiments, the pharmaceutical composition comprise bacteria cells.

As described in detail below, the pharmaceutical compositions disclosed herein may be specially formulated for administration in solid or liquid form, including those adapted for oral or rectal administration.

In some embodiments, the composition described herein may be a pharmaceutical composition, a dietary supplement, or a food product (e.g., a food or beverage). In some embodiments, the food product is an animal feed.

In certain embodiments, the pharmaceutical composition for oral administration described herein comprises an additional component that enables efficient delivery of the bacteria to the colon. In some embodiments, pharmaceutical preparation that enables the delivery of the bacteria to the colon can be used. Examples of such formulations include pH sensitive compositions, such as buffered sachet formulations or enteric polymers that release their contents when the pH becomes alkaline after the enteric polymers pass through the stomach. When a pH sensitive composition is used for formulating the pharmaceutical preparation, the pH sensitive composition can be a polymer whose pH threshold of the decomposition of the composition is between about 6.8 and about 7.5.

Another embodiment of a pharmaceutical composition useful for delivery of the bacteria to the colon is one that ensures the delivery to the colon by delaying the release of the bacteria by approximately 3 to 5 hours, which corresponds to the small intestinal transit time. In some embodiments, the pharmaceutical composition for delayed release includes a hydrogel shell. The hydrogel is hydrated and swells upon contact with gastrointestinal fluid, with the result that the contents are effectively released (released predominantly in the colon). Delayed release dosage units include bacteria-containing compositions having a material which coats or selectively coats the bacteria. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Examples of composition enabling the delivery to the colon further include bioadhesive compositions which specifically adhere to the colonic mucosal membrane (for example, a polymer described in the specification of U.S. Pat. No. 6,368,586, hereby incorporated by reference) and compositions into which a protease inhibitor is incorporated for protecting particularly a biopharmaceutical preparation in the gastrointestinal tracts from decomposition due to an activity of a protease.

An example of a system enabling the delivery to the colon is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

Another example of the system enabling the delivery to the colon is a system of delivering a composition to the colon, the system being specifically decomposed by an enzyme (for example, a carbohydrate hydrolase or a carbohydrate reductase) present in the colon. Such a system is not particularly limited, and more specific examples thereof include systems which use food components such as non-starch polysaccharides, amylose, xanthan gum, and azopolymers.

In some embodiments, Probiotic formulations containing *Blautia* Strain A are provided as encapsulated, enteric coated, or powder forms, with doses ranging up to $10^{11}$ cfu (e.g., up to $10^{10}$ cfu). In some embodiments, the composition comprises $5 \times 10^{11}$ cfu of *Blautia* Strain A and 10% (w/w) corn starch in a capsule. The capsule is enteric coated for duodenal release at pH5.5 In some embodiments, the capsule is enteric coated for duodenal release at pH 5.5. In some embodiments, the composition comprises a powder of freeze-dried *Blautia* Strain A which is deemed "Qualified Presumption of Safety" (QPS) status. In some embodiments, the composition is stable at frozen or refrigerated temperature.

Methods for producing microbial compositions may include three main processing steps. The steps are: organism banking, organism production, and preservation. In certain embodiments, a sample that contains an abundance of *Blautia* Strain A may be cultured by avoiding an isolation step.

For banking, the strains included in the microbial composition may be (1) isolated directly from a specimen or taken from a banked stock, (2) optionally cultured on a nutrient agar or broth that supports growth to generate viable biomass, and (3) the biomass optionally preserved in multiple aliquots in long-term storage.

In embodiments using a culturing step, the agar or broth may contain nutrients that provide essential elements and specific factors that enable growth. An example would be a medium composed of 20 g/L glucose, 10 g/L yeast extract, 10 g/L soy peptone, 2 g/L citric acid, 1.5 g/L sodium phosphate monobasic, 100 mg/L ferric ammonium citrate, 80 mg/L magnesium sulfate, 10 mg/L hemin chloride, 2 mg/L calcium chloride, 1 mg/L menadione. Another example would be a medium composed of 10 g/L beef extract, 10 g/L peptone, 5 g/L sodium chloride, 5 g/L dextrose, 3 g/L yeast extract, 3 g/L sodium acetate, 1 g/L soluble starch, and 0.5 g/L L-cysteine HCl, at pH 6.8. A variety of microbiological media and variations are well known in the art (e.g., R. M. Atlas, *Handbook of Microbiological Media* (2010) CRC Press). Culture media can be added to the culture at the start, may be added during the culture, or may be intermittently/continuously flowed through the culture. The strains in the bacterial composition may be cultivated alone, as a subset of the microbial composition, or as an entire collection comprising the microbial composition. As an example, a first strain may be cultivated together with a second strain in a mixed continuous culture, at a dilution rate lower than the maximum growth rate of either cell to prevent the culture from washing out of the cultivation.

The inoculated culture is incubated under favorable conditions for a time sufficient to build biomass. For microbial compositions for human use this is often at 37° C. temperature, pH, and other parameter with values similar to the normal human niche. The environment may be actively controlled, passively controlled (e.g., via buffers), or allowed to drift. For example, for anaerobic bacterial compositions, an anoxic/reducing environment may be employed. This can be accomplished by addition of reducing agents such as cysteine to the broth, and/or stripping it of oxygen. As an example, a culture of a bacterial composition may be grown at 37° C., pH 7, in the medium above, pre-reduced with 1 g/L cysteine-HCl.

When the culture has generated sufficient biomass, it may be preserved for banking. The organisms may be placed into a chemical milieu that protects from freezing (adding 'cryoprotectants'), drying ('lyoprotectants'), and/or osmotic shock ('osmoprotectants'), dispensing into multiple (optionally identical) containers to create a uniform bank, and then treating the culture for preservation. Containers are generally impermeable and have closures that assure isolation from the environment. Cryopreservation treatment is accomplished by freezing a liquid at ultra-low temperatures (e.g., at or below −80° C.). Dried preservation removes water from the culture by evaporation (in the case of spray drying or 'cool drying') or by sublimation (e.g., for freeze drying, spray freeze drying). Removal of water improves long-term microbial composition storage stability at temperatures elevated above cryogenic conditions. If the microbial composition comprises, for example, spore forming species and results in the production of spores, the final composition may be purified by additional means such as density gradient centrifugation and preserved using the techniques [?]described above[?]. Microbial composition banking may be done by culturing and preserving the strains individually, or by mixing the strains together to create a combined bank. As an example of cryopreservation, a microbial composition culture may be harvested by centrifugation to pellet the cells from the culture medium, the supernatant decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

Microbial production may be conducted using similar culture steps to banking, including medium composition and culture conditions described above. It may be conducted at larger scales of operation, especially for clinical development or commercial production. At larger scales, there may be several subcultivations of the microbial composition prior to the final cultivation. At the end of cultivation, the culture is harvested to enable further formulation into a dosage form for administration. This can involve concentration, removal of undesirable medium components, and/or introduction into a chemical milieu that preserves the microbial composition and renders it acceptable for administration via the chosen route. For example, a microbial composition may be cultivated to a concentration of $10^{10}$ CFU/mL, then concentrated 20-fold by tangential flow microfiltration; the spent medium may be exchanged by diafiltering with a preservative medium consisting of 2% gelatin, 100 mM trehalose, and 10 mM sodium phosphate buffer. The suspension can then be freeze-dried to a powder and titrated.

After drying, the powder may be blended to an appropriate potency, and mixed with other cultures and/or a filler such as microcrystalline cellulose for consistency and ease of handling, and the bacterial composition formulated as provided herein.

In certain aspects, provided are bacterial compositions for administration subjects. In some embodiments, the bacterial compositions are combined with additional active and/or inactive materials in order to produce a final product, which may be in single dosage unit or in a multi-dose format.

In some embodiments, the composition comprises at least one carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replaced with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

In some embodiments, the composition comprises at least one lipid. As used herein, a "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0). In some embodiments the composition comprises at least one modified lipid, for example a lipid that has been modified by cooking.

In some embodiments, the composition comprises at least one supplemental mineral or mineral source. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In some embodiments, the composition comprises at least one supplemental vitamin. The at least one vitamin can be fat-soluble or water soluble vitamins. Suitable vitamins include but are not limited to vitamin C, vitamin A, vitamin E, vitamin B 12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

In some embodiments, the composition comprises an excipient. Non-limiting examples of suitable excipients include a buffering agent, a preservative, a stabilizer, a binder, a compaction agent, a lubricant, a dispersion enhancer, a disintegration agent, a flavoring agent, a sweetener, and a coloring agent.

In some embodiments, the excipient is a buffering agent. Non-limiting examples of suitable buffering agents include sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In some embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof.

In some embodiments, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments, the composition comprises a dispersion enhancer as an excipient. Non-limiting examples of suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments, the composition comprises a disintegrant as an excipient. In some embodiments the disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. In some embodiments the disintegrant is an effervescent disintegrant. Non-limiting examples of suitable effervescent disintegrants include sodium bicarbonate in combination with citric acid, and sodium bicarbonate in combination with tartaric acid.

In some embodiments, the bacterial formulation comprises an enteric coating or micro encapsulation. In certain embodiments, the enteric coating or micro encapsulation improves targeting to a desired region of the gastrointestinal tract. For example, in certain embodiments, the bacterial composition comprises an enteric coating and/or microcapsules that dissolves at a pH associated with a particular region of the gastrointestinal tract. In some embodiments, the enteric coating and/or microcapsules dissolve at a pH of about 5.5-6.2 to release in the duodenum, at a pH value of about 7.2-7.5 to release in the ileum, and/or at a pH value of about 5.6-6.2 to release in the colon. Exemplary enteric coatings and microcapsules are described, for example, in U.S. Pat. Pub. No. 2016/0022592, which is hereby incorporated by reference in its entirety.

In some embodiments, the composition is a food product (e.g., a food or beverage) such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed. Specific examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, and Chinese soups; soups; dairy products such as milk, dairy beverages, ice creams, cheeses, and yogurts; fermented products such as fermented soybean pastes, yogurts, fermented beverages, and pickles; bean products; various confectionery products, including biscuits, cookies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies.

In certain embodiments, the bacteria disclosed herein are administered in conjunction with a prebiotic to the subject. Prebiotics are carbohydrates which are generally indigestible by a host animal and are selectively fermented or metabolized by bacteria. Prebiotics may be short-chain carbohydrates (e.g., oligosaccharides) and/or simple sugars (e.g., mono- and di-saccharides) and/or mucins (heavily glycosylated proteins) that alter the composition or metabolism of a microbiome in the host. The short chain carbohydrates are also referred to as oligosaccharides, and usually contain from 2 or 3 and up to 8, 9, 10, 15 or more sugar moieties. When prebiotics are introduced to a host, the prebiotics affect the bacteria within the host and do not directly affect the host. In certain aspects, a prebiotic composition can selectively stimulate the growth and/or activity of one of a limited number of bacteria in a host. Prebiotics include oligosaccharides such as fructooligosaccharides (FOS) (including inulin), galactooligosaccharides (GOS), trans-galactooligosaccharides, xylooligosaccharides (XOS), chitooligosaccharides (COS), soy oligosaccharides (e.g., stachyose and raffinose) gentiooligosaccharides, isomaltooligosaccharides, mannooligosaccharides, maltooligosaccharides and mannanoligosaccharides. Oligosaccharides are not necessarily single components, and can be mixtures containing oligosaccharides with different degrees of oligomerization, sometimes including the parent disaccharide and the monomeric sugars. Various types of oligosaccharides are found as natural components in many common foods, including fruits, vegetables, milk, and honey. Specific examples of oligosaccharides are lactulose, lactosucrose, palatinose, glycosyl sucrose, guar gum, gum Arabic, tagalose, amylose, amylopectin, pectin, xylan, and cyclodextrins. Prebiotics may also be purified or chemically or enzymatically synthesized.

Production of PhABs

In certain aspects, the PhABs described herein can be prepared using any method known in the art.

In some embodiments, the PhABs described herein are prepared by fractionation. Bacterial cells and/or supernatants from cultured bacteria cells are fractionated into various pharmacologically active biomass (PhABs) and/or products derived therefrom. Bacterial cells and/or supernatants are fractionated using materials and methods known in the art (see e.g. Sandrini et al. Fractionation by ultracentrifugation of gram negative cytoplasmic and membrane proteins. 2014. Bio-Protocol. 4(21); Scholler et al. Protoplast and cytoplasmic membrane preparations from *Streptococcus sanguis* and *Streptococcus mutans*. 1983. J Gen Micro. 129: 3271-3279; Thein et al. Efficient subfractionation of gram-negative bacteria for proteomics studies. 2010. Am Chem Society. 9: 6135-6147; Hobb et al. Evaluation of procedures for outer membrane isolation from Campylobacterjejuni. 2009. 155(Pt. 3): 979-988).

Additionally, PhABs obtained by methods provided herein may be further purified by size based column chromatography, by affinity chromatography, and by gradient ultracentrifugation, using methods that may include, but are not limited to, use of a sucrose gradient or Optiprep gradient. Briefly, using a sucrose gradient method, if ammonium sulfate precipitation or ultracentrifugation were used to concentrate the filtered supernatants, pellets are resuspended in 60% sucrose, 30 mM Tris, pH 8.0. If filtration was used to concentrate the filtered supernatant, the concentrate is buffer exchanged into 60% sucrose, 30 mM Tris, pH 8.0, using an Amicon Ultra column. Samples are applied to a 35-60% discontinuous sucrose gradient and centrifuged at 200,000×g for 3-24 hours at 4° C. Briefly, using an Optiprep gradient method, if ammonium sulfate precipitation or ultracentrifugation were used to concentrate the filtered supernatants, pellets are resuspended in 35% Optiprep in PBS. In some embodiments, if filtration was used to concentrate the filtered supernatant, the concentrate is diluted using 60% Optiprep to a final concentration of 35% Optiprep. Samples are applied to a 35-60% discontinuous sucrose gradient and centrifuged at 200,000×g for 3-24 hours at 4° C.

In some embodiments, to confirm sterility and isolation of the PhAB preparations, PhABs are serially diluted onto agar medium used for routine culture of the bacteria being tested, and incubated using routine conditions. Non-sterile preparations are passed through a 0.22 um filter to exclude intact cells. To further increase purity, isolated PhABs may be DNase or proteinase K treated.

In some embodiments, for preparation of PhABs used for in vivo injections, purified PhABs are processed as described previously (G. Norheim, et al. PLoS ONE. 10(9): e0134353 (2015)). Briefly, after sucrose gradient centrifugation, bands containing PhABs are resuspended to a final concentration of 50 µg/mL in a solution containing 3% sucrose or other solution suitable for in vivo injection known to one skilled in the art. This solution may also contain adjuvant, for example aluminum hydroxide at a concentration of 0-0.5% (w/v).

In certain embodiments, to make samples compatible with further testing (e.g. to remove sucrose prior to TEM imaging or in vitro assays), samples are buffer exchanged into PBS or 30 mM Tris, pH 8.0 using filtration (e.g. Amicon Ultra columns), dialysis, or ultracentrifugation (200,000×g, ≥3 hours, 4° C.) and resuspension.

In some embodiments, the sterility of the PhAB preparations can be confirmed by plating a portion of the PhABs onto agar medium used for standard culture of the bacteria used in the generation of the PhABs and incubating using standard conditions.

In some embodiments select PhABs are isolated and enriched by chromatography and binding surface moieties on PhABs. In other embodiments, select PhABs are isolated and/or enriched by fluorescent cell sorting by methods using affinity reagents, chemical dyes, recombinant proteins or other methods known to one skilled in the art.

Administration

In certain aspects, provided herein is a method of delivering a bacterium and/or a bacterial composition described herein to a subject. In some embodiments of the methods provided herein, the bacteria are administered in conjunction with the administration of an additional therapeutic. In some embodiments, the bacteria is co-formulated in a pharmaceutical composition with the additional therapeutic. In some embodiments, the bacteria is co-administered with the additional therapeutic. In some embodiments, the additional therapeutic is administered to the subject before administration of the bacteria (e.g., about 1, 2, 3, 4, 5, 6, 7, 8, 9, 10, 15, 20, 25, 30, 35, 40, 45, 50 or 55 minutes before, about 1, 2, 3, 4, 5, 6, 7, 8, 9, 10, 11, 12, 13, 14, 15, 16, 17, 18, 19, 20, 21, 22 or 23 hours before, or about 1, 2, 3, 4, 5, 6, 7, 8, 9, 10, 11, 12, 13 or 14 days before). In some embodiments, the additional therapeutic is administered to the subject after administration of the bacteria (e.g., about 1, 2, 3, 4, 5, 6, 7, 8, 9, 10, 15, 20, 25, 30, 35, 40, 45, 50 or 55 minutes after, about 1, 2, 3, 4, 5, 6, 7, 8, 9, 10, 11, 12, 13, 14, 15, 16, 17, 18, 19, 20, 21, 22 or 23 hours after, or about 1, 2, 3, 4, 5, 6, 7, 8, 9, 10, 11, 12, 13 or 14 days after). In some embodiments, the same mode of delivery is used to deliver both the bacteria and the additional therapeutic. In some embodiments different modes of delivery are used to administer the bacteria and the additional therapeutic. For example, in some embodiments, the bacteria is administered orally while the additional therapeutic is administered via injection (e.g., an intravenous, intramuscular and/or intratumoral injection).

In certain embodiments, the pharmaceutical compositions, dosage forms, and kits described herein can be administered in conjunction with any other conventional anti-immune disorder treatment. These treatments may be applied as necessary and/or as indicated and may occur before, concurrent with or after administration of the pharmaceutical compositions, dosage forms, and kits described herein.

The dosage regimen can be any of a variety of methods and amounts, and can be determined by one skilled in the art according to known clinical factors. As is known in the medical arts, dosages for any one patient can depend on many factors, including the subject's species, size, body surface area, age, sex, immunocompetence, and general health, the particular microorganism to be administered, duration and route of administration, the kind and stage of the disease, for example, tumor size, and other compounds such as drugs being administered concurrently. In addition to the above factors, such levels can be affected by the infectivity of the microorganism, and the nature of the microorganism, as can be determined by one skilled in the art. In the present methods, appropriate minimum dosage levels of microorganisms can be levels sufficient for the microorganism to survive, grow and replicate. The methods of treatment described herein may be suitable for the treatment of an immune disorder (e.g., an autoimmune disease, an inflammatory disease, an allergy). The dose of the pharmaceutical compositions described herein may be appropriately set or adjusted in accordance with the dosage form, the route of administration, the degree or stage of a target disease, and the like. For example, the general effective dose of the agents may range between 0.01 mg/kg body weight/day and 1000 mg/kg body weight/day, between 0.1 mg/kg body weight/day and 1000 mg/kg body weight/day, 0.5 mg/kg body weight/day and 500 mg/kg body weight/day, 1 mg/kg body weight/day and 100 mg/kg body weight/day, or between 5 mg/kg body weight/day and 50 mg/kg body weight/day. The effective dose may be 0.01, 0.05, 0.1, 0.5, 1, 2, 3, 5, 10, 20, 30, 40, 50, 60, 70, 80, 90, 100, 200, 500, or 1000 mg/kg body weight/day or more, but the dose is not limited thereto.

In some embodiments, the dose administered to a subject is sufficient to prevent the immune disorder, delay its onset, or slow or stop its progression or prevent a relapse of the immune disorder. One skilled in the art will recognize that dosage will depend upon a variety of factors including the strength of the particular compound employed, as well as the age, species, condition, and body weight of the subject. The size of the dose will also be determined by the route, timing, and frequency of administration as well as the existence, nature, and extent of any adverse side-effects that might accompany the administration of a particular compound and the desired physiological effect.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. An effective dosage and treatment protocol can be determined by routine and conventional means, starting e.g., with a low dose in laboratory animals and then increasing the dosage while monitoring the effects, and systematically varying the dosage regimen as well. Animal studies are commonly used to determine the maximal tolerable dose ("MTD") of bioactive agent per kilogram weight. Those skilled in the art regularly extrapolate doses for efficacy, while avoiding toxicity, in other species, including humans.

In accordance with the above, in therapeutic applications, the dosages of the active agents used in accordance with the invention vary depending on the active agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the advancement of an immune disorder.

Separate administrations can include any number of two or more administrations (e.g., doses), including two, three, four, five or six administrations. One skilled in the art can readily determine the number of administrations to perform, or the desirability of performing one or more additional administrations, according to methods known in the art for monitoring therapeutic methods and other monitoring methods provided herein. In some embodiments, the doses may be separated by at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days or 1, 2, 3, or 4 weeks. Accordingly, the methods provided herein include methods of providing to the subject one or more administrations of a bacterium, where the number of administrations can be determined by monitoring the subject, and, based on the results of the monitoring, determining whether or not to provide one or more additional administrations. Deciding on whether or not to provide one or more additional administrations can be based on a variety of monitoring results, including, but not limited to, indication of tumor growth or inhibition of tumor growth, appearance of new metastases or inhibition of metastasis, the subject's anti-bacterium antibody titer, the subject's anti-tumor antibody titer, the overall health of the subject and/or the weight of the subject.

The time period between administrations can be any of a variety of time periods. The time period between administrations can be a function of any of a variety of factors, including monitoring steps, as described in relation to the number of administrations, the time period for a subject to mount an immune response and/or the time period for a subject to clear the bacteria from normal tissue. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for a subject to clear the bacteria from normal tissue; for example, the time period can be more than the time period for a subject to clear the bacteria from normal tissue, such as more than about a day, more than about two days, more than about three days, more than about five days, or more than about a week.

In some embodiments, the delivery of an immune disorder therapeutic in combination with the bacteria described herein reduces the adverse effects and/or improves the efficacy of the immune disorder therapeutic.

The effective dose of an immune disorder therapeutic described herein is the amount of the therapeutic agent that is effective to achieve the desired therapeutic response for a particular patient, composition, and mode of administration, with the least toxicity to the patient. The effective dosage level can be identified using the methods described herein and will depend upon a variety of pharmacokinetic factors including the activity of the particular compositions administered, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. In general, an effective dose of an immune disorder therapy will be the amount of the therapeutic agent, which is the lowest dose effective to produce a therapeutic effect. Such an effective dose will generally depend upon the factors described above.

The toxicity of an immune disorder therapy is the level of adverse effects experienced by the subject during and following treatment. Adverse events associated with immune disorder therapy toxicity include, but are not limited to, abdominal pain, acid indigestion, acid reflux, allergic reactions, alopecia, anaphylaxis, anemia, anxiety, lack of appetite, arthralgias, asthenia, ataxia, azotemia, loss of balance, bone pain, bleeding, blood clots, low blood pressure, elevated blood pressure, difficulty breathing, bronchitis, bruising, low white blood cell count, low red blood cell count, low platelet count, cardiotoxicity, cystitis, hemorrhagic cystitis, arrhythmias, heart valve disease, cardiomyopathy, coronary artery disease, cataracts, central neurotoxicity, cognitive impairment, confusion, conjunctivitis, constipation, coughing, cramping, cystitis, deep vein thrombosis, dehydration, depression, diarrhea, dizziness, dry mouth, dry skin, dyspepsia, dyspnea, edema, electrolyte imbalance, esophagitis, fatigue, loss of fertility, fever, flatulence, flushing, gastric reflux, gastroesophageal reflux disease, genital pain, granulocytopenia, gynecomastia, glaucoma, hair loss, hand-foot syndrome, headache, hearing loss, heart failure, heart palpitations, heartburn, hematoma, hemorrhagic cystitis, hepatotoxicity, hyperamylasemia, hypercalcemia, hyperchloremia, hyperglycemia, hyperkalemia, hyperlipasemia, hypermagnesemia, hypernatremia, hyperphosphatemia, hyperpigmentation, hypertriglyceridemia, hyperuricemia, hypoalbuminemia, hypocalcemia, hypochloremia, hypoglycemia, hypokalemia, hypomagnesemia, hyponatremia, hypophosphatemia, impotence, infection, injection site reactions, insomnia, iron deficiency, itching, joint pain, kidney failure, leukopenia, liver dysfunction, memory loss, menopause, mouth sores, mucositis, muscle pain, myalgias, myelosuppression, myocarditis, neutropenic fever, nausea, nephrotoxicity, neutropenia, nosebleeds, numbness, ototoxicity, pain, palmar-plantar erythrodysesthesia, pancytopenia, pericarditis, peripheral neuropathy, pharyngitis, photophobia, photosensitivity, pneumonia, pneumonitis, proteinuria, pulmonary embolus, pulmonary fibrosis, pulmonary toxicity, rash, rapid heart beat, rectal bleeding, restlessness, rhinitis, seizures, shortness of breath, sinusitis, thrombocytopenia, tinnitus, urinary tract infection, vaginal bleeding, vaginal dryness, vertigo, water retention, weakness, weight loss, weight gain, and xerostomia. In general, toxicity is acceptable if the benefits to the subject achieved through the therapy outweigh the adverse events experienced by the subject due to the therapy.

In some embodiments, the administration of the bacterial composition treats the immune disorder.

Therapeutic Agents

In certain aspects, the methods provided herein include the administration to a subject of a bacterium and/or a bacterial composition described herein (e.g., a *Blautia* Strain A-containing bacterial composition) either alone or in combination with another therapeutic. In some embodiments, the bacterial composition and the other therapy can be administered to the subject in any order. In some embodiments, the bacterial composition and the other therapy are administered conjointly.

In some embodiments the bacterium is administered to the subject before the additional therapeutic is administered (e.g., at least 1, 2, 3, 4, 5, 6, 7, 8, 9, 10, 11, 12, 13, 14, 15, 16, 17, 18, 19, 20, 21, 22, 23 or 24 hours before or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days before). In some embodiments the bacterium is administered to the subject after the additional therapeutic is administered (e.g., at least 1, 2, 3, 4, 5, 6, 7, 8, 9, 10, 11, 12, 13, 14, 15, 16, 17, 18, 19, 20, 21, 22, 23 or 24 hours after or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after). In some embodiments, the bacterium and the additional therapeutic are administered to the subject simultaneously or nearly simultaneously (e.g., administrations occur within an hour of each other). In some embodiments, the subject is administered an antibiotic before the bacterium is administered to the subject (e.g., at least 1, 2, 3, 4, 5, 6, 7, 8, 9, 10, 11, 12, 13, 14, 15, 16, 17, 18, 19, 20, 21, 22, 23 or 24 hours before or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days before). In some embodiments, the subject is administered an antibiotic after the bacterium is administered to the subject (e.g., at least 1, 2, 3, 4, 5, 6, 7, 8, 9, 10, 11, 12, 13, 14, 15, 16, 17, 18, 19, 20, 21, 22, 23 or 24 hours before or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after). In some embodiments, the bacterium and the antibiotic are administered to the subject simultaneously or nearly simultaneously (e.g., administrations occur within an hour of each other).

In certain embodiments, the subject may undergo surgery. Types of surgery include but are not limited to preventative, diagnostic or staging, curative and palliative surgery.

In some embodiments, the additional therapeutic is an antibiotic. For example, if the presence of a immune-disorder-associated bacteria and/or an immune-disorder-associated microbiome profile is detected according to the methods provided herein, antibiotics can be administered to eliminate the immune-disorder-associated bacteria from the subject. "Antibiotics" broadly refers to compounds capable of inhibiting or preventing a bacterial infection. Antibiotics can be classified in a number of ways, including their use for specific infections, their mechanism of action, their bioavailability, or their spectrum of target microbe (e.g., Gram-negative vs. Gram-positive bacteria, aerobic vs. anaerobic bacteria, etc.) and these may be used to kill specific bacteria in specific areas of the host ("niches") (Leekha, et al 2011. General Principles of Antimicrobial Therapy. Mayo Clin Proc. 86(2): 156-167). In certain embodiments, antibiotics can be used to selectively target bacteria of a specific niche. In some embodiments, antibiotics known to treat a particular infection that includes an immune disorder niche may be used to target immune-disorder-associated microbes, including immune-disorder-associated bacteria in that niche. In other embodiments, antibiotics are administered after the bacterial treatment. In some embodiments, antibiotics are administered after the bacterial treatment to remove the engraftment.

In some aspects, antibiotics can be selected based on their bactericidal or bacteriostatic properties. Bactericidal antibiotics include mechanisms of action that disrupt the cell wall (e.g., β-lactams), the cell membrane (e.g., daptomycin), or bacterial DNA (e.g., fluoroquinolones). Bacteriostatic agents inhibit bacterial replication and include sulfonamides, tetracyclines, and macrolides, and act by inhibiting protein synthesis. Furthermore, while some drugs can be bactericidal in certain organisms and bacteriostatic in others, knowing the target organism allows one skilled in the art to select an antibiotic with the appropriate properties. In certain treatment conditions, bacteriostatic antibiotics inhibit the activity of bactericidal antibiotics. Thus, in certain embodiments, bactericidal and bacteriostatic antibiotics are not combined.

Antibiotics include, but are not limited to aminoglycosides, ansamycins, carbacephems, carbapenems, cephalosporins, glycopeptides, lincosamides, lipopeptides, macrolides, monobactams, nitrofurans, oxazolidonones, penicillins, polypeptide antibiotics, quinolones, fluoroquinolone, sulfonamides, tetracyclines, and anti-mycobacterial compounds, and combinations thereof.

Aminoglycosides include, but are not limited to Amikacin, Gentamicin, Kanamycin, Neomycin, Netilmicin, Tobramycin, Paromomycin, and Spectinomycin. Aminoglycosides are effective, e.g., against Gram-negative bacteria, such as *Escherichia coli, Klebsiella, Pseudomonas aeruginosa*, and *Francisella tularensis*, and against certain aerobic bacteria but less effective against obligate/facultative anaerobes. Aminoglycosides are believed to bind to the bacterial 30S or 50S ribosomal subunit thereby inhibiting bacterial protein synthesis.

Ansamycins include, but are not limited to, Geldanamycin, Herbimycin, Rifamycin, and Streptovaricin. Geldanamycin and Herbimycin are believed to inhibit or alter the function of Heat Shock Protein 90.

Carbacephems include, but are not limited to, Loracarbef. Carbacephems are believed to inhibit bacterial cell wall synthesis.

Carbapenems include, but are not limited to, Ertapenem, Doripenem, Imipenem/Cilastatin, and Meropenem. Carbapenems are bactericidal for both Gram-positive and Gram-negative bacteria as broad-spectrum antibiotics. Carbapenems are believed to inhibit bacterial cell wall synthesis.

Cephalosporins include, but are not limited to, Cefadroxil, Cefazolin, Cefalotin, Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, and Ceftobiprole. Selected Cephalosporins are effective, e.g., against Gram-negative bacteria and against Gram-positive bacteria, including *Pseudomonas*, certain Cephalosporins are effective against methicillin-resistant *Staphylococcus aureus* (MRSA). Cephalosporins are believed to inhibit bacterial cell wall synthesis by disrupting synthesis of the peptidoglycan layer of bacterial cell walls.

Glycopeptides include, but are not limited to, Teicoplanin, Vancomycin, and Telavancin. Glycopeptides are effective, e.g., against aerobic and anaerobic Gram-positive bacteria including MRSA and *Clostridium difficile*. Glycopeptides are believed to inhibit bacterial cell wall synthesis by disrupting synthesis of the peptidoglycan layer of bacterial cell walls.

Lincosamides include, but are not limited to, Clindamycin and Lincomycin. Lincosamides are effective, e.g., against anaerobic bacteria, as well as *Staphylococcus*, and *Streptococcus*. Lincosamides are believed to bind to the bacterial 50S ribosomal subunit thereby inhibiting bacterial protein synthesis.

Lipopeptides include, but are not limited to, Daptomycin. Lipopeptides are effective, e.g., against Gram-positive bacteria. Lipopeptides are believed to bind to the bacterial membrane and cause rapid depolarization.

Macrolides include, but are not limited to, Azithromycin, Clarithromycin, Dirithromycin, Erythromycin, Roxithromycin, Troleandomycin, Telithromycin, and Spiramycin. Macrolides are effective, e.g., against *Streptococcus* and *Mycoplasma*. Macrolides are believed to bind to the bacterial or 50S ribosomal subunit, thereby inhibiting bacterial protein synthesis.

Monobactams include, but are not limited to, Aztreonam. Monobactams are effective, e.g., against Gram-negative bacteria. Monobactams are believed to inhibit bacterial cell wall synthesis by disrupting synthesis of the peptidoglycan layer of bacterial cell walls.

Nitrofurans include, but are not limited to, Furazolidone and Nitrofurantoin.

Oxazolidonones include, but are not limited to, Linezolid, Posizolid, Radezolid, and Torezolid. Oxazolidonones are believed to be protein synthesis inhibitors.

Penicillins include, but are not limited to, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin and Ticarcillin. Penicillins are effective, e.g., against Gram-positive bacteria, facultative anaerobes, e.g., *Streptococcus, Borrelia*, and *Treponema*. Penicillins are believed to inhibit bacterial cell wall synthesis by disrupting synthesis of the peptidoglycan layer of bacterial cell walls.

Penicillin combinations include, but are not limited to, Amoxicillin/clavulanate, Ampicillin/sulbactam, Piperacillin/tazobactam, and Ticarcillin/clavulanate.

Polypeptide antibiotics include, but are not limited to, Bacitracin, Colistin, and Polymyxin B and E. Polypeptide Antibiotics are effective, e.g., against Gram-negative bacteria. Certain polypeptide antibiotics are believed to inhibit isoprenyl pyrophosphate involved in synthesis of the peptidoglycan layer of bacterial cell walls, while others destabilize the bacterial outer membrane by displacing bacterial counter-ions.

Quinolones and Fluoroquinolone include, but are not limited to, Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, and Temafloxacin. Quinolones/Fluoroquinolone are effective, e.g., against *Streptococcus* and *Neisseria*. Quinolones/Fluoroquinolone are believed to inhibit the bacterial DNA gyrase or topoisomerase IV, thereby inhibiting DNA replication and transcription.

Sulfonamides include, but are not limited to, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Trimethoprim-Sulfamethoxazole (Co-trimoxazole), and Sulfonamidochrysoidine. Sulfonamides are believed to inhibit folate synthesis by competitive inhibition of dihydropteroate synthetase, thereby inhibiting nucleic acid synthesis.

Tetracyclines include, but are not limited to, Demeclocycline, Doxycycline, Minocycline, Oxytetracycline, and Tetracycline. Tetracyclines are effective, e.g., against Gram-negative bacteria. Tetracyclines are believed to bind to the bacterial 30S ribosomal subunit thereby inhibiting bacterial protein synthesis.

Anti-mycobacterial compounds include, but are not limited to, Clofazimine, Dapsone, Capreomycin, Cycloserine, Ethambutol, Ethionamide, Isoniazid, Pyrazinamide, Rifampicin, Rifabutin, Rifapentine, and Streptomycin.

Suitable antibiotics also include arsphenamine, chloramphenicol, fosfomycin, fusidic acid, metronidazole, mupirocin, platensimycin, quinupristin/dalfopristin, tigecycline, tinidazole, trimethoprim amoxicillin/clavulanate, ampicillin/sulbactam, amphomycin ristocetin, azithromycin, bacitracin, buforin II, carbomycin, cecropin P1, clarithromycin, erythromycins, furazolidone, fusidic acid, Na fusidate, gramicidin, imipenem, indolicidin, josamycin, magainan II, metronidazole, nitroimidazoles, mikamycin, mutacin B-Ny266, mutacin B-JH1 140, mutacin J-T8, nisin, nisin A, novobiocin, oleandomycin, ostreogrycin, piperacillin/tazobactam, pristinamycin, ramoplanin, ranalexin, reuterin, rifaximin, rosamicin, rosaramicin, spectinomycin, spiramycin, staphylomycin, streptogramin, streptogramin A, synergistin, taurolidine, teicoplanin, telithromycin, ticarcillin/clavulanic acid, triacetyloleandomycin, tylosin, tyrocidin, tyrothricin, vancomycin, vemamycin, and virginiamycin.

In some embodiments, the additional therapeutic is an immunosuppressive agent, a DMARD, a pain-control drug, a steroid, a non-steroidal antiinflammatory drug (NSAID), or a cytokine antagonist, and combinations thereof. Representative agents include, but are not limited to, cyclosporin, retinoids, corticosteroids, propionic acid derivative, acetic acid derivative, enolic acid derivatives, fenamic acid derivatives, Cox-2 inhibitors, lumiracoxib, ibuprophen, cholin magnesium salicylate, fenoprofen, salsalate, difunisal, tolmetin, ketoprofen, flurbiprofen, oxaprozin, indomethacin, sulindac, etodolac, ketorolac, nabumetone, naproxen, valdecoxib, etoricoxib, MK0966; rofecoxib, acetominophen, Celecoxib, Diclofenac, tramadol, piroxicam, meloxicam, tenoxicam, droxicam, lornoxicam, isoxicam, mefanamic acid, meclofenamic acid, flufenamic acid, tolfenamic, valdecoxib, parecoxib, etodolac, indomethacin, aspirin, ibuprophen, firocoxib, methotrexate (MTX), antimalarial drugs (e.g., hydroxychloroquine and chloroquine), sulfasalazine, Leflunomide, azathioprine, cyclosporin, gold salts, minocycline, cyclophosphamide, D-penicillamine, minocycline, auranofin, tacrolimus, myocrisin, chlorambucil, TNF alpha antagonists (e.g., TNF alpha antagonists or TNF alpha receptor antagonists), e.g., ADALIMUMAB (Humira®), ETANERCEPT (Enbrel®), INFLIXIMAB (Remicade®; TA-650), CERTOLIZUMAB PEGOL (Cimzia®; CDP870), GOLIMUMAB (Simpom®; CNTO 148), ANAKINRA (Kineret®), RITUXIMAB (Rituxan®; MabThera®), ABATACEPT (Orencia®), TOCILIZUMAB (RoActemra/Actemra®), integrin antagonists (TYSABRI® (natalizumab)), IL-1 antagonists (ACZ885 (Ilaris)), Anakinra (Kineret®)), CD4 antagonists, IL-23 antagonists, IL-20 antagonists, IL-6 antagonists, BLyS antagonists (e.g., Atacicept, Benlysta®/LymphoStat-B® (belimumab)), p38 Inhibitors, CD20 antagonists (Ocrelizumab, Ofatumumab (Arzerra®)), interferon gamma antagonists (Fontolizumab), prednisolone, Prednisone, dexamethasone, Cortisol, cortisone, hydrocortisone, methylprednisolone, betamethasone, triamcinolone, beclometasome, fludrocortisone, deoxycorticosterone, aldosterone, Doxycycline, vancomycin, pioglitazone, SBI-087, SCIO-469, Cura-100, Oncoxin+Viusid, TwHF, Methoxsalen, Vitamin D—ergocalciferol, Milnacipran, Paclitaxel, rosig tazone, Tacrolimus (Prograf®), RADOOl, rapamune, rapamycin, fostamatinib, Fentanyl, XOMA 052, Fostamatinib disodium, rosightazone, Curcumin (Longvida™), Rosuvastatin, Maraviroc, ramipnl, Milnacipran, Cobiprostone, somatropin, tgAAC94 gene therapy vector, MK0359, GW856553, esomeprazole, everolimus, trastuzumab, JAK1 and JAK2 inhibitors, pan JAK inhibitors, e.g., tetracyclic pyridone 6 (P6), 325, PF-956980, denosumab, IL-6 antagonists, CD20 antagonistis, CTLA4 antagonists, IL-8 antagonists, IL-21 antagonists, IL-22 antagonist, integrin antagonists (Tysarbri® (natalizumab)), VGEF antagnosits, CXCL antagonists, MMP antagonists, defensin antagonists, IL-1 antagonists (including IL-1 beta antagonists), and IL-23 antagonists (e.g., receptor decoys, antagonistic antibodies, etc.).

In some embodiments, the agent is an immunosuppressive agent. Examples of immunosuppressive agents include, but are not limited to, corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, TLR antagonists, inflammasome inhibitors, anti-cholinergic decongestants, mast-cell stabilizers, monoclonal anti-IgE antibodies, vaccines (e.g., vaccines used for vaccination where the amount of an allergen is gradually increased), cytokine inhibitors, such as anti-IL-6 antibodies, TNF inhibitors such as infliximab, adalimumab, certolizumab pegol, golimumab, or etanercept, and combinations thereof.

In some embodiments, the immune disorder therapy comprises administering a therapeutic bacteria and/or a therapeutic combination of bacteria to the subject so a healthy microbiome can be reconstituted in the subject. In some embodiments, the therapeutic bacteria is a non-immune-disorder-associated bacteria. In some embodiments the therapeutic bacteria is a probiotic bacteria.

In some embodiments, the additional therapeutic is a cancer therapeutic. In some embodiments, the cancer therapeutic is a chemotherapeutic agent. Examples of such chemotherapeutic agents include, but are not limited to, alkylating agents such as cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omega11; dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2′,2″-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylomithine (DMFO); retinoids such as retinoic acid; capecitabine; and pharmaceutically acceptable salts, acids or derivatives of any of the above.

In some embodiments, the cancer therapeutic is a cancer immunotherapy agent. Immunotherapy refers to a treatment that uses a subject's immune system to treat cancer, e.g., checkpoint inhibitors, cancer vaccines, cytokines, cell therapy, CAR-T cells, and dendritic cell therapy. Non-limiting examples of immunotherapies are checkpoint inhibitors include Nivolumab (BMS, anti-PD-1), Pembrolizumab (Merck, anti-PD-1), Ipilimumab (BMS, anti-CTLA-4), MEDI4736 (AstraZeneca, anti-PD-L1), and MPDL3280A (Roche, anti-PD-L1). Other immunotherapies may be tumor vaccines, such as Gardail, Cervarix, BCG, sipulencel-T, Gp100:209-217, AGS-003, DCVax-L, Algenpantucel-L, Tergenpantucel-L, TG4010, ProstAtak, Prostvac-V/R-TRICOM, Rindopepimul, E75 peptide acetate, IMA901, POL-103A, Belagenpumatucel-L, GSK1572932A, MDX-1279, GV1001, and Tecemotide. Immunotherapy may be administered via injection (e.g., intravenously, intratumorally, subcutaneously, or into lymph nodes), but may also be administered orally, topically, or via aerosol. Immunotherapies may comprise adjuvants such as cytokines.

In some embodiments, the immunotherapy agent is an immune checkpoint inhibitor. Immune checkpoint inhibition broadly refers to inhibiting the checkpoints that cancer cells can produce to prevent or downregulate an immune response. Examples of immune checkpoint proteins include, but are not limited to, CTLA4, PD-1, PD-L1, PD-L2, A2AR, B7-H3, B7-H4, BTLA, KIR, LAG3, TIM-3 or VISTA. Immune checkpoint inhibitors can be antibodies or antigen binding fragments thereof that bind to and inhibit an immune checkpoint protein. Examples of immune checkpoint inhibitors include, but are not limited to, nivolumab, pembrolizumab, pidilizumab, AMP-224, AMP-514, STI-A1110, TSR-042, RG-7446, BMS-936559, MEDI-4736, MSB-0020718C, AUR-012 and STI-A1010.

In some embodiments, the immunotherapy agent is an antibody or antigen binding fragment thereof that, for example, binds to a cancer-associated antigen. Examples of cancer-associated antigens include, but are not limited to, adipophilin, AIM-2, ALDHIA1, alpha-actinin-4, alpha-fetoprotein ("AFP"), ARTC1, B-RAF, BAGE-1, BCLX (L), BCR-ABL fusion protein b3a2, beta-catenin, BING-4, CA-125, CALCA, carcinoembryonic antigen ("CEA"), CASP-5, CASP-8, CD274, CD45, Cdc27, CDK12, CDK4, CDKN2A, CEA, CLPP, COA-1, CPSF, CSNKiA1, CTAG1, CTAG2, cyclin D1, Cyclin-A1, dek-can fusion protein, DKK1, EFTUD2, Elongation factor 2, ENAH (hMena), Ep-CAM, EpCAM, EphA3, epithelial tumor antigen ("ETA"), ETV6-AML1 fusion protein, EZH2, FGF5, FLT3-ITD, FN1, G250/MN/CAIX, GAGE-1,2,8, GAGE-3,4,5,6, 7, GAS7, glypican-3, GnTV, gp100/Pmel17, GPNMB, HAUS3, Hepsin, HER-2/neu, HERV-K-MEL, HLA-A11, HLA-A2, HLA-DOB, hsp70-2, IDO1, IGF2B3, IL13Ralpha2, Intestinal carboxyl esterase, K-ras, Kallikrein 4, KIF20A, KK-LC-1, KKLC1, KM-HN-1, KMHN1 also known as CCDC110, LAGE-1, LDLR-fucosyltransferaseAS fusion protein, Lengsin, M-CSF, MAGE-A1, MAGE-A10, MAGE-A12, MAGE-A2, MAGE-A3, MAGE-A4, MAGE-A6, MAGE-A9, MAGE-C1, MAGE-C2, malic enzyme, mammaglobin-A, MART2, MATN, MC1R, MCSP, mdm-2, ME1, Melan-A/MART-1, Meloe, Midkine, MMP-2, MMP-7, MUC1, MUC5AC, mucin, MUM-1, MUM-2, MUM-3, Myosin, Myosin class I, N-raw, NA88-A, neo-PAP, NFYC, NY-BR-1, NY-ESO-1/LAGE-2, OA1, OGT, OS-9, P polypeptide, p53, PAP, PAX5, PBF, pml-RARalpha fusion protein, polymorphic epithelial mucin ("PEM"), PPP1R3B, PRAME, PRDX5, PSA, PSMA, PTPRK, RAB38/NY-MEL-1, RAGE-1, RBAF600, RGS5, RhoC, RNF43, RU2AS, SAGE, secernin 1, SIRT2, SNRPD1, SOX10, Sp17, SPA17, SSX-2, SSX-4, STEAP1, survivin, SYT-SSX1 or -SSX2 fusion protein, TAG-1, TAG-2, Telomerase, TGF-betaRII, TPBG, TRAG-3, Triosephosphate isomerase, TRP-1/gp75, TRP-2, TRP2-INT2, tyrosinase, tyrosinase ("TYR"), VEGF, WT1, XAGE-lb/GAGED2a. In some embodiments, the antigen is a neo-antigen.

In some embodiments, the immunotherapy agent is a cancer vaccine and/or a component of a cancer vaccine (e.g., an antigenic peptide and/or protein). The cancer vaccine can be a protein vaccine, a nucleic acid vaccine or a combination thereof. For example, in some embodiments, the cancer vaccine comprises a polypeptide comprising an epitope of a cancer-associated antigen. In some embodiments, the cancer vaccine comprises a nucleic acid (e.g., DNA or RNA, such as mRNA) that encodes an epitope of a cancer-associated antigen. In some embodiemnts, the nucleic acid is a vector (e.g., a bacterial vector, viral vector). Examples of bacterial vectors include, but are not limited to, *Mycobacterium bovis* (BCG), *Salmonella Typhimurium* ssp., *Salmonella Typhi* ssp., *Clostridium* sp. spores, *Escherichia coli* Nissle 1917, *Escherichia coli* K-12/LLO, *Listeria monocytogenes*, and *Shigella flexneri*. Examples of viral vectors include, but are not limited to, vaccinia, adenovirus, RNA viruses, and replicationdefective avipox, replication-defective fowlpox, replication-defective canarypox, replicationdefective MVA and replication-defective adenovirus.

In some embodiments, the cancer immunotherapy comprises administration of an antigen presenting cell (APC) primed with a cancer-specific antigen. In some embodiments, the APC is a dendritic cell, a macrophage or a B cell.

Examples of cancer-associated antigens include, but are not limited to, adipophilin, AIM-2, ALDH1A1, alpha-actinin-4, alpha-fetoprotein ("AFP"), ARTC1, B-RAF, BAGE-1, BCLX (L), BCR-ABL fusion protein b3a2, beta-catenin, BING-4, CA-125, CALCA, carcinoembryonic antigen ("CEA"), CASP-5, CASP-8, CD274, CD45, Cdc27, CDK12, CDK4, CDKN2A, CEA, CLPP, COA-1, CPSF, CSNK1A1, CTAG1, CTAG2, cyclin D1, Cyclin-A1, dek-can fusion protein, DKK1, EFTUD2, Elongation factor 2, ENAH (hMena), Ep-CAM, EpCAM, EphA3, epithelial tumor antigen ("ETA"), ETV6-AML1 fusion protein, EZH2, FGF5, FLT3-ITD, FN1, G250/MN/CAIX, GAGE-1,2,8, GAGE-3,4,5,6,7, GAS7, glypican-3, GnTV, gpl00/Pmel17, GPNMB, HAUS3, Hepsin, HER-2/neu, HERV-K-MEL, HLA-A11, HLA-A2, HLA-DOB, hsp70-2, IDO1, IGF2B3, IL13Ralpha2, Intestinal carboxyl esterase, K-ras, Kallikrein 4, KIF20A, KK-LC-1, KKLC1, KM-HN-1, KMHN1 also known as CCDC110, LAGE-1, LDLR-fucosyltransferaseAS fusion protein, Lengsin, M-CSF, MAGE-A1, MAGE-A10, MAGE-A12, MAGE-A2, MAGE-A3, MAGE-A4, MAGE-A6, MAGE-A9, MAGE-C1, MAGE-C2, malic enzyme, mammaglobin-A, MART2, MATN, MC1R, MCSP, mdm-2, ME1, Melan-A/MART-1, Meloe, Midkine, MMP-2, MMP-7, MUC1, MUC5AC, mucin, MUM-1, MUM-2, MUM-3, Myosin, Myosin class I, N-raw, NA88-A, neo-PAP, NFYC, NY-BR-1, NY-ESO-1/LAGE-2, OA1, OGT, OS-9, P polypeptide, p53, PAP, PAX5, PBF, pml-RARalpha fusion protein, polymorphic epithelial mucin ("PEM"), PPP1R3B, PRAME, PRDX5, PSA, PSMA, PTPRK, RAB38/NY-MEL-1, RAGE-1, RBAF600, RGS5, RhoC, RNF43, RU2AS, SAGE, secernin 1, SIRT2, SNRPD1, SOX10, Sp17, SPA17, SSX-2, SSX-4, STEAP1, survivin, SYT-SSX1 or -SSX2 fusion protein, TAG-1, TAG-2, Telomerase, TGF-betaRII, TPBG, TRAG-3, Triosephosphate isomerase, TRP-1/gp75, TRP-2, TRP2-INT2, tyrosinase, tyrosinase ("TYR"), VEGF, WT1, XAGE-lb/GAGED2a. In some embodiments, the antigen is a neo-antigen.

In some embodiments, the cancer immunotherapy comprises administration of a cancer-specific chimeric antigen receptor (CAR). In some embodiments, the CAR is administered on the surface of a T cell. In some embodiments, the CAR binds specifically to a cancer-associated antigen.

In some embodiments, the cancer immunotherapy comprises administration of a cancer-specific T cell to the subject. In some embodiments, the T cell is a CD4+ T cell. In some embodiments, the CD4+ T cell is a TH1 T cell, a TH2 T cell or a TH17 T cell. In some embodiments, the T cell expresses a T cell receptor specific for a cancer-associated antigen.

In some embodiments, the cancer vaccine is administered with an adjuvant. Examples of adjuvants include, but are not limited to, an immune modulatory protein, Adjuvant 65, a-GalCer, aluminum phosphate, aluminum hydroxide, calcium phosphate, β-Glucan Peptide, CpG ODN DNA, GPI-0100, lipid A, lipopolysaccharide, Lipovant, Montanide, N-acetyl-muramyl-L-alanyl-D-isoglutamine, Pam3CSK4, quil A, cholera toxin (CT) and heat-labile toxin from enterotoxigenic *Escherichia coli* (LT) including derivatives of these (CTB, mmCT, CTA1-DD, LTB, LTK63, LTR72, dmLT) and trehalose dimycolate.

In some embodiments, the immunotherapy agent is an immune modulating protein to the subject. In some embodiments, the immune modulatory protein is a cytokine or chemokine. Examples of immune modulating proteins include, but are not limited to, B lymphocyte chemoattractant ("BLC"), C-C motif chemokine 11 ("Eotaxin-1"), Eosinophil chemotactic protein 2 ("Eotaxin-2"), Granulocyte colony-stimulating factor ("G-CSF"), Granulocyte macrophage colony-stimulating factor ("GM-CSF"), 1-309, Intercellular Adhesion Molecule 1 ("ICAM-1"), Interferon alpha ("IFN-alpha"), Interferon beta ("IFN-beta") Interferon gamma ("IFN-gamma"), Interlukin-1 alpha ("IL-1 alpha"), Interlukin-1 beta ("IL-1 beta"), Interleukin 1 receptor antagonist ("IL-1 ra"), Interleukin-2 ("IL-2"), Interleukin-4 ("IL-4"), Interleukin-5 ("IL-5"), Interleukin-6 ("IL-6"), Interleukin-6 soluble receptor ("IL-6 sR"), Interleukin-7 ("IL-7"), Interleukin-8 ("IL-8"), Interleukin-10 ("IL-10"), Interleukin-11 ("IL-11"), Subunit beta of Interleukin-12 ("IL-12 p40" or "IL-12 p70"), Interleukin-13 ("IL-13"), Interleukin-15 ("IL-15"), Interleukin-16 ("IL-16"), Interleukin-17A-F ("IL-17A-F"), Interleukin-18 ("IL-18"), Interleukin-21 ("IL-21"), Interleukin-22 ("IL-22"), Interleukin-23 ("IL-23"), Interleukin-33 ("IL-33"), Chemokine (C-C motif) Ligand 2 ("MCP-1"), Macrophage colony-stimulating factor ("M-CSF"), Monokine induced by gamma interferon ("MIG"), Chemokine (C-C motif) ligand 2 ("MIP-1 alpha"), Chemokine (C-C motif) ligand 4 ("MIP-1 beta"), Macrophage inflammatory protein-1-delta ("MIP-1 delta"), Platelet-derived growth factor subunit B ("PDGF-BB"), Chemokine (C-C motif) ligand 5, Regulated on Activation, Normal T cell Expressed and Secreted ("RANTES"), TIMP metallopeptidase inhibitor 1 ("TIMP-1"), TIMP metallopeptidase inhibitor 2 ("TIMP-2"), Tumor necrosis factor, lymphotoxin-alpha ("TNF alpha"), Tumor necrosis factor, lymphotoxin-beta ("TNF beta"), Soluble TNF receptor type 1 ("sTNFRI"), sTNFRIIAR, Brain-derived neurotrophic factor ("BDNF"), Basic fibroblast growth factor ("bFGF"), Bone morphogenetic protein 4 ("BMP-4"), Bone morphogenetic protein 5 ("BMP-5"), Bone morphogenetic protein 7 ("BMP-7"), Nerve growth factor ("b-NGF"), Epidermal growth factor ("EGF"), Epidermal growth factor receptor ("EGFR"), Endocrine-gland-derived vascular endothelial growth factor ("EG-VEGF"), Fibroblast growth factor 4 ("FGF-4"), Keratinocyte growth factor ("FGF-7"), Growth differentiation factor 15 ("GDF-15"), Glial cell-derived neurotrophic factor ("GDNF"), Growth Hormone, Heparin-binding EGF-like growth factor ("HB-EGF"), Hepatocyte growth factor ("HGF"), Insulin-like growth factor binding protein 1 ("IGFBP-1"), Insulin-like growth factor binding protein 2 ("IGFBP-2"), Insulin-like growth factor binding protein 3 ("IGFBP-3"), Insulin-like growth factor binding protein 4 ("IGFBP-4"), Insulin-like growth factor binding protein 6 ("IGFBP-6"), Insulin-like growth factor 1 ("IGF-1"), Insulin, Macrophage colony-stimulating factor ("M-CSF R"), Nerve growth factor receptor ("NGF R"), Neurotrophin-3 ("NT-3"), Neurotrophin-4 ("NT-4"), Osteoclastogenesis inhibitory factor ("Osteoprotegerin"), Platelet-derived growth factor receptors ("PDGF-AA"), Phosphatidylinositol-glycan biosynthesis ("PIGF"), Skp, Cullin, F-box containing comples ("SCF"), Stem cell factor receptor ("SCF R"), Transforming growth factor alpha ("TGFalpha"), Transforming growth factor beta-1 ("TGF beta 1"), Transforming growth factor beta-3 ("TGF beta 3"), Vascular endothelial growth factor ("VEGF"), Vascular endothelial growth factor receptor 2 ("VEGFR2"), Vascular endothelial growth factor receptor 3 ("VEGFR3"), VEGF-D 6Ckine, Tyrosine-protein kinase receptor UFO ("Axl"), Betacellulin ("BTC"), Mucosae-associated epithelial chemokine ("CCL28"), Chemokine (C-C motif) ligand 27 ("CTACK"), Chemokine (C-X-C motif) ligand 16 ("CXCL16"), C-X-C motif chemokine 5 ("ENA-78"), Chemokine (C-C motif) ligand 26 ("Eotaxin-3"), Granulocyte chemotactic protein 2 ("GCP-2"), GRO, Chemokine (C-C motif) ligand 14 ("HCC-1"), Chemokine (C-C motif) ligand 16 ("HCC-4"), Interleukin-9 ("IL-9"), Interleukin-17 F ("IL-17F"), Interleukin-18-binding protein ("IL-18 BPa"), Interleukin-28 A ("IL-28A"), Interleukin 29 ("IL-29"), Interleukin 31 ("IL-31"), C-X-C motif chemokine 10 ("IP-10"), Chemokine receptor CXCR3 ("I-TAC"), Leukemia inhibitory factor ("LIF"), Light, Chemokine (C motif) ligand ("Lymphotactin"), Monocyte chemoattractant protein 2 ("MCP-2"), Monocyte chemoattractant protein 3 ("MCP-3"), Monocyte chemoattractant protein 4 ("MCP-4"), Macrophage-derived chemokine ("MDC"), Macrophage migration inhibitory factor ("MIF"), Chemokine (C-C motif) ligand 20 ("MIP-3 alpha"), C-C motif chemokine 19 ("MIP-3 beta"), Chemokine (C-C motif) ligand 23 ("MPIF-1"), Macrophage stimulating protein alpha chain ("MSPalpha"), Nucleosome assembly protein 1-like 4 ("NAP-2"), Secreted phosphoprotein 1 ("Osteopontin"), Pulmonary and activation-regulated cytokine ("PARC"), Platelet factor 4 ("PF4"), Stroma cell-derived factor-1 alpha ("SDF-1 alpha"), Chemokine (C-C motif) ligand 17 ("TARC"), Thymus-expressed chemokine ("TECK"), Thymic stromal lymphopoietin ("TSLP 4-IBB"), CD 166 antigen ("ALCAM"), Cluster of Differentiation 80 ("B7-1"), Tumor necrosis factor receptor superfamily member 17 ("BCMA"), Cluster of Differentiation 14 ("CD14"), Cluster of Differentiation 30 ("CD30"), Cluster of Differentiation 40 ("CD40 Ligand"), Carcinoembryonic antigen-related cell adhesion molecule 1 (biliary glycoprotein) ("CEACAM-1"), Death Receptor 6 ("DR6"), Deoxythymidine kinase ("Dtk"), Type 1 membrane glycoprotein ("Endoglin"), Receptor tyrosine-protein kinase erbB-3 ("ErbB3"), Endothelial-leukocyte adhesion molecule 1 ("E-Selectin"), Apoptosis antigen 1 ("Fas"), Fms-like tyrosine kinase 3 ("Flt-3L"), Tumor necrosis factor receptor superfamily member 1 ("GITR"), Tumor necrosis factor receptor superfamily member 14 ("HVEM"), Intercellular adhesion molecule 3 ("ICAM-3"), IL-1 R4, IL-1 RI, IL-10 Rbeta, IL-17R, IL-2Rgamma, IL-21R, Lysosome membrane protein 2 ("LIMPII"), Neutrophil gelatinase-associated lipocalin ("Lipocalin-2"), CD62L ("L-Selectin"), Lymphatic endothelium ("LYVE-1"), MHC class I polypeptide-related sequence A ("MICA"), MHC class I polypeptide-related sequence B ("MICB"), NRG1-betal, Beta-type platelet-derived growth factor receptor ("PDGF Rbeta"), Platelet endothelial cell adhesion molecule ("PECAM-1"), RAGE, Hepatitis A virus cellular receptor 1 ("TIM-1"), Tumor necrosis factor receptor superfamily member IOC ("TRAIL R3"), Trappin protein transglutaminase binding domain ("Trappin-2"), Urokinase receptor ("uPAR"), Vascular cell adhesion protein 1 ("VCAM-1"), XEDARActivin A, Agouti-related protein ("AgRP"), Ribonuclease 5 ("Angiogenin"), Angiopoietin 1, Angiostatin, Catheprin S, CD40, Cryptic family protein IB ("Cripto-1"), DAN, Dickkopf-related protein 1 ("DKK-1"), E-Cadherin, Epithelial cell adhesion molecule ("EpCAM"), Fas Ligand (FasL or CD95L), Fcg RIIB/C, FoUistatin, Galectin-7, Intercellular adhesion molecule 2 ("ICAM-2"), IL-13 R1, IL-13R2, IL-17B, IL-2 Ra, IL-2 Rb, IL-23, LAP, Neuronal cell adhesion molecule ("NrCAM"), Plasminogen activator inhibitor-1 ("PAI-1"), Platelet derived growth factor receptors ("PDGF-AB"), Resistin, stromal cell-derived factor 1 ("SDF-1 beta"), sgpl30, Secreted frizzled-related protein 2 ("ShhN"), Sialic acid-binding immunoglobulin-type lectins ("Siglec-5"), ST2, Transforming growth factor-beta 2 ("TGF beta 2"), Tie-2, Thrombopoietin ("TPO"), Tumor necrosis factor receptor superfamily member 10D ("TRAIL R4"), Triggering receptor expressed on myeloid cells 1 ("TREM-1"), Vascular endothelial growth factor C ("VEGF-C"), VEGFRlAdiponectin, Adipsin ("AND"), Alpha-fetoprotein ("AFP"), Angiopoietin-like 4 ("ANGPTL4"), Beta-2-microglobulin ("B2M"), Basal cell adhesion molecule ("BCAM"), Carbohydrate antigen 125 ("CA125"), Cancer Antigen 15-3 ("CA15-3"), Carcinoembryonic antigen ("CEA"), cAMP receptor protein ("CRP"), Human Epidermal Growth Factor Receptor 2 ("ErbB2"), Follistatin, Follicle-stimulating hormone ("FSH"), Chemokine (C-X-C motif) ligand 1 ("GRO alpha"), human chorionic gonadotropin ("beta HCG"), Insulin-like growth factor 1 receptor ("IGF-1 sR"), IL-1 sRII, IL-3, IL-18 Rb, IL-21, Leptin, Matrix metalloproteinase-1 ("MMP-1"), Matrix metalloproteinase-2 ("MMP-2"), Matrix metalloproteinase-3 ("MMP-3"), Matrix metalloproteinase-8 ("MMP-8"), Matrix metalloproteinase-9 ("MMP-9"), Matrix metalloproteinase-10 ("MMP-10"), Matrix metalloproteinase-13 ("MMP-13"), Neural Cell Adhesion Molecule ("NCAM-1"), Entactin ("Nidogen-1"), Neuron specific enolase ("NSE"), Oncostatin M ("OSM"), Procalcitonin, Prolactin, Prostate specific antigen ("PSA"), Sialic acid-binding Ig-like lectin 9 ("Siglec-9"), ADAM 17 endopeptidase ("TACE"), Thyroglobulin, Metalloproteinase inhibitor 4 ("TIMP-4"), TSH2B4, Disintegrin and metalloproteinase domain-containing protein 9 ("ADAM-9"), Angiopoietin 2, Tumor necrosis factor ligand superfamily member 13/Acidic leucine-rich nuclear phosphoprotein 32 family member B ("APRIL"), Bone morphogenetic protein 2 ("BMP-2"), Bone morphogenetic protein 9 ("BMP-9"), Complement component 5a ("C5a"), Cathepsin L, CD200, CD97, Chemerin, Tumor necrosis factor receptor superfamily member 6B ("DcR3"), Fatty acid-binding protein 2 ("FABP2"), Fibroblast activation protein, alpha ("FAP"), Fibroblast growth factor 19 ("FGF- 19"), Galectin-3, Hepatocyte growth factor receptor ("HGF R"), IFN-gammalpha/beta R2, Insulin-like growth factor 2 ("IGF-2"), Insulin-like growth factor 2 receptor ("IGF-2 R"), Interleukin-1 receptor 6 ("IL-1R6"), Interleukin 24 ("IL-24"), Interleukin 33 ("IL-33", Kallikrein 14, Asparaginyl endopeptidase ("Legumain"), Oxidized low-density lipoprotein receptor 1 ("LOX-1"), Mannose-binding lectin ("MBL"), Neprilysin ("NEP"), Notch homolog 1, translocation-associated (Drosophila) ("Notch-1"), Nephroblastoma overexpressed ("NOV"), Osteoactivin, Programmed cell death protein 1 ("PD-1"), N-acetylmuramoyl-L-alanine amidase ("PGRP-5"), Serpin A4, Secreted frizzled related protein 3 ("sFRP-3"), Thrombomodulin, Tolllike receptor 2 ("TLR2"), Tumor necrosis factor receptor superfamily member 10A ("TRAIL RI"), Transferrin ("TRF"), WIF-1ACE-2, Albumin, AMICA, Angiopoietin 4, B-cell activating factor ("BAFF"), Carbohydrate antigen 19-9 ("CA19-9"), CD 163, Clusterin, CRT AM, Chemokine (C-X-C motif) ligand 14 ("CXCL14"), Cystatin C, Decorin ("DCN"), Dickkopf-related protein 3 ("Dkk-3"), Delta-like protein 1 ("DLL1"), Fetuin A, Heparin-binding growth factor 1 ("aFGF"), Folate receptor alpha ("FOLR1"), Furin, GPCR-associated sorting protein 1 ("GASP-1"), GPCR-associated sorting protein 2 ("GASP-2"), Granulocyte colony-stimulating factor receptor ("GCSF R"), Serine protease hepsin ("HAI-2"), Interleukin-17B Receptor ("IL-17B R"), Interleukin 27 ("IL-27"), Lymphocyte-activation gene 3 ("LAG-3"), Apolipoprotein A-V ("LDL R"), Pepsinogen I, Retinol binding protein 4 ("RBP4"), SOST, Heparan sulfate proteoglycan ("Syndecan-1"), Tumor necrosis factor receptor superfamily member 13B ("TACI"), Tissue factor pathway inhibitor ("TFPI"), TSP-1, Tumor necrosis factor receptor superfamily, member 10b ("TRAIL R2"), TRANCE, Troponin I, Urokinase Plasminogen Activator ("uPA"), Cadherin 5, type 2 or VE-cadherin (vascular endothelial) also known as CD144 ("VE-Cadherin"), WNT1-inducible-signaling pathway protein 1 ("WISP-1"), and Receptor Activator of Nuclear Factor κ B ("RANK").

In some embodiments, the cancer therapeutic agent is an anti-cancer compound. Exemplary anti-cancer compounds include, but are not limited to, Alemtuzumab (Campath®), Alitretinoin (Panretin®), Anastrozole (Arimidex®), Bevacizumab (Avastin®), Bexarotene (Targretin®), Bortezomib (Velcade®), Bosutinib (Bosulif®), Brentuximab vedotin (Adcetris®), Cabozantinib (Cometriq™), Carfilzomib (Kyprolis™), Cetuximab (Erbitux®), Crizotinib (Xalkori®), Dasatinib (Sprycel®), Denileukin diftitox (Ontak®), Erlotinib hydrochloride (Tarceva®), Everolimus (Afinitor®), Exemestane (Aromasin®), Fulvestrant (Faslodex®), Gefitinib (Iressa®), Ibritumomab tiuxetan (Zevalin®), Imatinib mesylate (Gleevec®), Ipilimumab (Yervoy™), Lapatinib ditosylate (Tykerb®), Letrozole (Femara®), Nilotinib (Tasigna®), Ofatumumab (Arzerra®), Panitumumab (Vectibix®), Pazopanib hydrochloride (Votrient®), Pertuzumab (Perjeta™), Pralatrexate (Folotyn®), Regorafenib (Stivarga®), Rituximab (Rituxan®), Romidepsin (Istodax®), Sorafenib tosylate (Nexavar®), Sunitinib malate (Sutent®), Tamoxifen, Temsirolimus (Torisel®), Toremifene (Fareston®), Tositumomab and 131I-tositumomab (Bexxar®), Trastuzumab (Herceptin®), Tretinoin (Vesanoid®), Vandetanib (Caprelsa®), Vemurafenib (Zelboraf®), Vorinostat (Zolinza®), and Ziv-aflibercept (Zaltrap®).

Exemplary anti-cancer compounds that modify the function of proteins that regulate gene expression and other cellular functions (e.g., HDAC inhibitors, retinoid receptor ligands) are Vorinostat (Zolinza®), Bexarotene (Targretin®) and Romidepsin (Istodax®), Alitretinoin (Panretin®), and Tretinoin (Vesanoid®).

Exemplary anti-cancer compounds that induce apoptosis (e.g., proteasome inhibitors, antifolates) are Bortezomib (Velcade®), Carfilzomib (Kyprolis™), and Pralatrexate (Folotyn®).

Exemplary anti-cancer compounds that increase anti-tumor immune response (e.g., anti CD20, anti CD52; anti-cytotoxic T-lymphocyte-associated antigen-4) are Rituximab (Rituxan®), Alemtuzumab (Campath®), Ofatumumab (Arzerra®), and Ipilimumab (Yervoy™).

Exemplary anti-cancer compounds that deliver toxic agents to cancer cells (e.g., anti-CD20-radionuclide fusions; IL-2-diphtheria toxin fusions; anti-CD30-monomethylauristatin E (MMAE)-fusions) are Tositumomab and 131I-tositumomab (Bexxar®) and Ibritumomab tiuxetan (Zevalin®), Denileukin diftitox (Ontak®), and Brentuximab vedotin (Adcetris®).

Other exemplary anti-cancer compounds are small molecule inhibitors and conjugates thereof of, e.g., Janus kinase, ALK, Bcl-2, PARP, PI3K, VEGF receptor, Braf, MEK, CDK, and HSP90.

Exemplary platinum-based anti-cancer compounds include, for example, cisplatin, carboplatin, oxaliplatin, satraplatin, picoplatin, Nedaplatin, Triplatin, and Lipoplatin. Other metal-based drugs suitable for treatment include, but are not limited to ruthenium-based compounds, ferrocene derivatives, titanium-based compounds, and gallium-based compounds.

In some embodiments, the cancer therapeutic is a radioactive moiety that comprises a radionuclide. Exemplary radionuclides include, but are not limited to, Cr-51, Cs-131, Ce-134, Se-75, Ru-97, 1-125, Eu-149, Os-189m, Sb-119, 1-123, Ho-161, Sb-117, Ce-139, In-111, Rh-103m, Ga-67, T1-201, Pd-103, Au-195, Hg-197, Sr-87m, Pt-191, P-33, Er-169, Ru-103, Yb-169, Au-199, Sn-121, Tm-167, Yb-175, In-113m, Sn-113, Lu-177, Rh-105, Sn-117m, Cu-67, Sc-47, Pt-195m, Ce-141, 1-131, Tb-161, As-77, Pt-197, Sm-153, Gd-159, Tm-173, Pr-143, Au-198, Tm-170, Re-186, Ag-111, Pd-109, Ga-73, Dy-165, Pm-149, Sn-123, Sr-89, Ho-166, P-32, Re-188, Pr-142, Ir-194, In-114m/In-114, and Y-90.

In some embodiments, the cancer therapeutic is an antibiotic. For example, if the presence of a cancer-associated bacteria and/or a cancer-associated microbiome profile is detected according to the methods provided herein, antibiotics can be administered to eliminate the cancer-associated bacteria from the subject. "Antibiotics" broadly refers to compounds capable of inhibiting or preventing a bacterial infection. Antibiotics can be classified in a number of ways, including their use for specific infections, their mechanism of action, their bioavailability, or their spectrum of target microbe (e.g., Gram-negative vs. Gram-positive bacteria, aerobic vs. anaerobic bacteria, etc.) and these may be used to kill specific bacteria in specific areas of the host ("niches") (Leekha, et al 2011. General Principles of Antimicrobial Therapy. Mayo Clin Proc. 86(2): 156-167). In certain embodiments, antibiotics can be used to selectively target bacteria of a specific niche. In some embodiments, antibiotics known to treat a particular infection that includes a cancer niche may be used to target cancer-associated microbes, including cancer-associated bacteria in that niche. In other embodiments, antibiotics are administered after the bacterial treatment. In some embodiments, antibiotics are administered after the bacterial treatment to remove the engraftment.

Immune Disorders

In some embodiments, the methods and compositions described herein relate to the treatment or prevention of a disease or disorder associated with a pathological immune response, such as an autoimmune disease, an allergic reaction and/or an inflammatory disease. In some embodiments, the disease or disorder is an inflammatory bowel disease (e.g., Crohn's disease or ulcerative colitis). In some embodiments, the methods and compositions described herein relate to the treatment or prevention of delayed-type hypersensitivity, autoimmune myocarditis, granulomas, peripheral neuropathies, Hashimoto's thyroiditis, inflammation of the colon, colitis, microscopic colitis, collagenous colitis, diversion colitis, chemical colitis, ischemic colitis, indeterminate colitis, atypical colitis.

The methods described herein can be used to treat any subject in need thereof. As used herein, a "subject in need thereof" includes any subject that has a disease or disorder associated with a pathological immune response (e.g., an inflammatory bowel disease), as well as any subject with an increased likelihood of acquiring a such a disease or disorder.

The compositions described herein can be used, for example, as a pharmaceutical composition for preventing or treating (reducing, partially or completely, the adverse effects of) an autoimmune disease, such as chronic inflammatory bowel disease, systemic lupus erythematosus, psoriasis, muckle-wells syndrome, rheumatoid arthritis, multiple sclerosis, or Hashimoto's disease; an allergic disease, such as a food allergy, pollenosis, or asthma; an infectious disease, such as an infection with *Clostridium difficile*; an inflammatory disease such as a TNF-mediated inflammatory disease (e.g., an inflammatory disease of the gastrointestinal tract, such as pouchitis, a cardiovascular inflammatory condition, such as atherosclerosis, or an inflammatory lung disease, such as chronic obstructive pulmonary disease); a pharmaceutical composition for suppressing rejection in organ transplantation or other situations in which tissue rejection might occur; a supplement, food, or beverage for improving immune functions; or a reagent for suppressing the proliferation or function of immune cells.

In some embodiments, the methods provided herein are useful for the treatment of inflammation. In certain embodiments, the inflammation of any tissue and organs of the body, including musculoskeletal inflammation, vascular inflammation, neural inflammation, digestive system inflammation, ocular inflammation, inflammation of the reproductive system, and other inflammation, as discussed below.

Immune disorders of the musculoskeletal system include, but are not limited to, those conditions affecting skeletal joints, including joints of the hand, wrist, elbow, shoulder, jaw, spine, neck, hip, knew, ankle, and foot, and conditions affecting tissues connecting muscles to bones such as tendons. Examples of such immune disorders, which may be treated with the methods and compositions described herein include, but are not limited to, arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Ocular immune disorders refers to an immune disorder that affects any structure of the eye, including the eye lids. Examples of ocular immune disorders which may be treated with the methods and compositions described herein include, but are not limited to, blepharitis, blepharochalasis, conjunctivitis, dacryoadenitis, keratitis, keratoconjunctivitis sicca (dry eye), scleritis, trichiasis, and uveitis Examples of nervous system immune disorders which may be treated with the methods and compositions described herein include, but are not limited to, encephalitis, Guillain-Barre syndrome, meningitis, neuromyotonia, narcolepsy, multiple sclerosis, myelitis and schizophrenia. Examples of inflammation of the vasculature or lymphatic system which may be treated with the methods and compositions described herein include, but are not limited to, arthrosclerosis, arthritis, phlebitis, vasculitis, and lymphangitis.

Examples of digestive system immune disorders which may be treated with the methods and compositions described herein include, but are not limited to, cholangitis, cholecystitis, enteritis, enterocolitis, gastritis, gastroenteritis, inflammatory bowel disease, ileitis, and proctitis. Inflammatory bowel diseases include, for example, certain art-recognized forms of a group of related conditions. Several major forms of inflammatory bowel diseases are known, with Crohn's disease (regional bowel disease, e.g., inactive and active forms) and ulcerative colitis (e.g., inactive and active forms) the most common of these disorders. In addition, the inflammatory bowel disease encompasses irritable bowel syndrome, microscopic colitis, lymphocytic-plasmocytic enteritis, coeliac disease, collagenous colitis, lymphocytic colitis and eosinophilic enterocolitis. Other less common forms of IBD include indeterminate colitis, pseudomembranous colitis (necrotizing colitis), ischemic inflammatory bowel disease, Behcet's disease, sarcoidosis, scleroderma, IBD-associated dysplasia, dysplasia associated masses or lesions, and primary sclerosing cholangitis.

Examples of reproductive system immune disorders which may be treated with the methods and compositions described herein include, but are not limited to, cervicitis, chorioamnionitis, endometritis, epididymitis, omphalitis, oophoritis, orchitis, salpingitis, tubo-ovarian abscess, urethritis, vaginitis, vulvitis, and vulvodynia.

The methods and compositions described herein may be used to treat autoimmune conditions having an inflammatory component. Such conditions include, but are not limited to, acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schonlein purpura, Kawasaki's disease, lupus erythematosus, microscopic colitis, microscopic polyarteritis, mixed connective tissue disease, Muckle-Wells syndrome, multiple sclerosis, myasthenia gravis, opsoclonus myoclonus syndrome, optic neuritis, ord's thyroiditis, pemphigus, *nodosa*, polymyalgia, rheumatoid arthritis, Reiter's syndrome, Sjogren's syndrome, temporal arteritis, Wegener's granulomatosis, warm autoimmune haemolytic anemia, interstitial cystitis, Lyme disease, morphea, psoriasis, sarcoidosis, scleroderma, ulcerative colitis, and vitiligo.

The methods and compositions described herein may be used to treat T-cell mediated hypersensitivity diseases having an inflammatory component. Such conditions include, but are not limited to, contact hypersensitivity, contact dermatitis (including that due to poison ivy), uticaria, skin allergies, respiratory allergies (hay fever, allergic rhinitis, house dustmite allergy) and gluten-sensitive enteropathy (Celiac disease).

Other immune disorders which may be treated with the methods and compositions include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome, Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensistivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosus, psoriasis, chronic obstructive pulmonary disease, and inflammation accompanying infectious conditions (e.g., sepsis).

The methods and compositions described herein may be used to treat metabolic disease, disorders and syndromes. Such conditions include, but are not limited to, Type II Diabetes, Encephalopathy, Tay-Sachs disease, Krabbe disease, Galactosemia, Phenylketonuria (PKU), and Maple syrup urine disease.

The methods and compositions described herein may be used to treat neurodegenerative and neurological diseases. Such conditions include, but are not limited to, Parkinson's disease, Alzheimer's disease, prion disease, Huntington's disease, motor neurone diseases (MND), spinocerebellar ataxia, spinal muscular atrophy, dystonia, idiopathicintracranial hypertension, epilepsy, nervous system disease, central nervous system disease, movement disorders, multiple sclerosis, encephalopathy, peripheral neuropathy and postoperative cognitive dysfunction.

Cancer

In some embodiments, the methods and compositions described herein relate to the treatment of cancer. In some embodiments, any cancer can be treated using the methods described herein. Examples of cancers that may treated by methods and compositions described herein include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; plasmacytoma, colorectal cancer, rectal cancer, and hairy cell leukemia.

In some embodiments, the methods and compositions provided herein relate to the treatment of a leukemia. The term "leukemia" is meant broadly progressive, malignant diseases of the hematopoietic organs/systems and is generally characterized by a distorted proliferation and development of leukocytes and their precursors in the blood and bone marrow. Non-limiting examples of leukemia diseases include, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, and promyelocytic leukemia.

In some embodiments, the methods and compositions provided herein relate to the treatment of a carcinoma. The term "carcinoma" refers to a malignant growth made up of epithelial cells tending to infiltrate the surrounding tissues, and/or resist physiological and non-physiological cell death signals and gives rise to metastases. Non-limiting exemplary types of carcinomas include, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma villosum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, merkel cell carcinoma, salivary gland carcinoma and carcinoma scroti.

In some embodiments, the methods and compositions provided herein relate to the treatment of a sarcoma. The term "sarcoma" generally refers to a tumor which is made up of a substance like the embryonic connective tissue and is generally composed of closely packed cells embedded in a fibrillar, heterogeneous, or homogeneous substance. Sarcomas include, but are not limited to, chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Additional exemplary neoplasias that can be treated using the methods and compositions described herein include Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer.

In some embodiments, the cancer treated is a melanoma. The term "melanoma" is taken to mean a tumor arising from the melanocytic system of the skin and other organs. Non-limiting examples of melanomas are Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, and superficial spreading melanoma.

Particular categories of tumors that can be treated using methods and compositions described herein include lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, as well as metastases of all the above. Particular types of tumors include hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, pulmonary squamous cell carcinoma, basal cell carcinoma, adenocarcinoma (well differentiated, moderately differentiated, poorly differentiated or undifferentiated), bronchioloalveolar carcinoma, renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

Cancers treated in certain embodiments also include pre-cancerous lesions, e.g., actinic keratosis (solar keratosis), moles (dysplastic nevi), acitinic chelitis (farmer's lip), cutaneous horns, Barrett's esophagus, atrophic gastritis, dyskeratosis congenita, sideropenic dysphagia, lichen planus, oral submucous fibrosis, actinic (solar) elastosis and cervical dysplasia.

Cancers treated in some embodiments include non-cancerous or benign tumors, e.g., of endodermal, ectodermal or mesenchymal origin, including, but not limited to cholangioma, colonic polyp, adenoma, papilloma, cystadenoma, liver cell adenoma, hydatidiform mole, renal tubular adenoma, squamous cell papilloma, gastric polyp, hemangioma, osteoma, chondroma, lipoma, fibroma, lymphangioma, leiomyoma, rhabdomyoma, astrocytoma, nevus, meningioma, and ganglioneuroma.

EXAMPLES

Example 1: Immune Modulation of Human Commensal Bacteria in a KLH-based Delayed Type Hypersensitivity Model Delayed-type hypersensitivity (DTH) is an animal model of atopic dermatitis (or allergic contact dermatitis), as reviewed by Petersen et al. (In vivo pharmacological disease models for psoriasis and atopic dermatitis in drug discovery. Basic & Clinical Pharm & Toxicology. 2006. 99(2): 104-115; see also Irving C. Allen (ed.) Mouse Models of Innate Immunity: Methods and Protocols, Methods in Molecular Biology, 2013. vol. 1031, DOI 10.1007/978-1-62703-481-4_13). It can be induced in a variety of mouse and rat strains using various haptens or antigens, for example an antigen emulsified with an adjuvant. DTH is characterized by sensitization as well as an antigen-specific T cell-mediated reaction that results in erythema, edema, and cellular infiltration—especially infiltration of antigen presenting cells (APCs), eosinophils, activated CD4+ T cells, and cytokine-expressing Th2 cells.

The test formulations were prepared for KLH-based delayed type hypersensitivity model. The delayed-type hypersensitivity (DTH) model provides an in vivo mechanism to study the cell-mediated immune response, and resulting inflammation, following exposure to a specific antigen to which the mice have been sensitized. Several variations of the DTH model have been used and are well known in the art (Irving C. Allen (ed.). *Mouse Models of Innate Immunity: Methods and Protocols*, Methods in Molecular Biology. Vol. 1031, DOI 10.1007/978-1-62703-481-4_13, Springer Science+Business Media, LLC 2013). For example, the emulsion of Keyhole Limpet Hemocyanin (KLH) and Complete Freund's Adjuvant (CFA) are prepared freshly on the day of immunization (day 0). To this end, 8 mg of KLH powder is weighed and is thoroughly resuspended in 16 mL saline. An emulsion is prepared by mixing the KLH/saline with an equal volume of CFA solution (e.g. 10 mL KLH/saline+10 mL CFA solution) using syringes and a luer lock connector. KLH and CFA is mixed vigorously for several minutes to form a white-colored emulsion to obtain maximum stability. A drop test is performed to check if a homogenous emulsion is obtained, mixing is continued until an intact drop remains visible in the water.

On day 0, C57Bl/6J female mice, approximately 7 weeks old, were primed with KLH antigen in CFA by subcutaneous immunization (4 sites, 50 µL per site).

Dexamethasone, a corticosteroid, is a known anti-inflammatory that ameliorates DTH reactions in mice, and serves as a positive control for suppressing inflammation in this model (Taube and Carlsten, Action of dexamethasone in the suppression of delayed-type hypersensitivity in reconstituted SCID mice. Inflamm Res. 2000. 49(10): 548-52). For the positive control group, a stock solution of 17 mg/mL of Dexamethasone was prepared on by diluting 6.8 mg Dexamethasone in 400 µL 96% ethanol. For each day of dosing, a working solution is prepared by diluting the stock solution 100× in sterile PBS to obtain a final concentration of 0.17 mg/mL in a septum vial for intraperitoneal dosing. Dexamethasone-treated mice received 100 µL Dexamethasone i.p. (5 mL/kg of a 0.17 mg/mL solution). Frozen sucrose served as the negative control (vehicle). *Blautia* Strain A was dosed at 100 ul of bacterial cells at 1×10^10 CFU/ml p.o. daily. Dexamethasone (positive control), vehicle (negative control), and *Blautia* Strain A were dosed daily.

O$_n$ day 8, mice were challenged intradermally (i.d.) with 10 µg KLH in saline (in a volume of 10 µL) in the right ear and a control in the left ear. Inflammatory responss were measured using methods known in the art. Ear pinna thickness was measured at 48 hours following antigen challenge (FIG. 1). As determinend by ear thickness, *Blautia* Strain A was as efficacious as Dexamethasone at suppressing inflammation compared to mice that received vehicle alone.

The efficacy of *Blautia* Strain A may be studied further using varied timing and varied doses. For instance, treatment with *Blautia* Strain A-containing bacterial composition may be initiated at some point, either around the time of priming or around the time of DTH challenge. For example, *Blautia* strain A (1×10$^9$ CFU per mouse per day) may be administered at the same time as the subcutaneous injections (day 0), or they may be administered prior to, or upon, intradermal injection. *Blautia* strain A is administered at varied doses and at defined intervals. For example, some mice are intravenously injected with *Blautia* strain A at a range of between 1×10$^4$ and 5×10$^9$ bacterial cells per mouse. While some mice will receive *Blautia* strain A through i.v. injection, other mice may receive *Blautia* strain A through intraperitoneal (i.p.) injection, subcutaneous (s.c.) injection, nasal route administration, oral gavage, topical administration, intradermal (i.d.) injection, or other means of administration. Some mice may receive *Blautia* strain A every day (e.g. starting on day 0), while others may receive *Blautia* strain A at alternative intervals (e.g. every other day, or once every three days). Additional groups of mice may receive some ratio of bacterial cells to *Blautia* strain A. The bacterial cells may be live, dead, or weakened. The bacterial cells may be harvested fresh (or frozen) and administered, or they may be irradiated or heat-killed prior to administration.

For example, some groups of mice may receive between $1\times10^4$ and $5\times10^9$ bacterial cells in an administration separate from, or comingled with, the *Blautia* strain A administration. As with the *Blautia* strain A, bacterial cell administration may be varied by route of administration, dose, and schedule. This can include oral gavage, i.v. injection, i.p. injection, i.d. injection, topical administration, or nasal route administration.

Some groups of mice may be treated with anti-inflammatory agent(s) (e.g. anti-CD 154, blockade of members of the TNF family, or other treatment), and/or an appropriate control (e.g. vehicle or control antibody) at various timepoints and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics.

Study animals may be sacrificed by exsanguination from the orbital plexus under $CO_2/O_2$ anesthesia, followed by cervical dislocation on day 10. For serum preparation, the blood samples are allowed to clot before centrifuging. The sera are transferred into clean tubes, each animal in a separate tube. Following exsanguination, of all animals both ears (each ear in a separate vial), the spleen, the mesenteric lymph nodes (MLN), the entire small intestine, and the colon are collected in cryovials, snap frozen and stored at $<-70°$ C.

Tissues may be dissociated using dissociation enzymes according to the manufacturer's instructions. Cells are stained for analysis by flow cytometry using techniques known in the art. Staining antibodies can include anti-CD 11 c (dendritic cells), anti-CD80, anti-CD86, anti-CD40, anti-MHCII, anti-CD8a, anti-CD4, and anti-CD 103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD1 1b, MHCII, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-lb, IFNy, GM-CSF, G-CSF, M-CSF, MIG, IP10, MIPlb, RANTES, and MCP-1. Cytokine analysis may be carried out on immune cells obtained from lymph nodes or other tissue, and/or on purified CD45+ infiltrated immune cells obtained ex vivo. Finally, immunohistochemistry is carried out on various tissue sections to measure T cells, macrophages, dendritic cells, and checkpoint molecule protein expression.

Example 2: An Evaluation of Test Articles in the Modulation of DSS-induced Colitis in C57BL/6 Mice Dextran sulfate sodium (DSS)-induced colitis is a well-studied animal model of colitis, as reviewed by Randhawa et al. (A review on chemical-induced inflammatory bowel disease models in rodents. Korean J Physiol Pharmacol. 2014. 18(4): 279-288; see also Chassaing et al. Dextran sulfate sodium (DSS)-induced colitis in mice. Curr Protoc Immunol. 2014 Feb. 4; 104: Unit 15.25). In this model, mice are treated with DSS in drinking water, resulting in diarrhea and weight loss.

Figure 2:
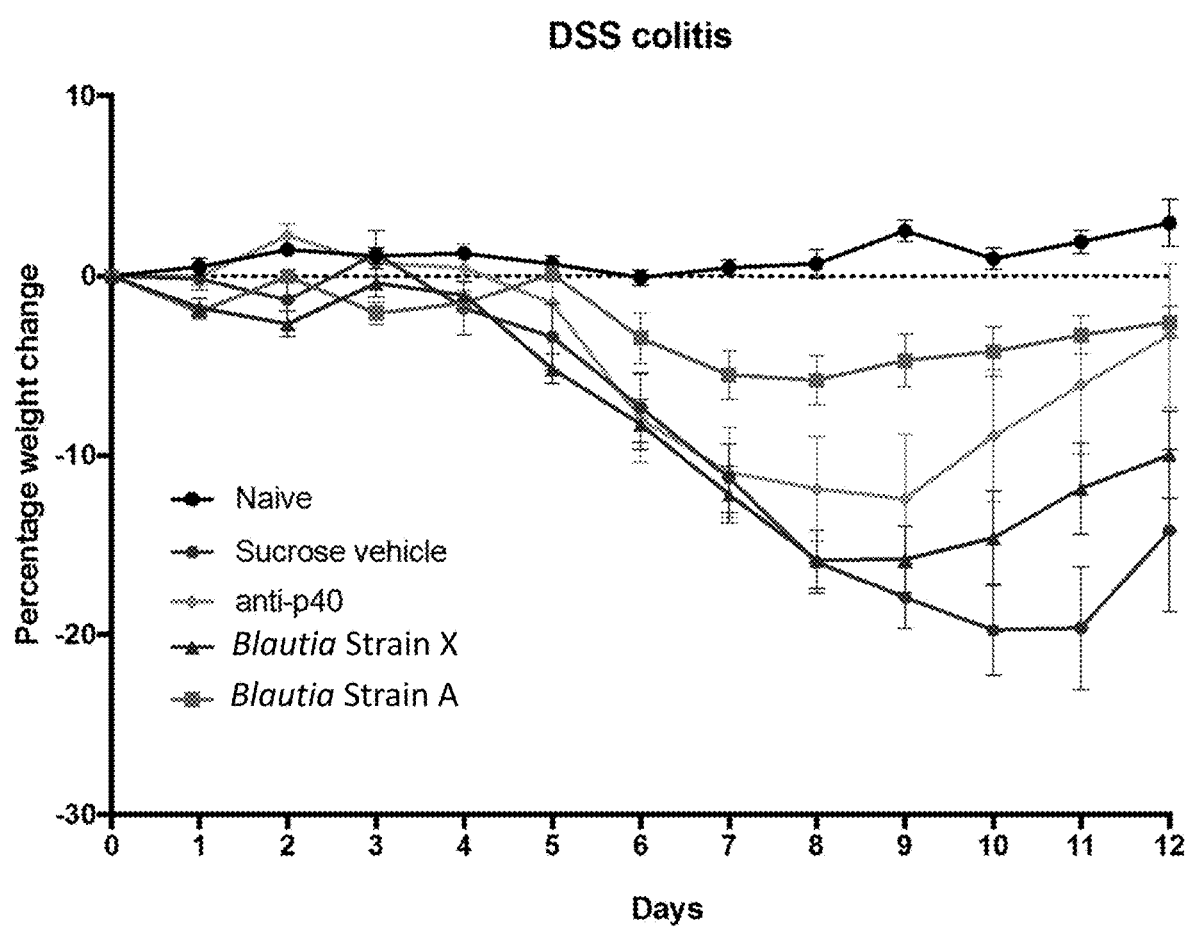
FIG. 2 is a line graphing showing percent weight change in acute DSS-induced colitis model over a 12 day period for *Blautia* Strain A in comparison to another *Blautia* strain (*Blautia* Strain X), positive control (anti-p40), and negative control (Sucrose vehicle). The *Blautia* Strain A group showed less weight change than the anti-p40 antibody (positive control).

Groups of mice were treated with DSS to induce colitis as known in the art (Randhawa et al. 2014; Chassaing et al. 2014; see also Kim et al. Investigating intestinal inflammation in DSS-induced model of IBD. J Vis Exp. 2012. 60: 3678). For example, colitis was induced in mice by exposure to 3% DSS-treated drinking water from Day 0 to Day 5. One group did not receive DSS and served as naive controls. Animals were dosed with sucrose vehicle (negative control), *Blautia* Strain A ($1\times10^9$ CFU per mouse per day), *Blautia* Strain X ($1\times10^9$ CFU per mouse per day), or anti-p40 positive control (administered i.p. on days 0, 3, 7, and 10). All animals were weighed daily. As measured by decrease in weight loss, *Blautia* Strain A was more efficacious than either anti-p40 (positive control), or *Blautia* Strain X (FIG. 2).

In other studies, treatment with *Blautia* Strain A-containing bacterial composition may be initiated at some point, either on day 1 of DSS administration, or sometime thereafter. For example, *Blautia* strain A may be administered at the same time as DSS initiation (day 1), or they may be administered upon the first signs of disease (e.g. weight loss or diarrhea), or during the stages of severe colitis. Mice may be observed daily for weight, morbidity, survival, presence of diarrhea and/or bloody stool.

*Blautia* strain A is administered at varied doses, varied intervals, and/or varied routes of administration. For example, some mice are intravenously injected with *Blautia* strain A at a dose of between $1\times10^4$ and $5\times10^9$ bacterial cells per mouse. While some mice will receive *Blautia* strain A through i.v. injection, other mice may receive *Blautia* strain A through intraperitoneal (i.p.) injection, subcutaneous (s.c.) injection, nasal route administration, oral gavage, or other means of administration. Some mice may receive *Blautia* strain A every day (e.g. starting on day 1), while others may receive *Blautia* strain A at alternative intervals (e.g. every other day, or once every three days). Additional groups of mice may receive some ratio of bacterial cells to *Blautia* strain A. The bacterial cells may be live, dead, or weakened. The bacterial cells may be harvested fresh (or frozen) and administered, or they may be irradiated or heat-killed prior to administration.

*Blautia* Strain A-containing bacterial compositions may be tested for their efficacy in a mouse model of DSS-induced colitis, either alone or in combination with whole bacterial cells, with or without the addition of other anti-inflammatory agents.

For example, some groups of mice may receive between $1\times10^4$ and $5\times10^9$ bacterial cells in an administration separate from, or comingled with, the *Blautia* strain A administration. As with the *Blautia* strain A, bacterial cell administration may be varied by route of administration, dose, and schedule. This can include oral gavage, i.v. injection, i.p. injection, or nasal route administration.

Some groups of mice may be treated with additional anti-inflammatory agent(s) (e.g. anti-CD 154, blockade of members of the TNF family, or other treatment), and/or an appropriate control (e.g. vehicle or control antibody) at various timepoints and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some mice receive DSS without receiving antibiotics beforehand.

At various timepoints, mice undergo video endoscopy using a small animal endoscope (Karl Storz Endoskipe, Germany) under isoflurane anesthesia. Still images and video will be recorded to evaluate the extent of colitis and the response to treatment. Colitis will be scored using criteria known in the art. Fecal material will be collected for study.

The gastrointestinal (GI) tract, lymph nodes, and/or other tissues may be removed for ex vivo histological, cytokine and/or flow cytometric analysis using methods known in the art. For example, tissues are harvested and may be dissociated using dissociation enzymes according to the manufacturer's instructions. Cells are stained for analysis by flow cytometry using techniques known in the art. Staining antibodies can include anti-CD 11 c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD1 lb, MHCII, CD206, CD40, CSF1R, PD-L1, Gr-1, F4/80). In addition to immunophenotyping, serum cytokines are analyzed including, but not limited to, TNFa, L-17, IL-13, IL-12p70, IL12p40, IL-10, IL-6, IL-5, IL-4, IL-2, IL-lb, IFNy, GM-CSF, G-CSF, M-CSF, MIG, IP10, MIPlb, RANTES, and MCP-1. Cytokine analysis may be carried out on immune cells obtained from lymph nodes or other tissue, and/or on purified CD45+GI tract-infiltrated immune cells obtained ex vivo. Finally, immunohistochemistry is carried out on various tissue sections to measure T cells, macrophages, dendritic cells, and checkpoint molecule protein expression.

In order to examine the impact and longevity of disease protection, rather than being sacrificed, some mice may be rechallenged with a disease trigger. Mice will be analyzed for susceptibility to colitis severity following rechallenge.

Following sacrifice, the colon, small intestine, spleen, and mesenteric lymph nodes may be collected from all animals, and blood collected for analysis.

Example 3: *Blautia* Strain A in a Mouse Model of Experimental Autoimmune Encephalomyelitis (EAE)

EAE is a well-studied animal model of multiple sclerosis, as reviewed by Constantinescu et al. (Experimental autoimmune encephalomyelitis (EAE) as a model for multiple sclerosis (MS). Br J Pharmacol. 2011 October; 164(4): 1079-1106). It can be induced in a variety of mouse and rat strains using different myelin-associated peptides, by the adoptive transfer of activated encephalitogenic T cells, or the use of TCR transgenic mice susceptible to EAE, as discussed in Mangalam et al. (Two discreet subsets of CD8+ T cells modulate $PLP_{91-110}$ induced experimental autoimmune encephalomyelitis in HLA-DR3 transgenic mice. J Autoimmun. 2012 June; 38(4): 344-353).

*Blautia* Strain A-containing bacterial compositions are tested for their efficacy in the rodent model of EAE, either alone or in combination with whole bacterial cells, with or without the addition of other anti-inflammatory treatments. For example, female 6-8 week old C57Bl/6 mice are obtained from Taconic (Germantown, N.Y.). Groups of mice will be administered two subcutaneous (s.c.) injections at two sites on the back (upper and lower) of 0.1 ml myelin oligodentrocyte glycoprotein 35-55 (MOG35-55; 100 ug per injection; 200 ug per mouse (total 0.2 ml per mouse)), emulsified in Complete Freund's Adjuvant (CFA; 2-5 mg killed *mycobacterium tuberculosis* H37Ra/ml emulsion). Approximately 1-2 hours after the above, mice are intraperitoneally (i.p.) injected with 200 ng Pertussis toxin (PTx) in 0.1 ml PBS (2 ug/ml). An additional IP injection of PTx is administered on day 2. Alternatively, an appropriate amount of an alternative myelin peptide (e.g. proteolipid protein (PLP)) will be used to induce EAE. Some animals will serve as naive controls. EAE severity will be assessed and a disability score will be assigned daily beginning on day 4 according to methods known in the art (Mangalam et al. 2012).

Treatment with *Blautia* Strain A-containing bacterial composition is initiated at some point, either around the time of immunization or following EAE immunization. For example, *Blautia* Strain A-containing bacterial composition may be administered at the same time as immunization (day 1), or they may be administered upon the first signs of disability (e.g. limp tail), or during severe EAE. *Blautia* Strain A-containing bacterial compositions are administered at varied doses and at defined intervals. For example, some mice are intravenously injected with effective doses of *Blautia* Strain A. For example, mice may receive between $1 \times 10^4$ and $5 \times 10^9$ bacterial cells per mouse. While some mice will receive *Blautia* strain A through i.v. injection, other mice may receive *Blautia* through intraperitoneal (i.p.) injection, subcutaneous (s.c.) injection, nasal route administration, oral gavage, or other means of administration. Some mice may receive *Blautia* strain A every day (e.g. starting on day 1), while others may receive *Blautia* strain A at alternative intervals (e.g. every other day, or once every three days). Additional groups of mice may receive some ratio of bacterial cells to *Blautia* strain A. The bacterial cells may be live, dead, or weakened. The bacterial cells may be harvested fresh (or frozen) and administered, or they may be irradiated or heat-killed prior to administration.

For example, some groups of mice may receive between $1 \times 10^4$ and $5 \times 10^9$ bacterial cells in an administration separate from, or comingled with, the *Blautia* strain A administration. As with the *Blautia* strain A, bacterial cell administration may be varied by route of administration, dose, and schedule. This can include oral gavage, i.v. injection, i.p. injection, subcutaneous (s.c.) injection, or nasal route administration.

Some groups of mice may be treated with additional anti-inflammatory agent(s) or EAE therapeutic(s) (e.g. anti-CD 154, blockade of members of the TNF family, Vitamin D, or other treatment), and/or an appropriate control (e.g. vehicle or control antibody) at various time points and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics.

At various time points, mice are sacrificed and sites of inflammation (e.g. brain and spinal cord), lymph nodes, or other tissues may be removed for ex vivo histological, cytokine and/or flow cytometric analysis using methods known in the art. For example, tissues are dissociated using dissociation enzymes according to the manufacturer's instructions. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-lb, IFNy, GM-CSF, G-CSF, M-CSF, MIG, IP10, MIPlb, RANTES, and MCP-1. Cytokine analysis may be carried out on immune cells obtained from lymph nodes or other tissue, and/or on purified CD45+ central nervous system (CNS)-infiltrated immune cells obtained ex vivo. Finally, immunohistochemistry is carried out on various tissue sections to measure T cells, macrophages, dendritic cells, and checkpoint molecule protein expression.

In order to examine the impact and longevity of disease protection, rather than being sacrificed, some mice may be rechallenged with a disease trigger (e.g. activated encephalitogenic T cells or re-injection of EAE-inducing peptides). Mice will be analyzed for susceptibility to disease and EAE severity following rechallenge.

Example 4: *Blautia* Strain A in a Mouse Model of Collagen-induced Arthritis (CIA)

Collagen-induced arthritis (CIA) is an animal model commonly used to study rheumatoid arthritis (RA), as described by Caplazi et al. (Mouse models of rheumatoid arthritis. Veterinary Pathology. Sep. 1, 2015. 52(5): 819-826) (see also Brand et al. Collagen-induced arthritis. Nature Protocols. 2007. 2: 1269-1275; Pietrosimone et al. Collagen-induced arthritis: a model for murine autoimmune arthritis. Bio Protoc. 2015 Oct. 20; 5(20): e1626).

Among other versions of the CIA rodent model, one model involves immunizing HLA-DQ8 Tg mice with chick type II collagen as described by Taneja et al. (J. Immunology. 2007. 56: 69-78; see also Taneja et al. J. Immunology 2008. 181: 2869-2877; and Taneja et al. Arthritis Rheum., 2007. 56: 69-78). Purification of chick CII has been described by Taneja et al. (Arthritis Rheum., 2007. 56: 69-78). Mice are monitored for CIA disease onset and progression following immunization, and severity of disease is evaluated and "graded" as described by Wooley, J. Exp. Med. 1981. 154: 688-700.

Mice are immunized for CIA induction and separated into various treatment groups. *Blautia* Strain A-containing bacterial compositions are tested for their efficacy in CIA, either alone or in combination with whole bacterial cells, with or without the addition of other anti-inflammatory treatments.

Treatment with *Blautia* Strain A-containing bacterial composition is initiated either around the time of immunization with collagen or post-immunization. For example, in some groups, *Blautia* strain A may be administered at the same time as immunization (day 1), or *Blautia* strain A may be administered upon first signs of disease, or upon the onset of severe symptoms. *Blautia* strain A is administered at varied doses and at defined intervals.

For example, some mice are intravenously injected with *Blautia* strain A at a dose of between $1 \times 10^4$ and $5 \times 10^9$ bacterial cells per mouse. While some mice will receive *Blautia* strain A through i.v. injection, other groups of mice may receive *Blautia* strain A through intraperitoneal (i.p.) injection, subcutaneous (s.c.) injection, nasal route administration, oral gavage, or other means of administration. Some mice may receive *Blautia* strain A every day (e.g. starting on day 1), while others may receive *Blautia* strain A at alternative intervals (e.g. every other day, or once every three days). Additional groups of mice may receive some ratio of bacterial cells to *Blautia* strain A. The bacterial cells may be live, dead, or weakened. The bacterial cells may be harvested fresh (or frozen) and administered, or they may be irradiated or heat-killed prior to administration.

For example, some groups of mice may receive between $1 \times 10^4$ and $5 \times 10^9$ bacterial cells in an administration separate from, or comingled with, the *Blautia* strain A administration. As with the *Blautia* strain A, bacterial cell administration may be varied by route of administration, dose, and schedule. This can include oral gavage, i.v. injection, i.p. injection, subcutaneous (s.c.) injection, intradermal (i.d.) injection, or nasal route administration.

Some groups of mice may be treated with additional anti-inflammatory agent(s) or CIA therapeutic(s) (e.g. anti-CD 154, blockade of members of the TNF family, Vitamin D, or other treatment), and/or an appropriate control (e.g. vehicle or control antibody) at various time points and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics.

At various time points, serum samples are obtained to assess levels of anti-chick and anti-mouse CII IgG antibodies using a standard ELISA (Batsalova et al. Comparative analysis of collagen type II-specific immune responses during development of collagen-induced arthritis in two B10 mouse strains. Arthritis Res Ther. 2012. 14(6): R237). Also, some mice are sacrificed and sites of inflammation (e.g. synovium), lymph nodes, or other tissues may be removed for ex vivo histological, cytokine and/or flow cytometric analysis using methods known in the art. The synovium and synovial fluid will be analyzed for plasma cell infiltration and the presence of antibodies using techniques known in the art. In addition, tissues are dissociated using dissociation enzymes according to the manufacturer's instructions to examine the profiles of the cellular infiltrates. Cells are stained for analysis by flow cytometry using techniques known in the art. Staining antibodies can include anti-CD 11 c (dendritic cells), anti-CD80, anti-CD86, anti-CD40, anti-MHCII, anti-CD8a, anti-CD4, and anti-CD 103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD1 lb, MHCII, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-lb, IFNy, GM-CSF, G-CSF, M-CSF, MIG, IP10, MIPlb, RANTES, and MCP-1. Cytokine analysis may be carried out on immune cells obtained from lymph nodes or other tissue, and/or on purified CD45+ synovium-infiltrated immune cells obtained ex vivo. Finally, immunohistochemistry is carried out on various tissue sections to measure T cells, macrophages, dendritic cells, and checkpoint molecule protein expression.

In order to examine the impact and longevity of disease protection, rather than being sacrificed, some mice may be rechallenged with a disease trigger (e.g. activated re-injection with CIA-inducing peptides). Mice will be analyzed for susceptibility to disease and CIA severity following rechallenge.

Example 5: *Blautia* Strain A in a Mouse Model of Type 1 Diabetes (T1D)

Type 1 diabetes (T1D) is an autoimmune disease in which the immune system targets the islets of Langerhans of the pancreas, thereby destroying the body's ability to produce insulin.

There are various models of animal models of T1D, as reviewed by Belle et al. (Mouse models for type 1 diabetes. Drug Discov Today Dis Models. 2009; 6(2): 41-45; see also Aileen J F King. The use of animal models in diabetes research. Br J Pharmacol. 2012 June; 166(3): 877-894. There are models for chemically-induced T1D, pathogen-induced T1D, as well as models in which the mice spontaneously develop T1D.

*Blautia* Strain A-containing bacterial compositions are tested for their efficacy in a mouse model of T1D, either alone or in combination with whole bacterial cells, with or without the addition of other anti-inflammatory treatments.

Depending on the method of T1D induction and/or whether T1D development is spontaneous, treatment with *Blautia* strain A is initiated at some point, either around the time of induction or following induction, or prior to the onset (or upon the onset) of spontaneously-occurring T1D. *Blautia* strain A is administered at varied doses and at defined intervals. For example, some mice are intravenously injected with *Blautia* strain A at a dose of between $1 \times 10^4$ and $5 \times 10^9$ bacterial cells per mouse. Other mice may receive 25, 50, or 100 mg of *Blautia* strain A per mouse. While some mice will receive *Blautia* strain A through i.v. injection, other mice may receive *Blautia* strain A through intraperitoneal (i.p.) injection, subcutaneous (s.c.) injection, nasal route administration, oral gavage, or other means of administration. Some mice may receive *Blautia* strain A every day, while others may receive *Blautia* strain A at alternative intervals (e.g. every other day, or once every three days). Additional groups of mice may receive some ratio of bacterial cells to *Blautia* strain A. The bacterial cells may be live, dead, or weakened. The bacterial cells may be harvested fresh (or frozen) and administered, or they may be irradiated or heat-killed prior to administration.

For example, some groups of mice may receive between $1 \times 10^4$ and $5 \times 10^9$ bacterial cells in an administration separate from, or comingled with, the *Blautia* strain A administration. As with the *Blautia* strain A, bacterial cell administration may be varied by route of administration, dose, and schedule. This can include oral gavage, i.v. injection, i.p. injection, or nasal route administration.

Some groups of mice may be treated with additional treatments and/or an appropriate control (e.g. vehicle or control antibody) at various timepoints and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics.

Blood glucose is monitored biweekly prior to the start of the experiment. At various timepoints thereafter, nonfasting blood glucose is measured. At various timepoints, mice are sacrificed and site the pancreas, lymph nodes, or other tissues may be removed for ex vivo histological, cytokine and/or flow cytometric analysis using methods known in the art. For example, tissues are dissociated using dissociation enzymes according to the manufacturer's instructions. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD1 lb, MHCII, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-lb, IFNy, GM-CSF, G-CSF, M-CSF, MIG, IP10, MIPlb, RANTES, and MCP-1. Cytokine analysis may be carried out on immune cells obtained from lymph nodes or other tissue, and/or on purified tissue-infiltrating immune cells obtained ex vivo. Finally, immunohistochemistry is carried out on various tissue sections to measure T cells, macrophages, dendritic cells, and checkpoint molecule protein expression. Antibody production may also be assessed by ELISA.

In order to examine the impact and longevity of disease protection, rather than being sacrificed, some mice may be rechallenged with a disease trigger, or assessed for susceptibility to relapse. Mice will be analyzed for susceptibility to diabetes onset and severity following rechallenge (or spontaneously-occurring relapse).

Example 6: *Blautia* Strain A in a Mouse Model of Primary Sclerosing Cholangitis (PSC)

Primary Sclerosing Cholangitis (PSC) is a chronic liver disease that slowly damages the bile ducts and leads to end-stage cirrhosis. It is associated with inflammatory bowel disease (IBD).

There are various animal models for PSC, as reviewed by Fickert et al. (Characterization of animal models for primary sclerosing cholangitis (PSC). J Hepatol. 2014 June 60(6): 1290-1303; see also Pollheimer and Fickert. Animal models in primary biliary cirrhosis and primary sclerosing cholangitis. Clin Rev Allergy Immunol. 2015 June 48(2-3): 207-17). Induction of disease in PSC models includes chemical induction (e.g. 3,5-diethoxycarbonyl-1,4-dihydrocollidine (DDC)-induced cholangitis), pathogen-induced (e.g. *Cryptosporidium parvum*), experimental biliary obstruction (e.g. common bile duct ligation (CBDL)), and transgenic mouse model of antigen-driven biliary injury (e.g. Ova-Bil transgenic mice). For example, bile duct ligation is performed as described by Georgiev et al. (Characterization of time-related changes after experimental bile duct ligation. Br J Surg. 2008. 95(5): 646-56), or disease is induced by DCC exposure as described by Fickert et al. (A new xenobiotic-induced mouse model of sclerosing cholangitis and biliary fibrosis. Am J Path. Vol 171(2): 525-536.

*Blautia* Strain A-containing bacterial compositions are tested for their efficacy in a mouse model of PSC, either alone or in combination with whole bacterial cells, with or without the addition of some other therapeutic agent.

DCC-induced Cholangitis

For example, 6-8 week old C57bl/6 mice are obtained from Taconic or other vendor. Mice are fed a 0.1% DCC-supplemented diet for various durations. Some groups will receive DCC-supplement food for 1 week, others for 4 weeks, others for 8 weeks. Some groups of mice may receive a DCC-supplemented diet for a length of time and then be allowed to recover, thereafter receiving a normal diet. These mice may be studied for their ability to recover from disease and/or their susceptibility to relapse upon subsequent exposure to DCC. Treatment with *Blautia* strain A is initiated at some point, either around the time of DCC-feeding or subsequent to initial exposure to DCC. For example, *Blautia* strain A may be administered on day 1, or they may be administered sometime thereafter. *Blautia* strain A is administered at varied doses and at defined intervals. For example, some mice are intravenously injected with *Blautia* strain A at a range between $1 \times 10^4$ and $5 \times 10^9$ bacterial cells per mouse. Other mice may receive 25, 50, 100 mg of *Blautia* strain A per mouse. While some mice will receive *Blautia* strain A through i.v. injection, other mice may receive *Blautia* strain A through i.p. injection, subcutaneous (s.c.) injection, nasal route administration, oral gavage, or other means of administration. Some mice may receive *Blautia* strain A every day (e.g. starting on day 1), while others may receive *Blautia* strain A at alternative intervals (e.g. every other day, or once every three days). Additional groups of mice may receive some ratio of bacterial cells to *Blautia* strain A. The bacterial cells may be live, dead, or weakened. The bacterial cells may be harvested fresh (or frozen), and administered, or they may be irradiated or heat-killed prior to administration. For example, some groups of mice may receive between $1 \times 10^4$ and $5 \times 10^9$ bacterial cells in an administration separate from, or comingled with, the *Blautia* strain A administration. As with *Blautia* strain A, bacterial cell administration may be varied by route of administration, dose, and schedule. This can include oral gavage, i.v. injection, i.p. injection, or nasal route administration. Some groups of mice may be treated with additional agents and/or an appropriate control (e.g. vehicle or antibody) at various timepoints and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics. At various timepoints, serum samples are analyzed for ALT, AP, bilirubin, and serum bile acid (BA) levels.

At various timepoints, mice are sacrificed, body and liver weight are recorded, and sites of inflammation (e.g. liver, small and large intestine, spleen), lymph nodes, or other tissues may be removed for ex vivo histolomorphological characterization, cytokine and/or flow cytometric analysis using methods known in the art (see Fickert et al. Characterization of animal models for primary sclerosing cholangitis (PSC)). J Hepatol. 2014. 60(6): 1290-1303). For example, bile ducts are stained for expression of ICAM-1, VCAM-1, MadCAM-1. Some tissues are stained for histological examination, while others are dissociated using dissociation enzymes according to the manufacturer's instructions. Cells are stained for analysis by flow cytometry using techniques known in the art. Staining antibodies can include anti-CD 11 c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD1 lb, MHCII, CD206, CD40, CSF1R, PD-L1, Gr-1, F4/80), as well as adhesion molecule expression (ICAM-1, VCAM-1, MadCAM-1). In addition to immunophenotyping, serum cytokines are analyzed including, but not limited to, TNFa, IL-17, IL-13, IL-12p70, IL12p40, IL-10, IL-6, IL-5, IL-4, IL-2, IL-lb, IFNy, GM-CSF, G-CSF, M-CSF, MIG, IP10, MIPlb, RANTES, and MCP-1. Cytokine analysis may be carried out on immune cells obtained from lymph nodes or other tissue, and/or on purified CD45+ bile duct-infiltrated immune cells obtained ex vivo.

Liver tissue is prepared for histological analysis, for example, using Sirius-red staining followed by quantification of the fibrotic area. At the end of the treatment, blood is collected for plasma analysis of liver enzymes, for example, AST or ALT, and to determine Bilirubin levels. The hepatic content of Hydroxyproline can be measured using established protocols. Hepatic gene expression analysis of inflammation and fibrosis markers may be performed by qRT-PCR using validated primers. These markers may include, but are not limited to, MCP-1, alpha-SMA, Col11a1, and TIMP-. Metabolite measurements may be performed in plasma, tissue and fecal samples using established metabolomics methods. Finally, immunohistochemistry is carried out on liver sections to measure neutrophils, T cells, macrophages, dendritic cells, or other immune cell infiltrates.

In order to examine the impact and longevity of disease protection, rather than being sacrificed, some mice may be rechallenged with DCC at a later time. Mice will be analyzed for susceptibility to cholangitis and cholangitis severity following rechallenge.

BDL-induced Cholangitis

Alternatively, *Blautia* Strain A-containing bacterial compositions are tested for their efficacy in BDL-induced cholangitis. For example, 6-8 week old C57Bl/6J mice are obtained from Taconic or other vendor. After an acclimation period the mice are subjected to a surgical procedure to perform a bile duct ligation (BDL). Some control animals receive a sham surgery. The BDL procedure leads to liver injury, inflammation and fibrosis within 7-21 days.

Treatment with *Blautia* strain A is initiated at some point, either around the time of surgery or some time following the surgery. *Blautia* strain A is administered at varied doses and at defined intervals. For example, some mice are intravenously injected with *Blautia* strain A at a range between $1 \times 10^4$ and $5 \times 10^9$ bacterial cells per mouse. Other mice may receive 25, 50, or 100 mg of *Blautia* strain A per mouse. While some mice will receive *Blautia* strain A through i.v. injection, other mice may receive *Blautia* strain A through i.p. injection, subcutaneous (s.c.) injection, nasal route administration, oral gavage, or other means of administration. Some mice receive *Blautia* strain A every day (e.g. starting on day 1), while others may receive *Blautia* strain A at alternative intervals (e.g. every other day, or once every three days). Additional groups of mice may receive some ratio of bacterial cells to *Blautia* strain A. The bacterial cells may be live, dead, or weakened. They bacterial cells may be harvested fresh (or frozen), and administered, or they may be irradiated or heat-killed prior to administration. For example, some groups of mice may receive between $1 \times 10^4$ and $5 \times 10^9$ bacterial cells in an administration separate from, or comingled with, the *Blautia* strain A administration. As with *Blautia* strain A, bacterial cell administration may be varied by route of administration, dose, and schedule. This can include oral gavage, i.v. injection, i.p. injection, or nasal route administration. Some groups of mice may be treated with additional agents and/or an appropriate control (e.g. vehicle or antibody) at various timepoints and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics. At various timepoints, serum samples are analyzed for ALT, AP, bilirubin, and serum bile acid (BA) levels.

At various timepoints, mice are sacrificed, body and liver weight are recorded, and sites of inflammation (e.g. liver, small and large intestine, spleen), lymph nodes, or other tissues may be removed for ex vivo histolomorphological characterization, cytokine and/or flow cytometric analysis using methods known in the art (see Fickert et al. Characterization of animal models for primary sclerosing cholangitis (PSC)). J Hepatol. 2014. 60(6): 1290-1303). For example, bile ducts are stained for expression of ICAM-1, VCAM-1, MadCAM-1. Some tissues are stained for histological examination, while others are dissociated using dissociation enzymes according to the manufacturer's instructions. Cells are stained for analysis by flow cytometry using techniques known in the art. Staining antibodies can include anti-CD 11 c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD1b, MHCII, CD206, CD40, CSF1R, PD-L1, Gr-1, F4/80), as well as adhesion molecule expression (ICAM-1, VCAM-1, MadCAM-1). In addition to immunophenotyping, serum cytokines are analyzed including, but not limited to, TNFa, IL-17, IL-13, IL-12p70, IL12p40, IL-10, IL-6, IL-5, IL-4, IL-2, IL-lb, IFNy, GM-CSF, G-CSF, M-CSF, MIG, IP10, MIPlb, RANTES, and MCP-1. Cytokine analysis may be carried out on immune cells obtained from lymph nodes or other tissue, and/or on purified CD45+ bile duct-infiltrated immune cells obtained ex vivo.

Liver tissue is prepared for histological analysis, for example, using Sirius-red staining followed by quantification of the fibrotic area. At the end of the treatment, blood is collected for plasma analysis of liver enzymes, for example, AST or ALT, and to determine Bilirubin levels. The hepatic content of Hydroxyproline can be measured using established protocols. Hepatic gene expression analysis of inflammation and fibrosis markers may be performed by qRT-PCR using validated primers. These markers may include, but are not limited to, MCP-1, alpha-SMA, Coll1a1, and TIMP-. Metabolite measurements may be performed in plasma, tissue and fecal samples using established metabolomics methods. Finally, immunohistochemistry is carried out on liver sections to measure neutrophils, T cells, macrophages, dendritic cells, or other immune cell infiltrates.

In order to examine the impact and longevity of disease protection, rather than being sacrificed, some mice may be analyzed for recovery.

Example 7: *Blautia* Strain a in a Mouse Model of Nonalcoholic Steatohepatitis (NASH)

Nonalcoholic Steatohepatitis (NASH) is a severe form of Nonalcoholic Fatty Liver Disease (NAFLD), where buildup of hepatic fat (steatosis) and inflammation lead to liver injury and hepatocyte cell death (ballooning).

There are various animal models of NASH, as reviewed by Ibrahim et al. (Animal models of nonalcoholic steatohepatitis: Eat, Delete, and Inflame. Dig Dis Sci. 2016 May 61(5): 1325-1336; see also Lau et al. Animal models of non-alcoholic fatty liver disease: current perspectives and recent advances 2017 January 241(1): 36-44).

*Blautia* Strain A-containing bacterial compositions tested for their efficacy in a mouse model of NASH, either alone or in combination with whole bacterial cells, with or without the addition of another therapeutic agent. For example, 8-10 week old C57Bl/6J mice, obtained from Taconic (Germantown, N.Y.), or other vendor, are placed on a methionine choline deficient (MCD) diet for a period of 4-8 weeks during which NASH features will develop, including steatosis, inflammation, ballooning and fibrosis.

Treatment with *Blautia* strain A is initiated at some point, either at the beginning of the diet, or at some point following diet initiation (for example, one week after). For example, *Blautia* strain A may be administered starting in the same day as the initiation of the MCD diet. *Blautia* strain A is administered at varied doses and at defined intervals. For example, some mice are intravenously injected with *Blautia* strain A at doses between $1 \times 10^4$ and $5 \times 10^9$ bacterial cells per mouse. Other mice may receive 25, 50, or 100 mg of *Blautia* strain A per mouse. While some mice will receive *Blautia* strain A through i.v. injection, other mice may receive *Blautia* strain A through intraperitoneal (i.p.) injection, subcutaneous (s.c.) injection, nasal route administration, oral gavage, or other means of administration. Some mice may receive *Blautia* strain A every day (e.g. starting on day 1), while others may receive *Blautia* strain A at alternative intervals (e.g. every other day, or once every three days). Additional groups of mice may receive some ratio of bacterial cells to *Blautia* strain A. The bacterial cells may be live, dead, or weakened. The bacterial cells may be harvested fresh (or frozen) and administered, or they may be irradiated or heat-killed prior to administration.

For example, some groups of mice may receive between $1 \times 10^4$ and $5 \times 10^9$ bacterial cells in an administration separate from, or comingled with, the *Blautia* strain A administration. As with the *Blautia* strain A, bacterial cell administration may be varied by route of administration, dose, and schedule. This can include oral gavage, i.v. injection, i.p. injection, or nasal route administration. Some groups of mice may be treated with additional NASH therapeutic(s) (e.g., FXR agonists, PPAR agonists, CCR2/5 antagonists or other treatment) and/or appropriate control at various timepoints and effective doses.

At various timepoints and/or at the end of the treatment, mice are sacrificed and liver, intestine, blood, feces, or other tissues may be removed for ex vivo histological, biochemical, molecular or cytokine and/or flow cytometry analysis using methods known in the art. For example, liver tissues are weighed and prepared for histological analysis, which may comprise staining with H&E, Sirius Red, and determination of NASH activity score (NAS). At various timepoints, blood is collected for plasma analysis of liver enzymes, for example, AST or ALT, using standards assays. In addition, the hepatic content of cholesterol, triglycerides, or fatty acid acids can be measured using established protocols. Hepatic gene expression analysis of inflammation, fibrosis, steatosis, ER stress, or oxidative stress markers may be performed by qRT-PCR using validated primers. These markers may include, but are not limited to, IL-6, MCP-1, alpha-SMA, Colllal, CHOP, and NRF2. Metabolite measurements may be performed in plasma, tissue and fecal samples using established biochemical and mass-spectrometry-based metabolomics methods. Serum cytokines are analyzed including, but not limited to, TNFa, IL-17, IL-13, IL-12p70, IL12p40, IL-10, IL-6, IL-5, IL-4, IL-2, IL-lb, IFNy, GM-CSF, G-CSF, M-CSF, MIG, IP10, MIPlb, RANTES, and MCP-1. Cytokine analysis may be carried out on immune cells obtained from lymph nodes or other tissue, and/or on purified CD45+ bile duct-infiltrated immune cells obtained ex vivo. Finally, immunohistochemistry is carried out on liver or intestine sections to measure neutrophils, T cells, macrophages, dendritic cells, or other immune cell infiltrates.

In order to examine the impact and longevity of disease protection, rather than being sacrificed, some mice may be analyzed for recovery.

Figure 3A:
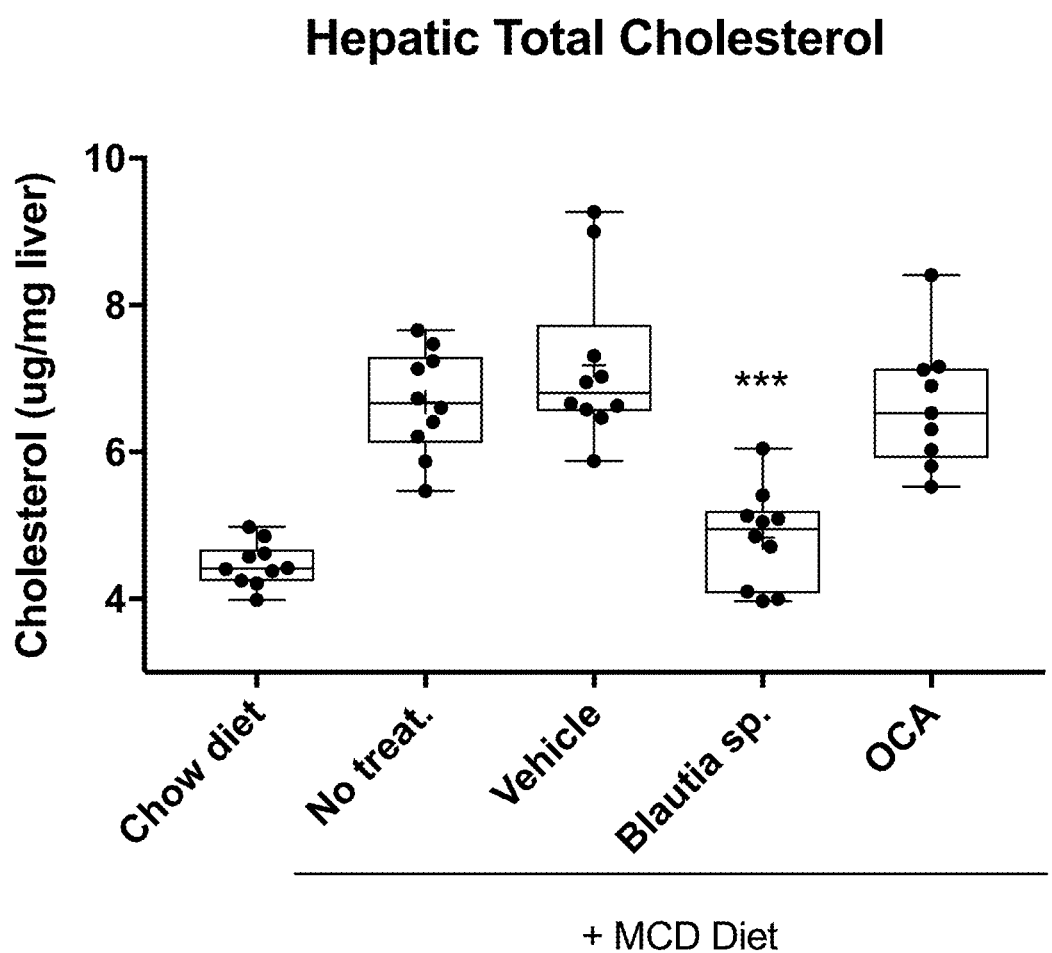
FIG. 3A shows the effect of *Blautia*, and obeticholic acid (OCA) on hepatic total cholesterol in mice that were fed an MCD diet.
Figure 3B:
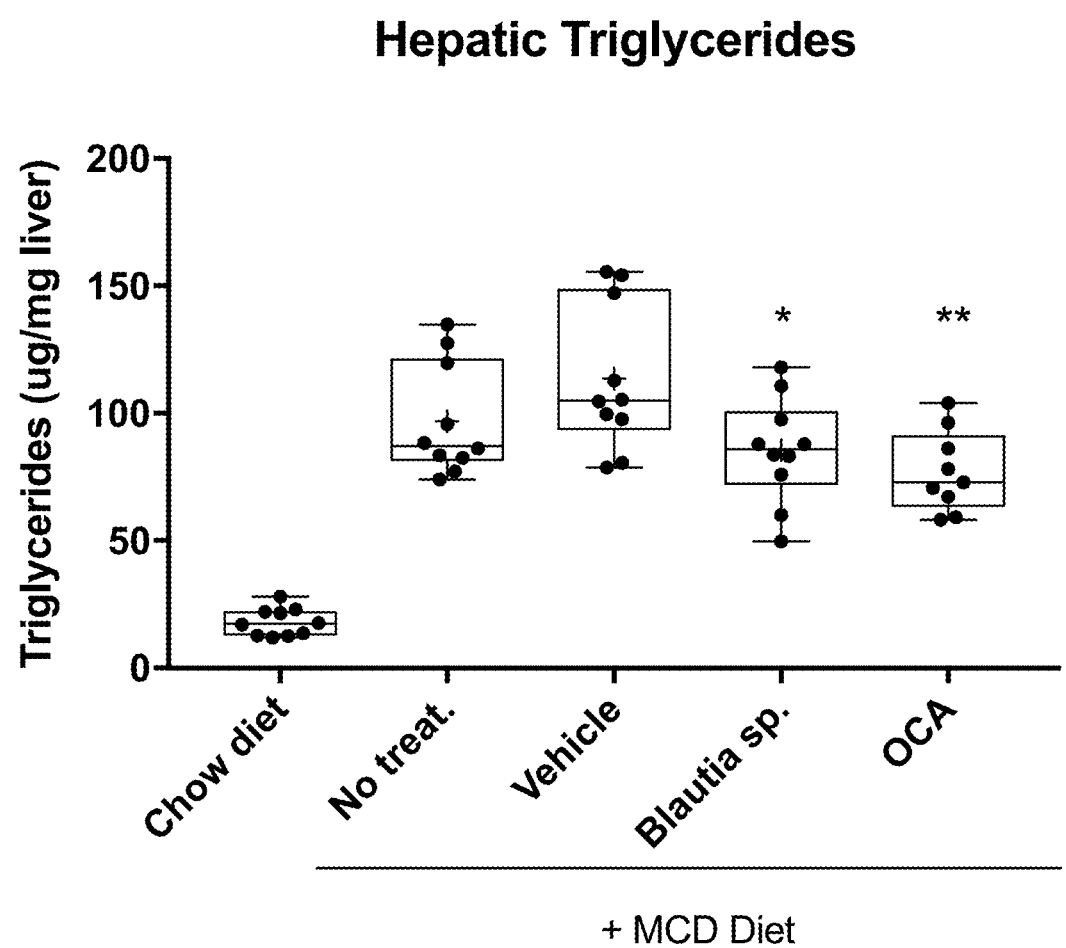
FIG. 3B shows the effect of *Blautia*, and obeticholic acid (OCA) on hepatic triglycerides in mice that were fed an MCD diet.
Figure 3C:
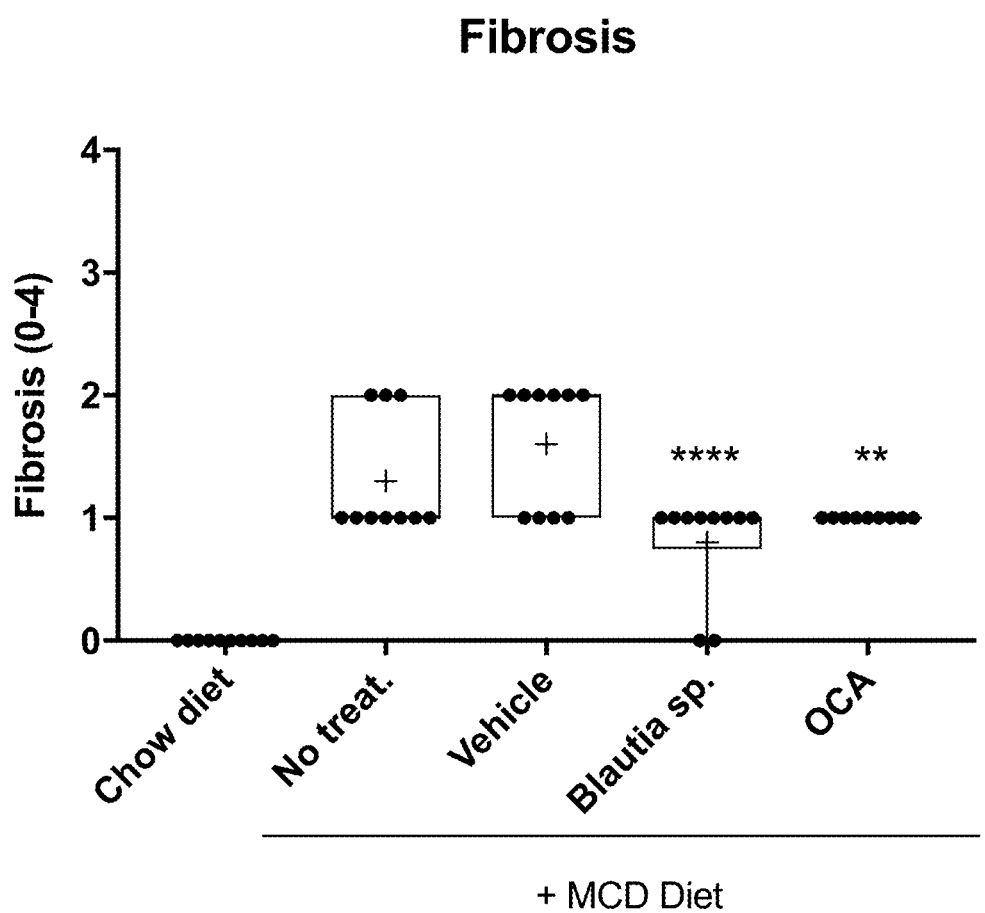
FIG. 3C shows the effect of *Blautia* and obeticholic acid (OCA) on fibrosis score in mice that were fed an MCD diet.
Figure 3D:
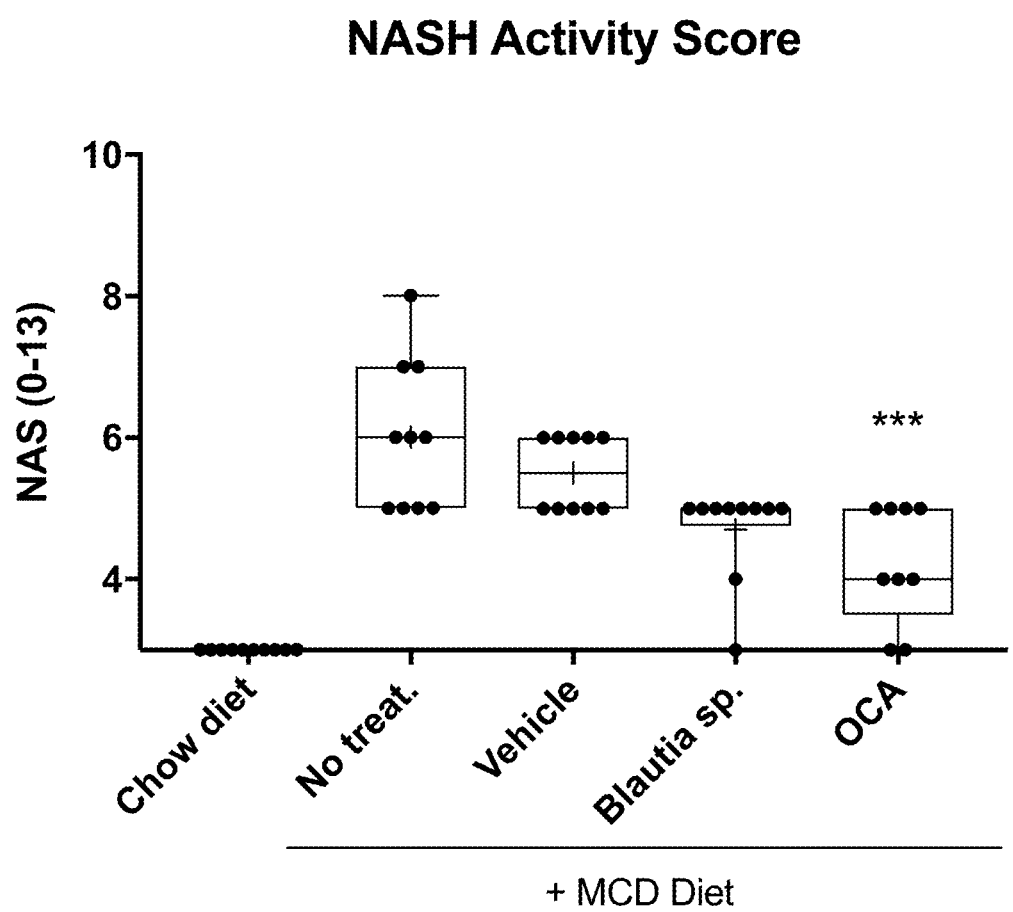
FIG. 3D shows that *Blautia* is efficacious at reducing the NASH activity score (NAS) in mice receiving a methionine choline deficient (MCD) diet, which induces NASH symptoms.

FIG. 3A shows the effect of *Blautia*, and obeticholic acid (OCA) on hepatic total cholesterol in mice that were fed an MCD diet. FIG. 3B shows the effect of *Blautia*, and obeticholic acid (OCA) on hepatic triglycerides in mice that were fed an MCD diet. FIG. 3C shows the effect of *Blautia* and obeticholic acid (OCA) on fibrosis score in mice that were fed an MCD diet. FIG. 3D shows that *Blautia* is efficacious at reducing the NASH activity score (NAS) in mice receiving a methionine choline deficient (MCD) diet, which induces NASH symptoms.

Example 8: *Blautia* Strain a in a Mouse Model of Psoriasis

Psoriasis is a T-cell-mediated chronic inflammatory skin disease. So-called "plaque-type" psoriasis is the most common form of psoriasis and is typified by dry scales, red plaques, and thickening of the skin due to infiltration of immune cells into the dermis and epidermis. Several animal models have contributed to the understanding of this disease, as reviewed by Gudjonsson et al. (Mouse models of psoriasis. J Invest Derm. 2007. 127: 1292-1308; see also van der Fits et al. Imiquimod-induced psoriasis-like skin inflammation in mice is mediated via the IL-23/IL-17 axis. J. Immunol. 2009 May 1. 182(9): 5836-45).

Psoriasis can be induced in a variety of mouse models, including those that use transgenic, knockout, or xenograft models, as well as topical application of imiquimod (IMQ), a TLR7/8 ligand.

*Blautia* Strain A-containing bacterial compositions are tested for their efficacy in the mouse model of psoriasis, either alone or in combination with whole bacterial cells, with or without the addition of other anti-inflammatory treatments. For example, 6-8 week old C57Bl/6 or Balb/c mice are obtained from Taconic (Germantown, N.Y.), or other vendor. Mice are shaved on the back and the right ear. Groups of mice receive a daily topical dose of 62.5 mg of commercially available IMQ cream (5%) (Aldara; 3M Pharmaceuticals). The dose is applied to the shaved areas for 5 or 6 consecutive days. At regular intervals, mice are scored for erythema, scaling, and thickening on a scale from 0 to 4, as described by van der Fits et al. (2009). Mice are monitored for ear thickness using a Mitutoyo micrometer.

Treatment with *Blautia* strain A is initiated at some point, either around the time of the first application of IMQ, or something thereafter. For example, *Blautia* strain A may be administered at the same time as the subcutaneous injections (day 0), or they may be administered prior to, or upon, application. *Blautia* strain A is administered at varied doses and at defined intervals. For example, some mice are intravenously injected with *Blautia* strain A at a dose of between $1 \times 10^4$ and $5 \times 10^9$ bacterial cells per mouse. Other mice may receive 25, 50, or 100 mg of *Blautia* strain A per mouse. While some mice will receive *Blautia* strain A through i.v. injection, other mice may receive *Blautia* strain A through intraperitoneal (i.p.) injection, nasal route administration, oral gavage, topical administration, intradermal (i.d.) injection, subcutaneous (s.c.) injection, or other means of administration. Some mice may receive *Blautia* strain A every day (e.g. starting on day 0), while others may receive *Blautia* strain A at alternative intervals (e.g. every other day, or once every three days). Additional groups of mice may receive some ratio of bacterial cells to *Blautia* strain A. The bacterial cells may be live, dead, or weakened. The bacterial cells may be harvested fresh (or frozen) and administered, or they may be irradiated or heat-killed prior to administration.

For example, some groups of mice may receive between $1 \times 10^4$ and $5 \times 10^9$ bacterial cells in an administration separate from, or comingled with, the *Blautia* strain A administration. As with the *Blautia* strain A, bacterial cell administration may be varied by route of administration, dose, and schedule. This can include oral gavage, i.v. injection, i.p. injection, i.d. injection, s.c. injection, topical administration, or nasal route administration.

Some groups of mice may be treated with anti-inflammatory agent(s) (e.g. anti-CD 154, blockade of members of the TNF family, or other treatment), and/or an appropriate control (e.g. vehicle or control antibody) at various timepoints and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics.

At various timepoints, samples from back and ear skin are taken for cryosection staining analysis using methods known in the art. Other groups of mice are sacrificed and lymph nodes, spleen, mesenteric lymph nodes (MLN), the small intestine, colon, and other tissues may be removed for histology studies, ex vivo histological, cytokine and/or flow cytometric analysis using methods known in the art. Some tissues may be dissociated using dissociation enzymes according to the manufacturer's instructions. Cryosection samples, tissue samples, or cells obtained ex vivo are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD1 lb, MHCII, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-lb, IFNy, GM-CSF, G-CSF, M-CSF, MIG, IP10, MIPlb, RANTES, and MCP-1. Cytokine analysis may be carried out on immune cells obtained from lymph nodes or other tissue, and/or on purified CD45+ skin-infiltrated immune cells obtained ex vivo. Finally, immunohistochemistry is carried out on various tissue sections to measure T cells, macrophages, dendritic cells, and checkpoint molecule protein expression.

In order to examine the impact and longevity of psoriasis protection, rather than being sacrificed, some mice may be studied to assess recovery, or they may be rechallenged with IMQ. The groups of rechallenged mice will be analyzed for susceptibility to psoriasis and severity of response.

Example 9: *Blautia* Strain a in a Mouse Model of Collagen-induced Arthritis (CIA)

Collagen-induced arthritis (CIA) is an animal model commonly used to study rheumatoid arthritis (RA), as described by Caplazi et al. (Mouse models of rheumatoid arthritis. Veterinary Pathology. Sep. 1, 2015. 52(5): 819-826)

(see also Brand et al. Collagen-induced arthritis. Nature Protocols. 2007. 2: 1269-1275; Pietrosimone et al. Collagen-induced arthritis: a model for murine autoimmune arthritis. Bio Protoc. 2015 Oct. 20; 5(20): e1626).

Among other versions of the CIA rodent model, one model involves immunizing HLA-DQ8 Tg mice with chick type II collagen as described by Taneja et al. (J. Immunology. 2007. 56: 69-78; see also Taneja et al. J. Immunology 2008. 181: 2869-2877; and Taneja et al. Arthritis Rheum., 2007. 56: 69-78). Purification of chick CII has been described by Taneja et al. (Arthritis Rheum., 2007. 56: 69-78). Mice are monitored for CIA disease onset and progression following immunization, and severity of disease is evaluated and "graded" as described by Wooley, J. Exp. Med. 1981. 154: 688-700.

On Day 0, all mice are given a 0.05 mL intradermal/subcutaneous (ID/SC) injection of chicken type II collagen emulsified in complete Freund's adjuvant (CFA) at the base of the tail (source Hooke Labs). All animals are then given a second intradermal/subcutaneous injection of chicken type II collagen emulsified in Incomplete Freund's adjuvant (IFA) on day 21 of the study. An intraperitoneal injection of LPS is not included in this study. This paradigm results in inflammation of the joints beginning around day 28-35. Mice are evaluated for arthritis three times a week from day 21 until the study conclusion on Day 56. The evaluation involves scoring each paw separately on a scale of 0 to 4, where 0 is normal and 4 equates to severe swelling resulting in rigidity of the joint such that the animal does not put weight on that limb. Each animal therefore has a cumulative score of up to 16 for each day of evaluation. Paw swelling is evaluated by measurement of paw thickness in all 4 paws using digital calipers, once at baseline on Day −1, and once per week starting on Day 21 until the conclusion of the study on Day 56.

Animals are randomized into groups prior to the start of the study on Day 0. Test article dosing begins on Day 0 and consists of 100 ul of test article or vehicle being administered once daily (QD) via oral gavage through Day 56. Dexamethasone (0.5 mg/kg) is administered to a treatment group daily via oral gavage at a volume of 0.1 mL per 20 g. If excess weight loss is observed in this group, the concentration of dexamethasone is reduced for a short period of time until recovery. Mice are evaluated for arthritis scores three times a week until the conclusion of the study.

Terminal collections occur on Day 56, 2 hours after the final dose of test article. Upon sacrifice, blood is collected via cardiac puncture and serum prepared and stored at −80° C. until shipment to the sponsor. The two right paws (front and hind) are snap frozen, and the two left paws (front and hind) are stored in 10% neutral buffered formalin for 24 hours, and subsequently switched to 70% ethanol for storage for histological analysis. The snap frozen tissue is stored at −80° C. The spleen and inguinal lymph nodes are collected from each animal into separate tubes filled with complete RPMI media and stored on ice.

Mice are immunized for CIA induction and separated into various treatment groups. *Blautia* Strain A is tested for its efficacy in CIA, either alone or in combination with whole bacterial cells, with or without the addition of other anti-inflammatory treatments.

Treatment with *Blautia* Strain A is initiated either around the time of immunization with collagen or post-immunization. For example, in some groups, *Blautia* Strain A may be administered at the same time as immunization (day 1), or *Blautia* Strain A may be administered upon first signs of disease, or upon the onset of severe symptoms. *Blautia* Strain A is administered at varied doses and at defined intervals.

For example, some groups of mice may receive between $1 \times 10^4$ and $5 \times 10^9$ bacterial cells. Bacterial cell administration may be varied by route of administration, dose, and schedule. This can include oral gavage, i.v. injection, i.p. injection, subcutaneous (s.c.) injection, intradermal (i.d.) injection, or nasal route administration.

Some groups of mice may be treated with additional anti-inflammatory agent(s) or CIA therapeutic(s) (e.g. anti-CD 154, blockade of members of the TNF family, Vitamin D, or other treatment), and/or an appropriate control (e.g. vehicle or control antibody) at various timepoints and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics.

At various timepoints, serum samples are obtained to assess levels of anti-chick and anti-mouse CII IgG antibodies using a standard ELISA (Batsalova et al. Comparative analysis of collagen type II-specific immune responses during development of collagen-induced arthritis in two B10 mouse strains. Arthritis Res Ther. 2012. 14(6): R237). Also, some mice are sacrificed and sites of inflammation (e.g. synovium), lymph nodes, or other tissues may be removed for ex vivo histological, cytokine and/or flow cytometric analysis using methods known in the art. The synovium and synovial fluid are analyzed for plasma cell infiltration and the presence of antibodies using techniques known in the art. In addition, tissues are dissociated using dissociation enzymes according to the manufacturer's instructions to examine the profiles of the cellular infiltrates. Cells are stained for analysis by flow cytometry using techniques known in the art. Staining antibodies can include anti-CD 11 c (dendritic cells), anti-CD80, anti-CD86, anti-CD40, anti-MHCII, anti-CD8a, anti-CD4, and anti-CD 103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD1 1b, MHCII, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIPlb, RANTES, and MCP-1. Cytokine analysis may be carried out on immune cells obtained from lymph nodes or other tissue, and/or on purified CD45+ synovium-infiltrated immune cells obtained ex vivo. Finally, immunohistochemistry is carried out on various tissue sections to measure T cells, macrophages, dendritic cells, and checkpoint molecule protein expression.

In order to examine the impact and longevity of disease protection, rather than being sacrificed, some mice may be rechallenged with a disease trigger (e.g. activated re-injection with CIA-inducing peptides). Mice are analyzed for susceptibility to disease and CIA severity following rechallenge.

Example 10: Effect of *Blautia* on LGALS3 Gene Expression in a Mouse Model of Nonalcoholic Steatohepatitis (NASH)

As detailed in Example 7, *Blautia* bacterial cells is tested for their efficacy in a mouse model of NASH with or without the addition of another therapeutic agent. LGALS3 gene expression in treated mouse liver is assessed via whole transcriptome analysis using Applied Biosystems Clariom S microarrays (catalog #902930), according to manufacturer's instructions. The RNA used in the analysis is extracted from mouse liver tissue using Qiagen's RNeasy Plus Mini Kit (catalog #74136), according to manufacturer's instructions. Microarray data is analyzed with Thermo's Transcriptome Analysis Console (TAC) Software version 4.0. Gene expression levels are obtained after SST-RMA normalization and log 2 transformation of signal intensity values. Statistical analysis is performed by 1-way ANOVA with multiple comparisons to vehicle group by Sidak test, using GraphPad Prism 7 software.

LGALS3 encodes a member of the galectin family of carbohydrate binding proteins. Members of this protein family have an affinity for beta-galactosides. Excess fatty acid oxidation and generation of reactive carbonyls with formation of advanced lipoxidation endproducts (ALEs) is involved in nonalcoholic steatohepatitis (NASH) by triggering inflammation, hepatocyte injury, and fibrosis. Ablation of the ALE-receptor galectin-3 prevents experimental NASH by reducing receptor-mediated ALE clearance and downstream events (Iacobini C., et al., J. Hepatol. 2011; 54(5):975-83). Galectin-3 ablation protects from diet-induced NASH by decreasing hepatic ALE accumulation, with attenuation of inflammation, hepatocyte injury, and fibrosis. It also reduces up-regulation of lipid synthesis and oxidation causing less fat deposition, oxidative stress, and possibly insulin resistance. Galectin-3 is a major receptor involved in ALE uptake by the liver.

Example 11: A Mouse Lung Cancer Model

*Blautia* is tested for its efficacy in the mouse lung cancer model, either alone or in combination with other cancer therapies, including checkpoint inhibitor(s). Mice are divided into groups receiving *Blautia* Strain A, and/or other *Blautia* strain, with or without checkpoint inhibitor treatment. As described in Example 9, *Blautia* is administered at varied doses at defined intervals. For example, some mice receive a bacterial strain (p.o.) on the day following tumor cell injection (day 1). Some mice receive seven (7) consecutive doses of a bacterial strain (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

$1\times10^6$ LLC1 cells, or an appropriate number of lung cancer cells from another lung cancer cell line, are injected into the hind flank of syngeneic mice. Tumors from the various treatment groups are measured with calipers at regular intervals. As described in Example 9, some mice are sacrificed for ex vivo tumor analysis using flow cytometry. Other mice may be rechallenged with tumor cell injection into the contralateral flank to determine the impact of the immune system's memory response on tumor growth.

Example 12: A Mouse Breast Cancer Model

A *Blautia* strain is tested for its efficacy in the mouse breast cancer model, either alone or in combination with other cancer therapies, including checkpoint inhibitor(s). Mice are divided into groups receiving *Blautia* Strain A, and/or other *Blautia* strain, with or without checkpoint inhibitor treatment. As described in Example 9, a bacterial strain is administered at varied doses at defined intervals. For example, some mice receive a bacterial strain (p.o.) on the day following tumor cell injection (day 1). Some mice receive seven (7) consecutive doses of a bacterial strain (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

4T1 mouse mammary carcinoma cells are obtained from ATCC and $1\times10^6$ cells in 50 ul PBS are injected subcutaneously into one or both hind limbs of Balb/c female mice (as described by Wang et al. 2003, Systemic dissemination of viral vectors during intratumoral injection. Molecular Cancer Therapeutics; 2(11)). Alternatively, EMT6 mouse mammary carcinoma cells are obtained from ATCC and $1\times10^6$ cells in 50 µl PBS are injected subcutaneously into one or both of the hind limbs of Balb/c female mice 6-8 weeks old (as described by Guo et al. 2014, Combinatorial Photothermal and Immuno Cancer Therapy Using Chitosan-Coated Hollow Copper Sulfide Nanoparticles. ASC Nano.; 8(6): 5670-5681). In addition, other available mouse mammary cell lines may be used.

Tumors from the various treatment groups are measured with calipers at regular intervals. As described in Example 9, *Blautia* is administered at varied doses at defined intervals. For example, some mice are sacrificed for ex vivo tumor analysis using flow cytometry. Other mice may be rechallenged with tumor cell injection into the contralateral flank to determine the impact of the immune system's memory response on tumor growth.

Alternatively, 4T1 cells can be used in an orthotopic murine model of breast cancer as described by Tao et al. (Tao et al. 2008. Imagable 4T1 model for the study of late stage breast cancer. 8: 288). Mice are sacrificed for ex vivo tumor analysis. Tumors are analyzed by flow cytometry and immunohistochemistry.

Example 13: A Mouse Pancreatic Cancer Model

A *Blautia* strain is tested for its efficacy in the mouse model of pancreatic cancer, either alone or in combination with other cancer therapies, including checkpoint inhibitor(s). Mice are divided into groups receiving a bacterial strain, with or without checkpoint inhibitor treatment. As described in Example 9, some mice receive *Blautia* (p.o.) on the day following tumor cell injection (day 1). Some mice receive seven (7) consecutive doses of a bacterial strain (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

Panc02 cells are maintained in DMEM, supplemented with 10% fetal calf serum and 1% penicillin/streptomycin, and incubated at 37° C. at 5% CO2. Female 8-10 week-old C57Bl/6 mice are obtained from Charles River, Inc. or other certified vendor. Female C57Bl/6 mice are injected subcutaneously into the right hind flank with $1\times10^6$ Panc02 cells. This protocol is based on standard Panc02 tumor models (Maletzki et al. 2008. Pancreatic cancer regression by intratumoral injection of live *streptococcus pyogenes* in a syngeneic mouse model. Gut. 57:483-491). Tumors from the various treatment groups are measured with calipers at regular intervals. As described in Example 9, some mice are sacrificed for ex vivo tumor analysis using flow cytometry, while other mice are rechallenged to determine the impact of the memory response on tumor growth.

Alternatively, Panc02, 6606PDA, or Capan-1 cells lines can be used in an orthotopic murine model of pancreatic cancer as described by Partecke et al. (Partecke et al. 2011. A syngeneic orthotopic murine model of pancreatic adenocarcinoma in the C57/B16 mouse using the Panc02 and 6606PDA cell lines. Eur. Surg. Res. 47(2):98-107) or Chai et al. (Chai et al. 2013. Bioluminescent orthotopic model of pancreatic cancer progression. J. Vis. Exp. 76: 50395). Mice are sacrificed for ex vivo tumor analysis. Tumors are analyzed by flow cytometry and immunohistochemistry.

Example 14: A Mouse Model of Hepatocellular Carcinoma

A *Blautia* strain is tested for its efficacy in the mouse model of hepatocellular carcinoma, either alone or in combination with other cancer therapies, including checkpoint inhibitor(s). Mice are divided into groups receiving a bacterial strain, with or without checkpoint inhibitor treatment. As described in Example 9, *Blautia* is administered at varied doses at defined intervals. For example, some mice receive *Blautia* (p.o.) on the day following tumor cell injection (day 1). Some mice receive seven (7) consecutive doses of a bacterial strain (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

Hepatocellular carcinoma is induced in mice by subcutaneous inoculation of 1×10$^6$ Hepa129 cells (obtained from NCI or other source), or an appropriate number of cells from other hepatocellular carcinoma cell line (as described by Gonzalez-Carmona et al. 2008. CD40 ligand-expressing dendritic cells induce regression of hepatocellular carcinoma by activating innate and acquired immunity in vivo. Hepatology. 48(1):157-168). Tumor cells are inoculated into one or both flanks. Tumors from the various treatment groups are measured with calipers at regular intervals. As described in Example 9, some mice are sacrificed for ex vivo tumor analysis using flow cytometry, while other mice are rechallenged to determine the impact of the memory response on tumor growth.

Example 15: A Mouse Lymphoma Model

A *Blautia* strain is tested for its efficacy in the mouse model of lymphoma, either alone or in combination with other cancer therapies, including checkpoint inhibitor(s). For example, mice are divided into groups receiving *Blautia* Strain A and/or other *Blautia* strain, with or without checkpoint inhibitor treatment. As described in Example 9, A bacterial strain is administered at varied doses at defined intervals. For example, some mice receive A bacterial strain (p.o.) on the day following tumor cell injection (day 1). Some mice receive seven (7) consecutive doses of A bacterial strain (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

One lymphoma cell line is the A20 lymphoma, although other lymphoma cell lines may be used with syngeneic mice. A20 lymphoma cells are obtained from ATCC and 5×10$^6$ cells in 50 ul PBS are injected subcutaneously into one or both of the hind limbs of Balb/c female mice (as described by Houot et al. 2009. T-cell modulation combined with intratumoral CpG cures lymphoma in a mouse model without the need for chemotherapy. Blood. 113(15): 3546-3552). Tumors from the various treatment groups are measured with calipers at regular intervals. As described in Example 9, some mice are sacrificed for ex vivo tumor analysis using flow cytometry, while other mice are rechallenged to determine the impact of the memory response on tumor growth.

Example 16: A Mouse Prostate Cancer Model

A *Blautia* strain is tested for its efficacy in the mouse model of prostate cancer, either alone or in combination with other cancer therapies, including checkpoint inhibitor(s). Mice are divided into groups receiving *Blautia* Strain A, and/or other *Blautia* strain, with or without checkpoint inhibitor treatment. As described in Example 9, *Blautia* is administered at varied doses at defined intervals. For example, some mice receive A bacterial strain (p.o.) on the day following tumor cell injection (day 1). Some mice receive seven (7) consecutive doses of *Blautia* (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

Mouse prostate cancer cells (1×10$^5$ RM-1 cells or an appropriate number of cells from another prostate cancer cell line) are injected into syngeneic mice. Tumors from the various treatment groups are measured with calipers at regular intervals. As described in Example 9, some mice are sacrificed for ex vivo tumor analysis using flow cytometry, while other mice are rechallenged to determine the impact of the memory response on tumor growth.

Example 17: A Mouse Plasmacytoma Model

A bacterial strain is tested for its efficacy in the mouse model of plasmacytoma, either alone or in combination with other cancer therapies, including checkpoint inhibitor(s). Mice are divided into groups receiving *Blautia* Strain A, and/or other *Blautia* strain, with or without checkpoint inhibitor treatment. As described in Example 9, A bacterial strain is administered at varied doses at defined intervals. For example, some mice receive A bacterial strain (p.o.) on the day following tumor cell injection (day 1). Some mice receive seven (7) consecutive doses of *Blautia* (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

Mineral Oil Induced Model of Plasmacytoma

To examine the efficacy of *Blautia* in a plasmacytoma or multiple myeloma model, mice are injected intraperitoneally three times with 500 ul of 2,6,10,12-tetramethylpentadecane ("pristane oil") at various time points between 0 and 60 days, as described by Potter et al. 1983. Peritoneal plasmacytomagenesis in mice: comparison of different pristane dose regimens. J. Natl. Cancer Inst. 71(2):391-5 (see also Lattanzio et al. 1997. Defective Development of Pristane-Oil Induced Plasmacytomas in Interleukin-6-Deficient BALB/C Mice. Am. J. Pathology: 151(3):689696). Progression of disease is measured by the degree of abdominal swelling and immune cells and particles in the ascites. Ascites fluid is analyzed for immune cell phenotype by flow cytometry.

Cell-Line Induced Model of Plasmacytoma

To examine the efficacy of *Blautia* in a plasmacytoma or multiple myeloma model, either MOPC-104E cells or J558 plasmacytoma cells (TIB-6 ATCC) are injected subcutaneously into one or more hind flanks of Balb/c mice ($5 \times 10^6$ cells), based on model described by Bhoopalam et al. 1980. Effect of dextran-S (alpha, 1-3 dextran) on the growth of plasmacytomas MOPC-104E and J558. J. Immunol. 125(4): 1454-8 (see also Wang et al. 2015. IL-10 enhances CTL-mediated tumor rejection by inhibiting highly suppressive CD4+ T cells and promoting CTL persistence in a murine model of plasmacytoma. Oncolmmunology. 4(7): e1014232-1-9). Mice are divided into groups receiving *Blautia* by oral gavage, and with or without checkpoint inhibitor treatment. Tumors from the various treatment groups are measured with calipers at regular intervals. As described in Example 9, some mice are sacrificed for ex vivo tumor analysis using flow cytometry, while other mice are rechallenged to determine the impact of the memory response on tumor growth.

Example 18: A SCID Mouse Model of Mouse Myeloma

*Blautia* is tested for its efficacy in the SCID mouse model of myeloma, either alone or in combination with other cancer therapies, including checkpoint inhibitor(s). Mice are divided into groups receiving *Blautia* Strain A, and/or other *Blautia* strain, with or without checkpoint inhibitor treatment. As described in Example 9, *Blautia* is administered at varied doses at defined intervals. For example, some mice receive A bacterial strain (p.o.) on the day following tumor cell injection (day 1). Some mice receive seven (7) consecutive doses of Veillonalla (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

To examine the efficacy of *Blautia* using a human plasma cell leukemia, $1 \times 10^7$ human myeloma cell lines, ARH77 cells (ARH77-ATCC CRL-1621, or an appropriate number of cells from another myeloma cell line such as KPMM2) are used. Myeloma cells are injected subcutaneously into one or both hind flanks of SCID mice (See Caers et al. 2004. Of mice and men: disease models of multiple myeloma. Drug Discovery Today: Disease Models. 1(4):373-380. Tumors from the various treatment groups are measured with calipers at regular intervals. As described in Example 9, some mice are sacrificed for ex vivo tumor analysis using flow cytometry, while other mice are rechallenged to determine the impact of the memory response on tumor growth.

Example 19: A Mouse Renal Cell Carcinoma Model

A bacterial strain is tested for its efficacy in the mouse model of renal cell carcinoma, either alone or in combination with other cancer therapies, including checkpoint inhibitor(s). Mice are divided into groups receiving *Blautia* Strain A, and/or other *Blautia* strain, with or without checkpoint inhibitor treatment. As described in Example 9, *Blautia* may be administered at varied doses at defined intervals. For example, some mice receive A bacterial strain (p.o.) on the day following tumor cell injection (day 1). Some mice receive seven (7) consecutive doses of a *Blautia* bacterial strain (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

To examine the efficacy of *Blautia* in a mouse model of renal cell carcinoma, Renca cells (ATCC CRL-2947) or other renal cell carcinoma cells are injected subcutaneously into one or both flanks of 7-8 week old syngeneic Balb/c mice ($5 \times 10^6$ in 0.1 ml PBS). Tumors from the various treatment groups are measured with calipers at regular intervals. As described in Example 9, some mice are sacrificed for ex vivo tumor analysis using flow cytometry, while other mice are rechallenged to determine the impact of the memory response on tumor growth.

Example 20: A Mouse Bladder Cancer Model

A bacterial strain is tested for its efficacy in the mouse model of bladder cancer, either alone or in combination with other cancer therapies, including checkpoint inhibitor(s). Mice are divided into groups receiving *Blautia* Strain A, and/or other *Blautia* strain, with or without checkpoint inhibitor treatment. As described in Example 9, *Blautia* may be administered at varied doses at defined intervals. For example, some mice receive A bacterial strain (p.o.) on the day following tumor cell injection (day 1). Some mice receive seven (7) consecutive doses of a bacterial strain (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

On the day of inoculation, MBT-2 cells (or other bladder cancer cell line) are harvested and resuspended in 1:1 PBS/Matrigel mixture. $2 \times 10^5$ MBT-2 cells are suspended in 100 ul of mixture and injected subcutaneously into one or both hind flanks of syngeneic mice. Tumors are measured with calipers at regular intervals.

As described in Example 9, some mice are sacrificed for ex vivo tumor analysis using flow cytometry, while other mice are rechallenged to determine the impact of the memory response on tumor growth.

Example 21: A Mouse Model for Colorectal Carcinoma

A bacterial strain is tested for its efficacy in the mouse model of colorectal carcinoma, either alone or in combination with other cancer therapies, including checkpoint inhibitor(s). Mice are divided into groups receiving *Blautia* Strain A, and/or other *Blautia* strain, with or without checkpoint inhibitor treatment. As described in Example 9, Veillonalla may be administered at varied doses at defined intervals. For example, some mice receive A bacterial strain (p.o.) on the day following tumor cell injection (day 1). Some mice receive seven (7) consecutive doses of A bacterial strain (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

Female 6-8 week old Balb/c mice are obtained from Taconic (Germantown, N.Y.). 100,000 CT-26 colorectal tumor cells (ATCC CRL-2638) were resuspended in sterile PBS and inoculated in the presence of 50% Matrigel. CT-26 tumor cells were subcutaneously injected into one hind flank of each mouse. Treatment with a *Blautia* strain is initiated at some point following tumor cell inoculation at varied doses and at defined intervals. For example, some mice receive between 1-5×10^9 CFU (100 μl final volume) per dose. Possible routes of administration include oral gavage (p.o.), intravenous injection, intratumoral injection (IT) or peritumoral or subtumoral or subcutaneous injection. In order to assess the systemic anti-tumoral effects of *Blautia* treatment, additional mice may be inoculated with tumor cells in the contralateral (untreated, second) flank prior to IT, peritumoral, or subtumoral treatment with *Blautia* in the first flank.

Tumors from the various treatment groups are measured with calipers at regular intervals. As described in Example 9, some mice are sacrificed for ex vivo tumor analysis using flow cytometry, while other mice are rechallenged to determine the impact of the memory response on tumor growth.

Example 22: Manufacturing Conditions

Enriched media is used to grow and prepare the bacterium for in vitro and in vivo use. For example, media may contain sugar, yeast extracts, plant based peptones, buffers, salts, trace elements, surfactants, anti-foaming agents, and vitamins. Composition of complex components such as yeast extracts and peptones may be undefined or partially defined (including approximate concentrations of amino acids, sugars etc.). Microbial metabolism may be dependent on the availability of resources such as carbon and nitrogen. Various sugars or other carbon sources may be tested. Alternatively, media may be prepared and the selected bacterium grown as shown by Saarela et al., *J. Applied Microbiology*. 2005. 99: 1330-1339, which is hereby incorporated by reference. Influence of fermentation time, cryoprotectant and neutralization of cell concentrate on freeze-drying survival, storage stability, and acid and bile exposure of the selected bacterium produced without milk-based ingredients.

At large scale, the media is sterilized. Sterilization may be by Ultra High Temperature (UHT) processing. The UHT processing is performed at very high temperature for short periods of time. The UHT range may be from 135-180° C. For example, the medium may be sterilized from between 10 to 30 seconds at 135° C.

Inoculum can be prepared in flasks or in smaller bioreactors and growth is monitored. For example, the inoculum size may be between approximately 0.5 and 3% of the total bioreactor volume. Depending on the application and need for material, bioreactor volume can be at least 2 L, 10 L, 80 L, 100 L, 250 L, 1000 L, 2500 L, 5000 L, 10,000 L.

Before the inoculation, the bioreactor is prepared with medium at desired pH, temperature, and oxygen concentration. The initial pH of the culture medium may be different that the process set-point. pH stress may be detrimental at low cell centration; the initial pH could be between pH 7.5 and the process set-point. For example, pH may be set between 4.5 and 8.0. During the fermentation, the pH can be controlled through the use of sodium hydroxide, potassium hydroxide, or ammonium hydroxide. The temperature may be controlled from 25° C. to 45° C., for example at 37° C. Anaerobic conditions are created by reducing the level of oxygen in the culture broth from around 8 mg/L to 0 mg/L. For example, nitrogen or gas mixtures (N2, CO2, and H2) may be used in order to establish anaerobic conditions. Alternatively, no gases are used and anaerobic conditions are established by cells consuming remaining oxygen from the medium. Depending on strain and inoculum size, the bioreactor fermentation time can vary. For example, fermentation time can vary from approximately 5 hours to 48 hours.

Reviving microbes from a frozen state may require special considerations. Production medium may stress cells after a thaw; a specific thaw medium may be required to consistently start a seed train from thawed material. The kinetics of transfer or passage of seed material to fresh medium, for the purposes of increasing the seed volume or maintaining the microbial growth state, may be influenced by the current state of the microbes (ex. exponential growth, stationary growth, unstressed, stressed).

Inoculation of the production fermenter(s) can impact growth kinetics and cellular activity. The initial state of the bioreactor system must be optimized to facilitate successful and consistent production. The fraction of seed culture to total medium (e.g. a percentage) has a dramatic impact on growth kinetics. The range may be 1-5% of the fermenter's working volume. The initial pH of the culture medium may be different from the process set-point. pH stress may be detrimental at low cell concentration; the initial pH may be between pH 7.5 and the process set-point. Agitation and gas flow into the system during inoculation may be different from the process set-points. Physical and chemical stresses due to both conditions may be detrimental at low cell concentration.

Process conditions and control settings may influence the kinetics of microbial growth and cellular activity. Shifts in process conditions may change membrane composition, production of metabolites, growth rate, cellular stress, etc. Optimal temperature range for growth may vary with strain. The range may be 20-40° C. Optimal pH for cell growth and performance of downstream activity may vary with strain. The range may be pH 5-8. Gasses dissolved in the medium may be used by cells for metabolism. Adjusting concentrations of $O_2$, $CO_2$, and $N_2$ throughout the process may be required. Availability of nutrients may shift cellular growth. Microbes may have alternate kinetics when excess nutrients are available.

The state of microbes at the end of a fermentation and during harvesting may impact cell survival and activity. Microbes may be preconditioned shortly before harvest to better prepare them for the physical and chemical stresses involved in separation and downstream processing. A change in temperature (often reducing to 20-5° C.) may reduce cellular metabolism, slowing growth (and/or death) and physiological change when removed from the fermenter. Effectiveness of centrifugal concentration may be influenced by culture pH. Raising pH by 1-2 points can improve effectiveness of concentration but can also be detrimental to cells. Microbes may be stressed shortly before harvest by increasing the concentration of salts and/or sugars in the medium. Cells stressed in this way may better survive freezing and lyophilization during downstream.

Separation methods and technology may impact how efficiently microbes are separated from the culture medium. Solids may be removed using centrifugation techniques. Effectiveness of centrifugal concentration can be influenced by culture pH or by the use of flocculating agents. Raising pH by 1-2 points may improve effectiveness of concentration but can also be detrimental to cells. Microbes may be stressed shortly before harvest by increasing the concentration of salts and/or sugars in the medium. Cells stressed in this way may better survive freezing and lyophilization during downstream. Additionally, Microbes may also be separated via filtration. Filtration is superior to centrifugation techniques for purification if the cells require excessive g-minutes to successfully centrifuge. Excipients can be added before after separation. Excipients can be added for cryo protection or for protection during lyophilization. Excipients can include, but are not limited to, sucrose, trehalose, or lactose, and these may be alternatively mixed with buffer and anti-oxidants. Prior to lyophilization, droplets of cell pellets mixed with excipients are submerged in liquid nitrogen.

Harvesting can be performed by continuous centrifugation. Product may be resuspended with various excipients to a desired final concentration. Excipients can be added for cryo protection or for protection during lyophilization. Excipients can include, but are not limited to, sucrose, trehalose, or lactose, and these may be alternatively mixed with buffer and anti-oxidants. Prior to lyophilization, droplets of cell pellets mixed with excipients are submerged in liquid nitrogen.

Lyophilization of material, including live bacteria, begins with primary drying. During the primary drying phase, the ice is removed. Here, a vacuum is generated and an appropriate amount of heat is supplied to the material for the ice to sublime. During the secondary drying phase, product bound water molecules are removed. Here, the temperature is raised higher than in the primary drying phase to break any physico-chemical interactions that have formed between the water molecules and the product material. The pressure may also be lowered further to enhance desorption during this stage. After the freeze-drying process is complete, the chamber may be filled with an inert gas, such as nitrogen. The product may be sealed within the freeze dryer under dry conditions, preventing exposure to atmospheric water and contaminants.

INCORPORATION BY REFERENCE

All publications patent applications mentioned herein are hereby incorporated by reference in their entirety as if each individual publication or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a disease in a subject comprising administering to the subject a bacterial composition comprising a *Blautia* strain comprising at least 90% genomic, 16S or CRISPR sequence identity to the nucleotide sequence of the *Blautia* Strain A (ATCC Deposit Number PTA-125346).

2. The method of claim 1, wherein the *Blautia* strain is a strain comprising at least 99% genomic, 16S or CRISPR sequence identity to the nucleotide sequence of the *Blautia* Strain A (ATCC Deposit Number PTA-125346).

3. The method of claim 1, wherein the *Blautia* strain is the *Blautia* Strain A (ATCC Deposit Number PTA-125346).

4. The method of claim 1, wherein the disease is an immune disorder.

5. The method of claim 4, wherein the immune disorder is selected from: an allergic reaction, an inflammatory disease, an inflammatory bowel disease, Crohn's disease, ulcerative colitis, delayed-type hypersensitivity, autoimmune myocarditis, granulomas, peripheral neuropathies, Hashimoto's thyroiditis, inflammation of the colon, colitis, microscopic colitis, collagenous colitis, diversion colitis, chemical colitis, ischemic colitis, indeterminate colitis, atypical colitis, multiple sclerosis, Hashimoto's disease, an allergic disease, a food allergy, pollenosis, asthma, an infectious disease, an infection with Clostridium difficile, an inflammatory disease, a TNF-mediated inflammatory disease, an inflammatory disease of the gastrointestinal tract, pouchitis, a cardiovascular inflammatory condition, atherosclerosis, an inflammatory lung disease, chronic obstructive pulmonary disease, arthritis, osteoarthritis, rheumatoid arthritis, psoriatic arthritis, ankylosing spondylitis, acute and chronic infectious arthritis, arthritis associated with gout and pseudogout, juvenile idiopathic arthritis, tendonitis, synovitis, tenosynovitis, bursitis, fibrositis, fibromyalgia, epicondylitis, myositis, and osteitis, Paget's disease, osteitis pubis, osteitis fibrosa cystic, Ocular immune disorders, blepharitis, blepharochalasis, conjunctivitis, dacryoadenitis, keratitis, keratoconjunctivitis sicca (dry eye), scleritis, trichiasis, uveitis, nervous system immune, encephalitis, Guillain-Barre syndrome, meningitis, neuromyotonia, narcolepsy, multiple sclerosis, myelitis, schizophrenia, inflammation of the vasculature or lymphatic system, arthrosclerosis, arthritis, phlebitis, vasculitis, lymphangitis, digestive system immune disorders, cholangitis, cholecystitis, enteritis, enterocolitis, gastritis, gastroenteritis, ileitis, proctitis, irritable bowel syndrome, microscopic colitis, lymphocytic-plasmocytic enteritis, coeliac disease, collagenous colitis, lymphocytic colitis, eosinophilic enterocolitis, indeterminate colitis, pseudomembranous colitis (necrotizing colitis), ischemic inflammatory bowel disease, Behcet's disease, sarcoidosis, scleroderma, IBD-associated dysplasia, dysplasia associated masses or lesions, primary sclerosing cholangitis, reproductive system immune disorders, cervicitis, chorioamnionitis, endometritis, epididymitis, omphalitis, oophoritis, orchitis, salpingitis, tubo-ovarian abscess, urethritis, vaginitis, vulvitis, vulvodynia, autoimmune conditions, acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, diabetes mellitus type 1, giant cell arteritis, goodpasture's syndrome, Grave's disease, Guillain-Barre syndrome, Henoch-Schonlein purpura, Kawasaki's disease, lupus erythematosus, microscopic colitis, microscopic polyarteritis, mixed connective tissue disease, Muckle-Wells syndrome, multiple sclerosis, myasthenia gravis, opsoclonus myoclonus syndrome, optic neuritis, ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune haemolytic anemia, interstitial cystitis, Lyme disease, morphea, psoriasis, sarcoidosis, scleroderma, ulcerative colitis, vitiligo, T-cell mediated hypersensitivity diseases, contact hypersensitivity, contact dermatitis, uticaria, skin allergies, respiratory allergies, hay fever, allergic rhinitis, house dustmite allergy, gluten-sensitive enteropathy, Celiac disease, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, stomatisi, transplant rejection, acute pancreatitis, chronic pancreatitis, acute respiratory distress syndrome, Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensistivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) haemolytic anemia, leukemia and lymphomas in adults, acute leukaemia of childhood, regional enteritis, autoimmune vasculitis, multiple sclerosis, chronic obstructive pulmonary disease, solid organ transplant rejection, sepsis, rheumatoid arthritis, psoriatic arthritis, multiple sclerosis, Type 1 diabetes, asthma, inflammatory bowel disease, systemic lupus erythematosus, psoriasis, chronic obstructive pulmonary disease, inflammation accompanying infectious conditions, and sepsis.

6. The method of claim 1, wherein the disease is cancer.

7. The method of any claim 6, wherein the cancer is selected from: hematological malignancy, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma villosum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, pre-invasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, telangiectaltic sarcoma, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, and superficial spreading melanoma.

8. The method of claim 1, wherein the bacterial composition is administered orally, rectally, intravenously, intratumorally, or subcutaneously.

9. The method of claim 3, wherein at least 50% of the bacteria in the bacterial composition are *Blautia* Strain A.

10. The method of claim 3, wherein substantially all of the bacteria in the bacterial composition are *Blautia* Strain A.

11. The method of claim 3, wherein the bacterial composition comprises at least $1 \times 10^6$ colony forming units (CFUs) of *Blautia* Strain A.

12. The method of claim 1, wherein the bacterial composition comprises live bacteria, attenuated bacteria, or killed bacteria.

13. The method of claim 1, wherein the method further comprises administering to the subject an additional therapeutic.

14. The method of claim 13, wherein the additional therapeutic is selected from: an immunosuppressive agent, a DMARD, a pain-control drug, a steroid, a non-steroidal antiinflammatory drug (NSAID), a cytokine antagonist, cyclosporin, retinoids, corticosteroids, propionic acid derivative, acetic acid derivative, enolic acid derivatives, fenamic acid derivatives, Cox-2 inhibitors, lumiracoxib, ibuprofen, cholin magnesium salicylate, fenoprofen, salsalate, difunisal, tolmetin, ketoprofen, flurbiprofen, oxaprozin, indomethacin, sulindac, etodolac, ketorolac, nabumetone, naproxen, valdecoxib, etoricoxib, MK0966; rofecoxib, acetaminophen, Celecoxib, Diclofenac, tramadol, piroxicam, meloxicam, tenoxicam, droxicam, lornoxicam, isoxicam, mefanamic acid, meclofenamic acid, flufenamic acid, tolfenamic, parecoxib, aspirin, ibuprophen, firocoxib, methotrexate (MTX), antimalarial drugs, hydroxychloroquine, chloroquine, Leflunomide, azathiprine, gold salts, cyclophosphamide, D-penicillamine, minocycline, auranofin, tacrolimus, myocrisin, chlorambucil, TNF alpha antagonists, TNF alpha receptor antagonists, INFLIXIMAB (TA-650), CERTOLIZUMAB PEGOL (CDP870), GOLIMUMAB (CNTO 148), RITUXIMAB, ABATACEPT, TOCILIZUMAB Anakinra, CD4 antagonists, IL-20 antagonists, BLyS antagonists, Atacicept, belimumal p38 Inhibitors, CD20 antagonists, Ocrelizumab, Ofatumumab, interferon gamma antagonists, Fontolizumab, prednisolone, Prednisone, dexamethasone, Cortisol, cortisone, hydrocortisone, methylprednisolone, betamethasone, triamcinolone, beclometasome, fludrocortisone, deoxycorticosterone, aldosterone, Doxycycline, vancomycin, pioglitazone, SBI-087, SCIO-469, Cura-100, Oncoxin+Viusid, TwHF, Methoxsalen, Vitamin D—ergocalciferol, Milnacipran, Paclitaxel, rosig tazone, RADOO1, rapamune, rapamycin, fostamatinib, Fentanyl, XOMA 052, Fostamatinib disodium, rosightazone, Curcumin, Rosuvastatin, Maraviroc, ramipnl, Cobiprostone, somatropin, tgAAC94 gene therapy vector, MK0359, GW856553, esomeprazole, everolimus, trastuzumab, JAK1 and JAK2 inhibitors, pan JAK inhibitors, tetracyclic pyridone 6 (P6), 325, PF-956980, denosumab, IL-6 antagonists, CD20 antagonistis, CTLA4 antagnosts, IL-8 antagonists, IL-21 antagonists, IL-22 antagonist, integrin antagonists, (natalizumab4, VGEF antagnosits, CXCL antagonists, MMP antagonists, defensin antagonists, IL-1 antagonists, IL-1 beta antagonsits, IL-23 antagonists, receptor decoys, antagonistic antibodies, mesalazine, mesalamine, sulfasalazine, sulfasalazine derivatives, immunosuppressive drugs, cyclosporin A, mercaptopurine, azathiopurine, methotrexate, antihistamines, glucocorticoids, epinephrine, theophylline, cromolyn sodium, anti-leukotrienes, anti-cholinergic drugs for rhinitis, TLR antagonists, inflammasome inhibitors, anti-cholinergic decongestants, mast-cell stabilizers, monoclonal anti-IgE antibodies, vaccines, cytokine inhibitors, anti-IL-6 antibodies, TNF inhibitors, infliximab, adalimumab, certolizumab pegol, golimumab, and etanercept.

15. The method of claim 13, wherein the additional therapeutic is an immunosuppressive agent.

16. The method of claim 13, wherein the additional therapeutic is an antibiotic.

17. The method of claim 13, wherein the additional therapeutic is a cancer therapeutic.

18. The method of claim 17, wherein the cancer therapeutic comprises a chemotherapy agent.

19. The method of claim 1, wherein at least 50% of the bacteria in the bacterial composition are of the *Blautia* strain.

20. The method of claim 1, wherein substantially all of the bacteria in the bacterial composition are of the *Blautia* strain.

21. The method of claim 1, wherein the bacterial composition comprises at least $1 \times 10^6$ colony forming units (CFUs) of of the *Blautia* strain.

* * * * *